United States Patent
Yazaki et al.

[19]

[11] Patent Number: 6,133,284
[45] Date of Patent: Oct. 17, 2000

[54] PYRIDONECARBOXYLIC ACID DERIVATIVES OR THEIR SALTS, AND ANTIBACTERIAL AGENTS CONTAINING THE SAME AS THEIR EFFECTIVE COMPONENTS

[75] Inventors: Akira Yazaki; Yoshiko Niino; Yoshihiro Ohshita; Yuzo Hirao; Hirotaka Amano; Norihiro Hayashi; Yasuhiro Kuramoto, all of Hiroshima-ken, Japan

[73] Assignee: Wakunaga Pharmaceutical Co., Ltd., Osaka, Japan

[21] Appl. No.: 09/329,246

[22] Filed: Jun. 10, 1999

Related U.S. Application Data

[62] Division of application No. 09/043,472, filed as application No. PCT/JP96/02710, Sep. 20, 1996, Pat. No. 5,998,436.

[30] Foreign Application Priority Data

Sep. 22, 1995 [JP] Japan ................................ 7-269280
Jun. 19, 1996 [JP] Japan ................................ 8-178462

[51] Int. Cl.[7] .......................... A61K 31/47; C07D 215/16
[52] U.S. Cl. ............................................ 514/312; 546/156
[58] Field of Search .............................. 514/312; 546/156

[56] References Cited

U.S. PATENT DOCUMENTS

| | | | |
|---|---|---|---|
| 4,994,599 | 2/1991 | Chu | 558/44 |
| 5,519,016 | 5/1996 | Kimura | 514/212 |
| 5,631,256 | 5/1997 | Demuth | 514/252 |
| 5,703,231 | 12/1997 | Randall | 540/200 |

FOREIGN PATENT DOCUMENTS

| | | |
|---|---|---|
| 61-152682 | 7/1986 | Japan . |
| 6-116241 | 4/1994 | Japan . |
| WO95 05373 | 2/1995 | WIPO . |
| WO96 02511 | 2/1996 | WIPO . |
| WO96 02540A1 | 2/1996 | WIPO . |
| WO96 12704 | 5/1996 | WIPO . |
| WO96 23775 | 8/1996 | WIPO . |

*Primary Examiner*—D. Margaret Seaman
*Attorney, Agent, or Firm*—Birch, Stewart, Kolasch & Birch, LLP

[57] ABSTRACT

A pyridonecarboxylic acid derivative represented by the following general formula (1):

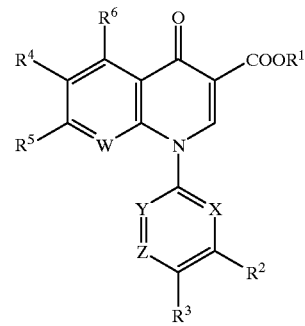

(1)

[wherein $R^1$ represents hydrogen atom or a carboxyl protective group; $R^2$ represents hydroxyl group, a lower alkoxy group, or a substituted or unsubstituted amino group; $R^3$ represents hydrogen atom or a halogen atom; $R^4$ represents hydrogen atom or a halogen atom; $R^5$ represents a halogen atom or an optionally substituted saturated cyclic amino group; $R^6$ represents hydrogen atom, a halogen atom, nitro group, or an optionally protected amino group; X, Y and Z may be the same or different and respectively represent nitrogen atom, —CH= or —CR$^7$= (wherein $R^7$ represents a lower alkyl group, a halogen atom, or cyano group) (with the proviso that at least one of X, Y and Z represent the nitrogen atom), and W represents nitrogen atom or —CR$^8$= (wherein $R^8$ represents hydrogen atom, a halogen atom, or a lower alkyl group)]
or its salt, as well as an antibacterial agent containing such compound are provided.

3 Claims, No Drawings

PYRIDONECARBOXYLIC ACID DERIVATIVES OR THEIR SALTS, AND ANTIBACTERIAL AGENTS CONTAINING THE SAME AS THEIR EFFECTIVE COMPONENTS

This application is a divisional of application 09/043,472, filed on Mar. 20, 1998, now U.S. Pat. No. 5,998,636. Application No. 09/043,472 is the national phase of PCT International Application No. PCT/JP96/02710 filed on Sep. 20, 1996 under 35 U.S.C. §371. The entire contents of each of the above identified applications are hereby incorporated by reference.

TECHNICAL FIELD

The present invention relates to novel pyridonecarboxylic acid derivatives or salts thereof having excellent antibacterial properties and oral absorption, and antibacterial agents containing the same.

BACKGROUND ART

Many compounds having basic skeleton of pyridonecarboxylic acid are known to be useful synthetic antibacterials for their excellent antibacterial properties and wide antibacterial spectrum. Among such compounds, norfloxacin (Japanese Patent Application Laid-Open No. 53-141286), enoxacin (Japanese Patent Application Laid-Open No. 55-31042), ofloxacin (Japanese Patent Application Laid-Open No. 57-46986), ciprofloxacin (Japanese Patent Application Laid-Open No. 58-76667), tosufloxacin (Japanese Patent Application Laid-Open No. 60-228479), and the like are widely used in clinical practice for treating infections.

These compounds, however, need further improvements in antibacterial activities, intestinal absorption, metabolic stability, and side effects, and in particular, in phototoxicity, cytotoxicity.

Accordingly, an object of the present invention is to provide novel compounds which are sufficient in such aspects.

DISCLOSURE OF THE INVENTION

In view of such situation, the inventors of the present invention have made an intensive study to find compounds which would be excellent synthetic antibacterial agents in clinical practice, and found that novel compounds represented by the following general formula (1) has good antibacterial properties to gram negative and positive bacteria as well as an extremely low toxicity, and therefore, would be a very useful synthetic antibacterial. The present invention has been accomplished on the bases of such a finding.

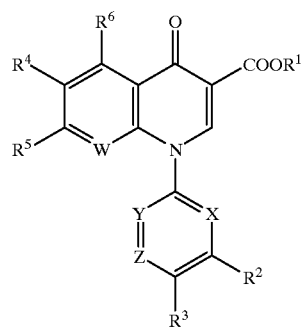

(1)

[In the formula, $R^1$ represents hydrogen atom or a carboxyl protective group; $R^2$ represents hydroxyl group, a lower alkoxy group, or a substituted or unsubstituted amino group; $R^3$ represents hydrogen atom or a halogen atom; $R^4$ represents hydrogen atom or a halogen atom; $R^5$ represents a halogen atom or an optionally substituted saturated cyclic amino group; $R^6$ represents hydrogen atom, a halogen atom, nitro group, or an optionally protected amino group; X, Y and Z may be the same or different and respectively represent nitrogen atom, —CH= or —CR$^7$= (wherein $R^7$ represents a lower alkyl group, a halogen atom, or cyano group) (with the proviso that at least one of X, Y and Z represents the nitrogen atom), and W represents nitrogen atom or —CR$^8$= (wherein $R^8$ represents hydrogen atom, a halogen atom, or a lower alkyl group.)]

Accordingly, the present invention provides pyridonecarboxylic acid derivatives represented by the general formula (1), above, or their salts, and antibacterial agents containing the pyridonecarboxylic acid derivatives or their pharmaceutically acceptable salts as their effective components.

BEST MODE FOR CARRYING OUT THE INVENTION

The novel pyridonecarboxylic acid derivatives of the present invention are represented by the general formula (1) as shown above, and the term "lower" used for the substituents of the pyridonecarboxylic acid derivatives represented by the general formula (1) designates that the substituent comprises 1 to 7 carbon atoms, and preferably 1 to 5 carbon atoms in the case of a linear substituent, and that the substituent comprises 3 to 7 carbon atoms in the case of a cyclic substituent.

In the general formula (1), $R^1$ represents hydrogen atom or a carboxyl-protective group, and the term, carboxyl-protective group herein designates an ester residue of a carboxylate ester, and the carboxyl protective group may be any carboxylate ester residue which cleaves relatively easily to generate the corresponding free carboxyl group. Exemplary carboxyl protective groups include those which may be eliminated by hydrolysis, catalytic reduction, and other treatments under mild conditions such as lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group; and aryl groups such as phenyl group and naphthyl group; and those which may be readily eliminated in the body such as lower alkanoyloxy lower alkyl groups such as acetoxymethyl group and pivaloyloxymethyl group; lower alkoxycarbonyloxy lower alkyl group such as methoxycarbonyloxymethyl group and 1-ethoxy-carbonyloxyethyl group; lower alkoxymethyl group such as methoxymethyl group; lactonyl group such as phthalidyl; di-lower alkylamino lower alkyl group such as 1-dimethyl-aminoethyl group; and (5-methyl-2-oxo-1,3-dioxole-4-yl)methyl group. It should be noted that $R^1$ is most preferably hydrogen atom.

In the general formula (1), $R^2$ represents hydroxyl group, a lower alkoxy group, or a substituted or unsubstituted amino group. Exemplary substituents for the substituted amino group include lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group and 1-phenylethyl; aryl groups such as phenyl group and naphthyl group; lower alkanoyl groups such as formyl group, acetyl group, propionyl group, butylyl group, and isobutylyl group; lower alkoxycarbonyl groups such as methoxycarbonyl group and ethoxycarbonyl group; aroyl groups such as benzoyl group and naphthoyl group; amino acid residues or oligopeptide residues such as glycyl, leucyl, valyl, alanyl, phenylalanyl, alanyl-alanyl, glycyl-valyl, and glycyl-glycyl-valyl, and the amino acid residues or the oligopeptide residues wherein the functional group thereof is protected with an acyl, a lower aralkyl, or other protective groups which is commonly used in peptide chemistry; and cyclic amino group. One or two substituents which may be the same or different may be selected from the substituents as described above. The compound protected with the amino acid residue or the oligopeptide residue is expected to have an improved water solubility.

Preferably, $R^2$ is amino group, a lower alkylamino group, a di-lower alkylamino group, a lower alkanoylamino group, an amino acid-substituted amino group, or an oligopeptide-substituted amino group. More preferable examples of $R^2$ include amino group, methylamino group, ethylamino group, and dimethylamino group, among which the amino group being the most preferred. It should be noted that the exemplary preferable lower alkoxy groups used for $R^2$ include lower alkoxy groups having 1 to 4 carbon atoms such as methoxy group, ethoxy group, propoxy group, and butoxy group, and among these, use of methoxy group is preferable.

Next, in the general formula (1), $R^3$ represents hydrogen atom or a halogen atom; $R^4$ represents hydrogen atom or a halogen atom; $R^5$ represents a halogen atom or an optionally substituted saturated cyclic amino group; $R^6$ represents hydrogen atom, a halogen atom, nitro group, or an optionally protected amino group; X, Y and Z may be the same or different and respectively represent nitrogen atom, —CH= or —CR$^7$= (wherein $R^7$ represents a lower alkyl group, a halogen atom, or cyano group), and W represents nitrogen atom or —CR$^8$= (wherein $R^8$ represents hydrogen atom or a halogen atom).

The halogen atoms represented by $R^3$, $R^4$, $R^5$, $R^6$, $R^7$ and $R^8$ include fluorine atom, chlorine atom, bromine atom and iodine atom. Among these, fluorine atom and chlorine atom are the preferred, and in particular, $R^3$ to $R^7$ are preferably fluorine atom and $R^8$ is preferably chlorine atom or bromine atom.

The lower alkyl groups represented by $R^7$ and $R^8$ include those containing 1 to 7 carbon atoms such as methyl group, ethyl group, propyl group, butyl group, pentyl group, hexyl group, and heptyl group, among which methyl group is the preferred.

With regard to X, Y and Z. two or three of X, Y and Z may be the same, or alternatively, they may be different from each other. It is, however, required that at least one of X, Y and Z is nitrogen atom. Exemplary preferable combinations of X, Y and Z are nitrogen for X and —CH= or —CR$^7$= (wherein $R^7$ represents a lower alkyl group, a halogen atom or cyano group) for Y and Z; nitrogen for Y and —CH= or —CR$^7$= (wherein $R^7$ represents a lower alkyl group or a halogen atom) for X and Z; and nitrogen for X and Y, and —CH= or —CR$^7$= (wherein $R^7$ represents a lower alkyl group or a halogen atom) for Z.

It should be also noted that the compound of formula (1) has naphthylidine skeleton when W represents nitrogen, and quinoline skeleton when W represents —CR$^8$=, and it is most preferable that W represents —CR$^8$= (wherein RB represents a halogen atom or a lower alkyl group).

Next, the optionally substituted saturated cyclic amino group represented by the $R^5$ may additionally contain 1 or more heteroatoms such as nitrogen atom, oxygen atom, and sulfur atom as well as carbonyl carbon in its ring, and may be either monocyclic, or bi- or tricyclic. The saturated cyclic amino group is preferably a 4 to 7-membered ring when it is monocyclic, a 7 to 11-membered ring when it is bicyclic, and 9 to 15-membered ring when it is tricyclic. Exemplary such cyclic amino groups include saturated monocyclic amino groups of 3 to 7-membered ring containing one nitrogen atom such as aziridin-1-yl, azetidin-1-yl, pyrrolidin-1-yl, and piperidin-1-yl; saturated monocyclic amino groups of 3 to 7-membered ring containing two nitrogen atoms such as piperazin-1-yl and homopiperazin-1-yl; saturated monocyclic amino groups of 3 to 7-membered ring containing a heteroatom selected from oxygen atom and sulfur atom in addition to nitrogen atom such as oxazolidin-3-yl, morpholin-4-yl, thiazolidin-1-yl, and thiomorpholin-4-yl; saturated bi- or tricyclic amino groups such as tetrahydroquinolin-1-yl; and spiro or cross-linked saturated amino groups of 5 to 12-membered ring such as 2,8-diazaspiro[4.4]nonan-2-yl, 5-azaspiro[2.4)heptan-5-yl, 7-azabicyclo[2.2.1]heptan-7-yl, 2,8-diazabicyclo[4.3.0]nonan-8-yl, 5-methyl-2,5-diazabicyclo[2.2.1]heptan-2-yl, 2,5-diazabicyclo[2.2.1]heptan-2-yl, and 3,8-diazabicyclo[3.2. 1]octan-3-yl.

The atom constituting the ring of such saturated cyclic amino group may be substituted with an appropriate substituent, and exemplary such substituents include hydroxyl group, lower alkyl groups, substituted and unsubstituted amino groups, substituted and unsubstituted amino lower alkyl groups, lower alkoxy groups, and halogen atoms.

Exemplary lower alkyl groups for the substituent of the saturated cyclic amino group include those containing 1 to 7 carbon atoms such as methyl group, ethyl group, propyl group, butyl group, pentyl group, hexyl group, and heptyl group; and exemplary lower alkoxy groups include those containing 1 to 7 carbon atoms such as methoxy group, ethoxy group, and n-propoxy group; and exemplary halogen groups include fluorine atom, chlorine atom, and bromine atom. Of the substituents of the saturated cyclic amino groups, the substituted amino groups and substituted amino lower alkyl groups may have a substituent which may be the same as those described for $R^2$, and preferable examples of the substituted amino groups and the substituted and unsubstituted amino lower alkyl groups include methylamino group, ethylamino group, dimethylamino group, aminomethyl group, 1-aminoethyl group, 2-aminoethyl group, 1-amino-1-ethyl group, methylaminomethyl group, ethylaminomethyl group, dimethylaminomethyl group, glycyl-amino group, leucyl-amino group, valyl-amino group, alanyl-amino group, and alanyl-alanyl-amino group.

Of the saturated cyclic amino groups as described above, the most preferable group for R⁵ include those represented by the following formulae (a) and (b):

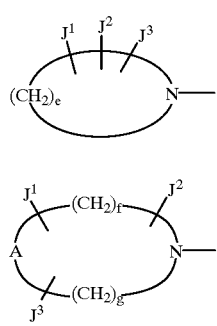

(a)

(b)

[wherein A represents oxygen atom, sulfur atom or NR⁹ (wherein R⁹ represents hydrogen atom or a lower alkyl group), e represents a number of from 3 to 5, f represents a number of from 1 to 3, g represents a number of from 0 to 2, J¹, J² and J³, which may be the same or different, represent hydrogen atom, hydroxyl group, a lower alkyl group, an amino lower alkyl group, amino group, a lower alkylamino group, a lower alkoxy group, or a halogen atom.]

Examples of the lower alkyl group, the amino lower alkyl group, the lower alkylamino group, the lower alkoxy group, and the halogen atom in the formulae (a) and (b) as described above are the same as those shown for R² to R⁵.

Exemplary cyclic amino groups represented by the formula (a) include azetidin-1-yl, pyrrolidin-1-yl, and piperidin-1-yl, and exemplary cyclic amino groups represented by the formula (b) include piperazin-1-yl, morpholin-4-yl, thiomorpholin-4-yl, homopiperazin-1-yl, N-thiazolidinyl, and N-oxazolidinyl. When R⁵ is a cyclic amino group, R⁵ is preferably the cyclic amino group represented by formula (a), and R⁵ is most preferably azetidin-1-yl or pyrrolidin-1-yl.

The most preferable examples of the groups represented by the formulae (a) and (b) are as described below. 3-aminoazetidin-1-yl group, 3-methylaminoazetidin-1-yl group, 3-dimethylaminoazetidin-1-yl group, 3-aminomethylazetidin-1-yl group, 3-amino-2-methylazetidin-1-yl group, 3-amino-3-methylazetidin-1-yl group, 3-alanyl-aminoazetidin-1-yl group, 3-valyl-aminoazetidin-1-yl group, 3-pyrrolidin-1-yl group, 3-hydroxypyrrolidin-1-yl group, 3,4-dihydroxypyrrolidin-1-yl group, 3-methoxypyrrolidin-1-yl group, 3-methylpyrrolidin-1-yl group, 3-hydroxy-4-methylpyrrolidin-1-yl group, 3-aminopyrrolidin-1-yl group, 3-methylaminopyrrolidin-1-yl group, 3-dimethylaminopyrrolidin-1-yl group, 3-ethylaminopyrrolidin-1-yl group, 3-diethylaminopyrrolidin- 1-yl group, 3-aminomethylpyrrolidin-1-yl group, 3-amino-3-methylpyrrolidin-1-yl group, 3-amino-4-methylpyrrolidin-1-yl group, 3-amino-5-methylpyrrolidin-1-yl group, 3-methylamino-4-methylpyrrolidin-1-yl group, 3-dimethylamino-4-methylpyrrolidin-1-yl group, 3-ethylamino-4-methylpyrrolidin-1-yl group, 3-diethylamino-3-methylpyrrolidin-1-yl group, 3-diethylamino-4-methylpyrrolidin-1-yl group, 3-aminomethyl-4-methylpyrrolidin-1-yl group, 3-methylaminomethyl-4-methylpyrrolidin-1-yl group, 3-dimethylaminomethyl-4-methylpyrrolidin-1-yl group, 3-ethylaminomethyl-4-methylpyrrolidin-1-yl group, 3-(l-aminoethyl)-4-methylpyrrolidin-1-yl group, 3-(2-aminoethyl)-4-methylpyrrolidin-1-yl group, 3-aminoethyl) 4-ethylpyrrolidin-1-yl group, 3-methylamino-4-ethylpyrrolidin-1-yl group, 3-dimethylamino-4-ethylpyrrolidin-1-yl group, 3-ethylamino-4-ethylpyrrolidin-1-yl group, 3-diethylamino-4-ethylpyrrolidin-1-yl group, 3-aminomethyl-4-ethylpyrrolidin-1-yl group, 3-methylaminomethyl-4-ethylpyrrolidin-1-yl group, 3-dimethylaminomethyl-4-ethylpyrrolidin-1-yl group, 3-amino-3-methylpyrrolidin-1-yl group, 3-methylamino-3-methylpyrrolidin-1-yl group, 3-dimethylamino-3-methylpyrrolidin-1-yl group, 3-amino-3,4-dimethylpyrrolidin-1-yl group, 3-amino-4,4-dimethylpyrrolidin-1-yl group, 3-amino-4,5-dimethylpyrrolidin-1-yl group, 3-amino-2,4-dimethylpyrrolidin-1-yl group, 3-methylamino-3,4-dimethylpyrrolidin-1-yl group, 2-methyl-3-aminopyrrolidin-1-yl group, 2-methyl-3-dimethylaminopyrrolidin-1-yl group, 3-amino-4-methoxypyrrolidin- 1-yl group, 3-alanyl-aminopyrrolidin-1-yl group, 3-valyl-aminopyrrolidin-1-yl group, piperazin-1-yl group, 4-methylpiperazin-1-yl group, 3-methylpiperazin-1-yl group, 2-methylpiperazin-1-yl group, 3,4-dimethylpiperazin-1-yl group, 3,5-dimethylpiperazin-1-yl group, 3,3-dimethylpiperazin-1-yl group, 3,4,5-trimethylpiperazin-1-yl group, piperidin-1-yl group, 4-aminopiperidin-1-yl group, 4-dimethylaminopiperidin-1-yl group, 4-hydroxypiperidin-1-yl group, morpholin-4-yl group, 2-aminomethylmorpholin-4-yl group, 2-methylaminomorpholin-4-yl group, 2-dimethylaminomorpholin-4-yl group, thiomorpholin-4-yl group, homopiperazin-1-yl group, 4-methylhomopiperazin-1-yl group, N-thiazolidinyl group, and N-oxazolidinyl group.

The optionally protected amino group represented by R⁶ include amino group as well as amino group protected by an appropriate protective group. Exemplary such protected amino groups include the amino group protected with a lower alkanoyl group such as formyl, acetyl, propionyl, pivaloyl, hexaloyl, or the like; a lower alkoxycarbonyl group such as methoxycarbonyl, ethoxycarbonyl, propoxycarbonyl, t-butoxycarbonyl, t-pentyloxycarbonyl, hexyloxycarbonyl, or the like; an aroyl such as benzoyl, toluoyl, naphthoyl, or the like; an aryl lower alkanoyl group such as phenylacetyl, phenylpropionyl, or the like; an aryloxycarbonyl group such as phenoxycarbonyl, naphthyloxycarbonyl, or the like; an aryloxy lower alkanoyl group such as phenoxyacetyl, phenoxypropionyl, or the like; an aralkyloxycarbonyl group such as benzyloxycarbonyl, phenethyloxycarbonyl, or the like; or an aralkyl group such as benzyl, phenethyl, benzhydryl, trityl, or the like.

The preferable combination of the R¹, R², R³, R⁴, R5, R⁶, X, Y, Z, and W is such that R¹ is hydrogen atom, R² is amino group, a lower alkylamino group, or a di-lower alkylamino group, R³ is a halogen atom, R⁴ is a halogen atom, X is nitrogen atom, Y and Z are —CH= or —CR⁷= (wherein R⁷ is a lower alkyl group or a halogen atom), W is —CR⁸= (R⁸ is a halogen atom or a lower alkyl group), R⁵ is a group represented by formula (a) (e=3 or 4), and R⁶ is hydrogen atom. The more preferable combination of the R¹, R², R³, R⁴, R⁵, R⁶, X, Y, Z, and W is such that R¹ is hydrogen atom, R² is amino group, R³ is fluorine atom, R⁴ is fluorine atom, X is nitrogen atom, Y is —CF=, Z is —CH=, W is —CCl=, —CBr= or —CCH₃=, R⁵ is a group represented by formula (a) (e=3), and R⁶ is hydrogen atom.

The salts of the pyridonecarboxylic acid derivatives of the formula (1) as described above may be either acid adduct salts or base adduct salts. The term, salts used herein also include chelate salts with a boron compound. Exemplary acid adduct salts include (i) salts with a mineral acid such as hydrochloric acid or sulfuric acid; (ii) salts with an organic carboxylic acid such as formic acid, citric acid, trichloroacetic acid, trifluoroacetic acid, fumaric acid, or maleic acid; and (iii) salts with a sulfonic acid such as methanesulfonic acid, benzenesulfonic acid, p-toluenesulfonic acid, mesitylenesulfonic acid, or naphthalenesulfonic acid; and exemplary base adduct salts include (i') salts with an alkaline metal such as sodium or potassium; (ii') salts with an alkaline earth metal such as calcium or magnesium; (iii') ammonium salts; (iv') salts with a nitrogen-containing organic base such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine, or N,N'-dibenzylethylenediamine. Exemplary boron compounds include boron halides such as boron fluoride, and lower acyloxyborons such as acetoxyboron.

The pyridonecarboxylic acid derivatives and the salts thereof of the present invention may also be in the form of a hydrate or a solvate in addition to the non-solvated form. Accordingly, the compound of the present invention includes all of the crystalline form, the hydrate form, and the solvate form. Furthermore, the pyridonecarboxylic acid derivatives and the salts thereof may be present in the form of an optically active substance, and such optically active substance is also within the scope of the compounds of the present invention. Still further, the pyridonecarboxylic acid derivative and the salt thereof may be present in the form of a (cis or trans) stereoisomer, and such stereoisomer is also within the scope of the compounds of the present invention.

The pyridonecarboxylic acid derivatives and the salts thereof of the present invention represented by the formula (1) as described above may be produced by any procedure appropriately selected in accordance with such factors as the type of the substituents, and an exemplary procedure is as described below.

(Procedure 1)

Of the compounds represented by the general formula (1), the compounds (1a) wherein $R^1$ is hydrogen atom or a lower alkyl group, and $R^5$ is a halogen atom may be produced, for example, by Procedure 1 represented by the reaction scheme as described below:

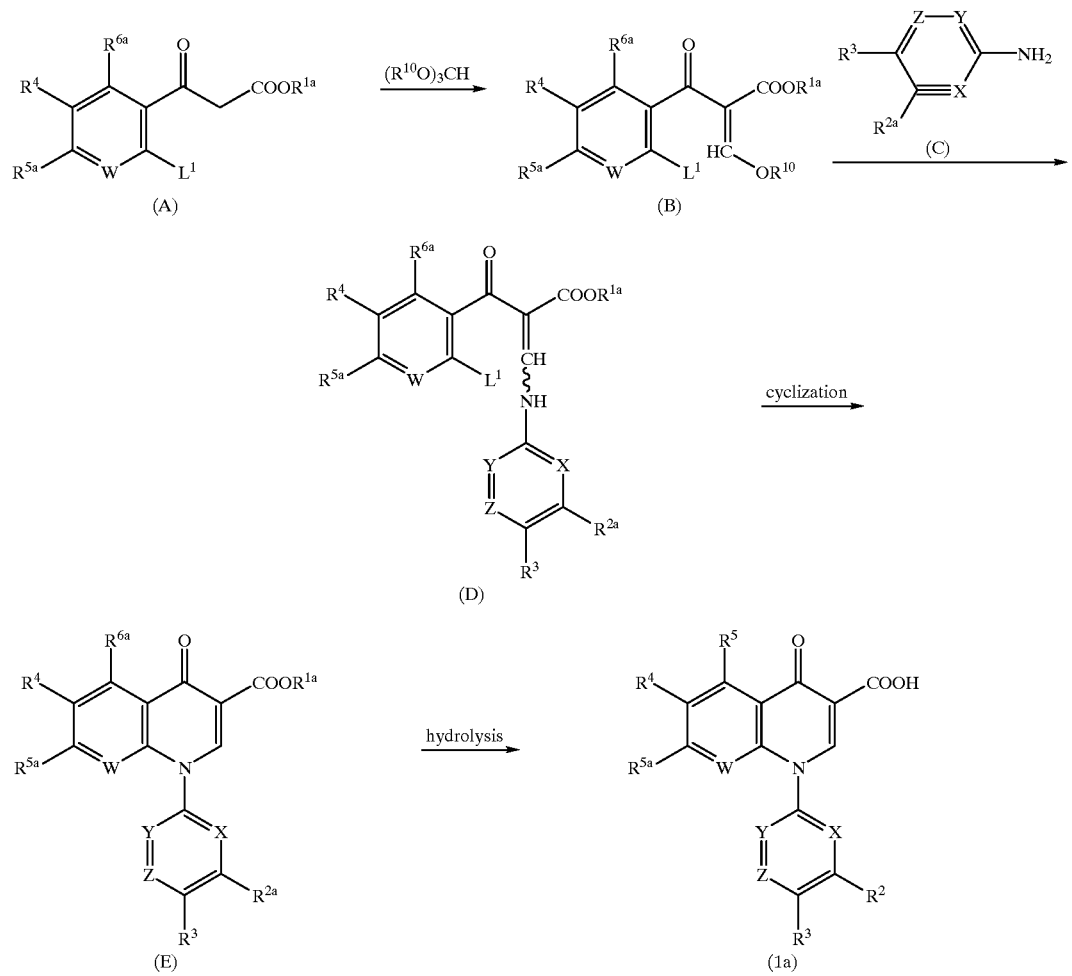

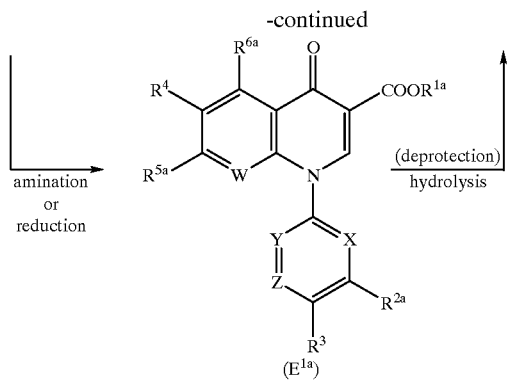

[wherein $R^{1a}$ represents a lower alkyl group; $R^{10}$ represents a lower alkyl group; $L^1$ represents a halogen atom; $R^{5a}$ represents a halogen atom; $R^{2a}$ represents hydroxyl group, a lower alkoxy group, or a substituted or unsubstituted amino group or protected amino group; $R^{6a}$ represents hydrogen atom, a halogen atom, or nitro group; $R^{6b}$ represents an optionally substituted amino group; $R^2$, $R^3$, $R^4$, $R^6$, X, Y, Z, and W are as defined above.]

More illustratively, the compound (1a) of the present invention is produced by reacting compound (A) with an orthoformate such as methyl orthoformate or ethyl orthoformate to produce acrylate derivative (B); reacting the acrylate derivative (B) with an amino compound (C) to produce compound (D); cyclizing the compound (D) to produce compound (E); and hydrolyzing the compound (E) to obtain the compound (1a).

The reaction between the compound (A) and the orthoformate is generally carried out at 0 to 160° C., and preferably 50 to 150° C. usually for a reaction period of 10 minutes to 48 hours, and preferably for 1 to 10 hours. The orthoformate is used in equimolar amount or more to the compound (A), and preferably, in 1 to 10 times the molar amount to the compound (A).

The reaction with the compound (C) may be effected with no solvent or in a solvent. The solvent used in this reaction may be any solvent as long as the reaction is not affected by the solvent, and the exemplary solvents include aromatic hydrocarbons such as benzene, toluene, and xylene; ethers such as diethylether, tetrahydrofuran, dioxane, monoglyme, and diglyme; aliphatic hydrocarbons such as pentane, hexane, heptane, and ligroin; halogenated hydrocarbons such as methylene chloride, chloroform, and carbon tetrachloride; nonprotonic polar solvents such as dimethylformamide and dimethylsulfoxide; and alcohols such as methanol, ethanol and propanol. This reaction is generally conducted at 0 to 150° C., and preferably at 0 to 100° C. usually for a reaction period of 10 minutes to 48 hours. The compound (C) is used in equimolar amount or more to the compound (A), and preferably, in 1 to 2 times the molar amount to the compound (A).

Alternatively, compound (A) may be reacted with an acetal such as N,N-dimethylformamide dimethylacetal or N-dimethylformamide diethylacetal, and then, with compound (C) to produce the compound (D). The solvent used in the reaction with the acetal may be any solvent as long as the reaction is not affected by the solvent, and the exemplary solvents are those described in the foregoing. This reaction is generally conducted at 0 to 150° C., and preferably at room temperature to 100° C. generally for a reaction period of 10 minutes to 48 hours, and preferably for 1 to 10 hours.

Next, the cyclization of the compound (D) into the compound (E) is conducted in an adequate solvent either in the presence or absence of a basic compound. The solvent used in this reaction may be any solvent as long as the reaction is not affected by the solvent, and the exemplary solvents include aromatic hydrocarbons such as benzene, toluene, and xylene; ethers such as diethylether, tetrahydrofuran, dioxane, and monoglyme; halogenated hydrocarbons such as methylene chloride, chloroform, and carbon tetrachloride; alcohols such as methanol, ethanol, propanol, and butanol; and nonprotonic polar solvents such as dimethylformamide and dimethylsulfoxide. Exemplary basic compounds used are alkaline metals such as metal sodium and metal potassium; metal hydrides such as sodium hydride and calcium hydride; inorganic salts such as sodium hydroxide, potassium hydroxide, sodium carbonate, and potassium carbonate; alkoxides such as sodium methoxide, sodium ethoxide, and potassium t-butoxide; metal fluorides such as sodium fluoride and potassium fluoride; organic salts such as triethylamine and 1,8-diazabicyclo[5.4.0]undecene (DBU). This reaction is conducted at a reaction temperature of 0 to 200° C., and preferably, at room temperature to 180° C., and the reaction is generally completed in 5 minutes to 24 hours. The basic compound is used in equimolar amount or more to the compound (D), and preferably, in 1 to 2 times the molar amount to the compound (D).

The compound (E) is subjected to hydrolysis to eliminate the carboxyl protective group $R^{1a}$ and/or the amino protective group $R^{2a}$ to obtain compound (1a).

The hydrolysis may be conducted under any conditions commonly used in the hydrolysis, for example, in the presence of a basic compound such as sodium hydroxide, potassium hydroxide, sodium carbonate, and potassium carbonate, a mineral acid such as hydrochloric acid, sulfuric acid, and hydrobromic acid, or an organic acid such as p-toluenesulfonic acid, and in a solvent such as water, an alcohol such as methanol, ethanol or propanol, or an ether such as tetrahydrofuran or dioxane, a ketone such as acetone or methylethylketone, acetic acid, or a mixture of such solvents. The reaction is generally conducted at room temperature to 180° C., and preferably, at room temperature to 140° C. usually for a reaction period of 1 to 24 hours.

It should be noted that in the case of producing a compound wherein $R^6$ in formula (1) is an optionally protected amino group, the compound (E) is first produced through the reactions as described above by using a compound (A) wherein $R^{6a}$ is a halogen atom or nitro group for the starting material, and the compound ($E^{1a}$) is then produced by aminating said halogen atom or by reducing the nitro group, and the compound (1a) is derived from the compound ($E^{1a}$) by eliminating the amino protective group if necessary and eliminating the carboxyl protective group.

(Procedure 2)

Of the compounds represented by the general formula (1), the compounds wherein $R^5$ is an optionally substituted saturated cyclic amino group may be produced, for example, by the procedure 2 represented by the reaction scheme as described below:

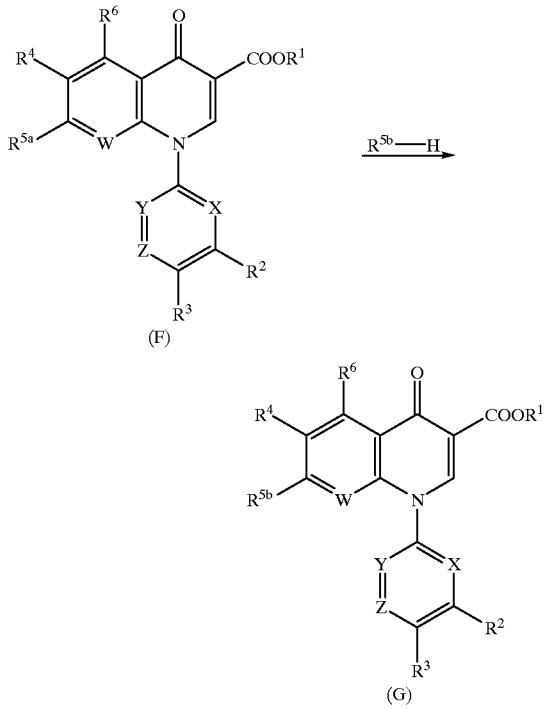

[wherein $R^{5b}$ represents an optionally substituted saturated cyclic amino group; and $R^1$, $R^2$, $R^3$, $R^4$, $R^{5a}$, $R^6$, X, Y, Z, and W are as defined above.]

More illustratively, compound (G) is obtained by aminating compound (F) using the compound represented by the formula: $R^{5b}$—H.

This reaction may be conducted in a solvent which does not affect the reaction such as an aromatic hydrocarbon such as benzene, toluene, or xylene; an alcohol such as methanol or ethanol; an ether such as tetrahydrofuran, dioxane, or monoglyme; a halogenated hydrocarbon such as methylene chloride, chloroform, or carbon tetrachloride; a nonprotonic polar solvent such as dimethylformamide, dimethylsulfoxide, or N-methylpyrrolidone; acetonitrile, or pyridine, and in the optional presence of a neutralizer such as sodium carbonate, calcium carbonate, sodium hydrogencarbonate, triethylamine, 1,8-diazabicyclo[5.4.0]undecene (DBU) at room temperature to 160° C. The reaction period is from several minutes to 48 hours, and preferably, from 10 minutes to 24 hours. The compound $R^{5b}$—H is used in equimolar amount or more to the compound (F), and preferably, in 1 to 5 times the molar amount to the compound (F). It should be noted that the compound (F) may be obtained as in the Procedure 1 as described above, and that, when $R^1$ is a carboxyl protective group, it may be replaced with a hydrogen atom by hydrolysis.

(Procedure 3)

Of the compounds represented by the general formula (1), the compounds wherein $R^1$ is a carboxyl protective group may be produced, for example, by the procedure 3 represented by the reaction scheme as described below:

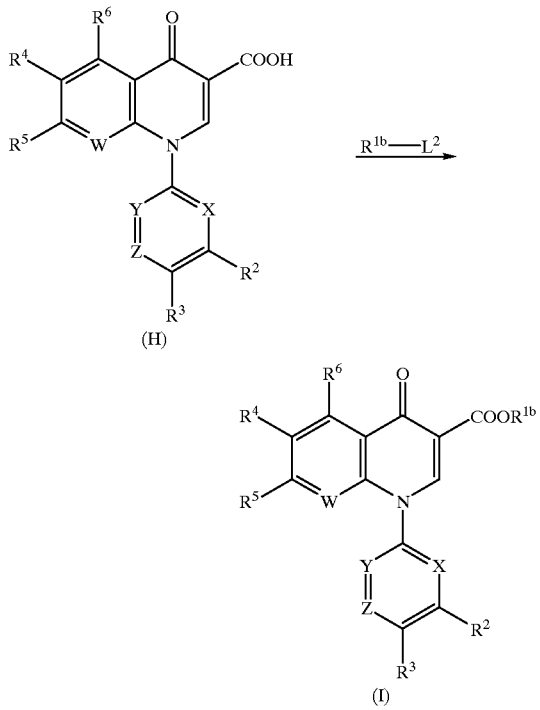

(wherein $R^{1b}$ represents a carboxyl protective group; $L^2$ represents a halogen atom; and $R^2$, $R^3$, $R^4$, $R^5$, $R^6$, X, Y, Z, and W are as defined above.]

More illustratively, compound (I) is obtained by reacting compound (H) with a halogen compound: $R^{1b}$—$L^2$. The solvents which may be used in this reaction include aromatic hydrocarbons such as benzene and toluene; halogenated hydrocarbons such as methylene chloride and chloroform; nonprotonic polar solvents such as dimethylformamide and dimethylsulfoxide; and inert solvents such as acetonitrile. The reaction temperature is usually from room temperature to 100° C. The reaction is preferably conducted in the presence of a basic compound such as triethylamine, diisopropylethylamine, dicyclohexylamine, DBU, sodium carbonate, potassium carbonate, and sodium hydroxide. It should be noted that the compound (H) may be obtained by the Procedure 1 and Procedure 2 as described above.

When amino group, imino group, hydroxy group, mercapto group, carboxyl group or the like which is not involved in the reaction is present in the starting materials of the Procedure 1, 2, or 3 as described above, such group may be protected during the reaction, and the protective group may be eliminated after the completion of the reaction by a conventional method. The protective group used in such a case may be any group as long as the compound of the present invention produced by the reaction can be deprotected with no decomposition of its structure, and any group commonly used in the field of peptide, amino sugar, and nucleic acid chemistry may be preferably used ("Protective Groups in Organic Synthesis", Second Editor, T. W. Green and P. G. M. Wuts, John Wiley & Sons Inc., 1991).

1) J. Heterocyclic Chem. 22, 1033 (1985)
2) Liebigs Ann. Chem. 29 (1987)
3) J. Med. Chem. 31, 991 (1988)
4) J. Org. Chem. 35, 930 (1970)
5) Japanese Patent Application Laid-Open No. 62-246541
6) Japanese Patent Application Laid-Open No. 62-26272
7) Japanese Patent Application Laid-Open No. 63-145268

8) J. Med. Chem. 29, 2363 (1986)
9) J. Fluorin Chem. 28, 361 (1985)
10) Japanese Patent Application Laid-Open No. 63-198664
11) Japanese Patent Application Laid-Open No. 63-264461
12) Japanese Patent Application Laid-Open No. 63-104974
13) European Patent Application No. 230948
14) Japanese Patent Application Laid-Open No. 2-282384
15) Published Japanese Translation of PCT International Publication for Patent Application No. 3-502452
16) J. Het. Chem. 27, 1609 (1990)

The starting compound (C) may be produced by any process, and an exemplary production process is as described below.

The starting compound (C) may be obtained by replacing the halogen atom bonded to the carbon atom constituting the 6-membered ring with an amine such as ammonia, an alkylamine, benzylamine, or the like by a known halogen-amine substitution reaction. It should be noted that when a substituted amine such as an alkyl amine or benzyl amine is used for the amine, the substituent of the substituted amino group may be adequately eliminated by a conventional method as shown in the reaction scheme, below. When $R^{2a}$ is a substituted or unsubstituted amino group or amino group substituted with a protective group, similar halogen-amine replacement reaction may be conducted.

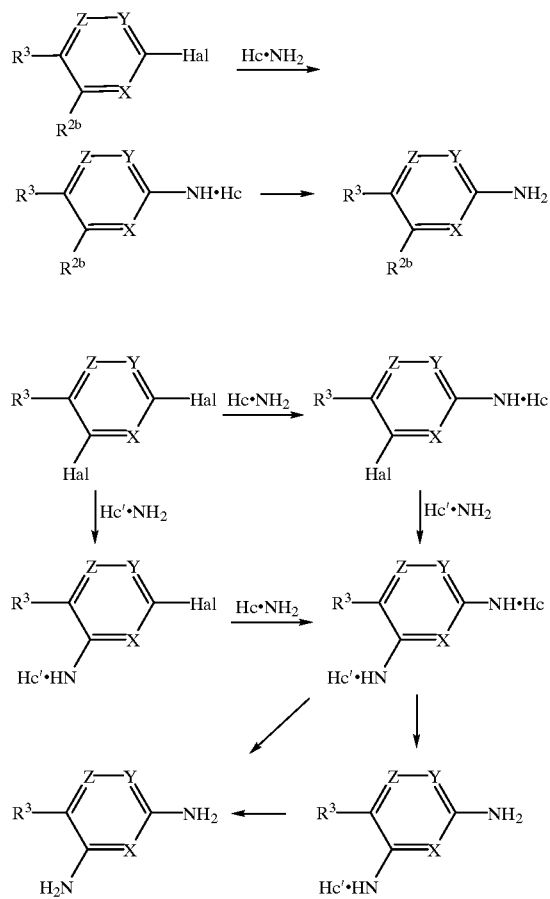

[In the formula, Hal represents a halogen atom such as F or Cl; Hc.NH and Hc'.NH are respectively a substituted amino group or an amino group substituted with a protective group; Hc.$NH_2$ and Hc'.$NH_2$ are respectively an amine thereof. $R^{2b}$ represents hydroxyl group or a lower alkoxy group. $R^3$, X, Y, and Z are as defined above.]

When there is no readily available candidate starting material, namely, the di-halogen-substituted nitrogen-containing six-membered ring compound having the substituents corresponding to the substituents ($R^3$, and when X, Y and Z are —$CR^7$= or —CH=, $R^7$ or hydrogen) on the nitrogen-containing six-membered ring of the target substance, the target substance can be produced by using a more readily available di-halogen-substituted nitrogen-containing six-membered ring compound for the starting material. More illustratively, an adequate substituent replacement reaction may be effected simultaneously with the halogen-amine replacement reaction by the substituted amino group. Exemplary useful substituent replacement reactions are the process wherein the halogen atom is replaced with amino group, and the amino group is further replaced with another halogen atom or cyano group by such reaction as Sandmeyer reaction of Schiemann reaction; the process wherein the halogen atom is replaced with hydroxyl group, and the hydroxyl group is further replaced with another halogen atom by using a phosphorus halide or a phosphorus oxyhalide; the process wherein the bromine atom or the chlorine atom is replaced with fluorine atom by using such reagent as potassium fluoride; the process wherein the halogen atom is replaced with hydrogen atom by hydrogenation; the process wherein the alkoxycarbonyl group or the acyl group is reduced into a lower alkyl group by using a hydride compound; the process wherein the carboxyl group is replaced with hydrogen atom by decarboxylation; and combination of the above-mentioned processes. It should be noted that, when the compound having the thus introduced amino group or hydroxyl group is subjected to a further substituent replacement reaction, protection of the amino group or the hydroxyl group is sometimes necessary. In such a case, the protection may be accomplished by phthalimidation in the case of the amino group, and by benzyloxidation in the case of the hydroxyl group. The protected group may be deprotected in the subsequent adequate stage. The halogen atom involved in the halogen-amine replacement reaction which is represented by Hal in the reaction scheme as shown above is not limited to any particular type. The halogen atom, however, is preferably fluorine atom with high reactivity. In such a case, if fluorine atom is present as a substituent in any of the highly reactive other sites, such site may be protected by replacing the fluorine atom with another halogen atom such as bromine atom or chlorine atom by the reactions as described above.

Alternatively, the starting compound (c) can be produced by reducing the nitro group into amino group by a normal process as shown in the following reaction scheme.

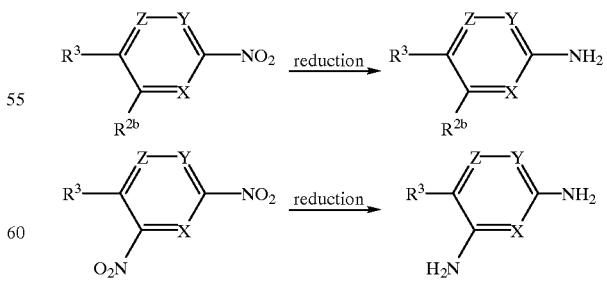

[In the formula, $R^{2b}$, $R^3$, X, Y and Z are as defined above.]

The thus obtained compound of the present invention is isolated and purified in accordance with a standard method. The compound is obtained in the form of a salt, a free carboxylic acid, or a free amine depending on the conditions of the isolation and the separation. The form of the compound, however, may be converted mutually, the compounds of the present invention can be prepared in desired form.

The compound represented by the general formula (1), above or the salt thereof may be formulated into an antibacterial composition with a pharmaceutically acceptable carrier adapted for parenteral administration such as injection, transrectal administration, or eye drop, or oral administration in solid or liquid form.

When the antibacterial composition of the present invention is in the form of an injection, it may be in the form of a solution, a suspension or an emulsion in a pharmaceutically acceptable sterilized water or a non-aqueous medium. Examples of appropriate non-aqueous carriers, diluents, media, and vehicles include propylene glycol, polyethylene glycol, vegetable oils such as olive oil, and organic esters adequate for injection such as ethyl oleate. Such composition may also contain additives such as a preservative, a wetting agent, an emulsifier and a dispersant. The composition may be sterilized, for example, by filtration through a bacteria-removing filter, or by incorporating a sterilizer in the form of a sterilizer or a sterile solid composition soluble in a sterilizable medium for injection just before its use.

A preparation for eye drop administration may preferably contain a solubilizer, a preservative, an isotonizing agent, a thickening agent, and the like in addition to the compound of the present invention.

Solid preparations for oral administration include capsules, tablets, pills, powders, and granules. In preparing such solid preparations, the compounds of the present invention are typically mixed with at least one inert diluent such as sucrose, lactose or starch. The preparation may also contain substances other than the inert diluents such as lubricant (for example, magnesium stearate etc.). In the case of capsules, tablets or pills, the preparation may also include a buffer. The tablets and the pills may have an enteric coating.

Liquid preparations for oral administration include pharmaceutically acceptable emulsions, solutions, suspensions, syrups and elixirs containing an inert diluent normally used in the art such as water. In addition to such inert diluent, the composition may also contain additives such as a wetting agent, an emulsifying agent, a suspending agent as well as a sweetener, a seasoning, and a flavor.

Preparations for enteral administrations may preferably contain an excipient such as cacao butter or suppository wax in addition to the compound of the present invention.

The dosage of the compound of the present invention varies depending on the nature of the compound administered, route of administration, the desired treatment period, and other factors. The compounds of the present invention, however, are typically administered at about 0.1 to 1000 mg/kg per day, and in particular, at about 0.5 to 100 mg/kg per day. If desired, such dose may be administered in 2 to 4 portions.

The novel pyridonecarboxylic acid derivatives and salts of the present invention exhibit very strong antibacterial actions as well as low phototoxicity and cytotoxicity, and therefore, would be widely applicable as pharmaceuticals for human and other animals as well as pharmaceuticals for fishes, pesticides, food preservatives, and the like. The compound of the present invention is also expected to exhibit antivirus properties, and especially, anti-HIV (human immunodeficiency virus) actions, and to be effective in preventing and treating AIDS.

Next, the present invention is described in further detail by referring to Examples and Reference Examples, which by no means limit the scope of the present invention.

REFERENCE EXAMPLE 1

Synthesis of 2-(t-butylamino)-3,5,6-trifluoropyridine

To 40 ml of acetonitrile were added 11.0 g of 2,3,5,6-tetrafluoropyridine and 18.5 g of t-butylamine, and the mixture was stirred at 60° C. for 3 days, and the solvent and the like were distilled off. To the residue was added 100 ml of chloroform, and the mixture was washed with 50 ml of distilled water. The chloroform layer was dried over anhydrous magnesium sulfate and concentrated under reduced pressure to obtain 9.7 g of the title compound as a pale yellow oil.

$^1$HNMR (CDCl$_3$) δ; 1.45 (s, 9H), 4.40 (brs, 1H), 7.16 (ddd, J=7 Hz, 8 Hz, 9 Hz, 1H);

REFERENCE EXAMPLE 2

Synthesis of 2-benzylamino-6-(t-butylamino)-3,5-difluoropyridine

To 20 ml of N-methylpyrrolidone were added 9.7 g of 2-(t-butylamino)-3,5,6-trifluoropyridine together with 15.5 g of benzylamine, and the mixture was stirred at 160° C. for one day and allowed to cool. After adding 50 ml of chloroform, the mixture was washed three times with 500 ml of distilled water. The chloroform layer was dried over anhydrous magnesium sulfate and concentrated under reduced pressure to obtain about 16.5 g of the title compound as a dark green oil.

REFERENCE EXAMPLE 3

Synthesis of 2-amino-6-(t-butylamino)-3,5-difluoropyridine

To 60 ml of methanol were added 10.7 g of the crude 2-benzylamino-6-(t-butylamino)-3,5-difluoropyridine as described above together with 1.10 g of 10% palladium carbon and 3.8 g of concentrated hydrochloric acid, and the mixture was hydrogenated for one day. The catalyst was separated by filtration, and the solvent and the like were distilled off under reduced pressure. To the residue was added 150 ml of chloroform, and the mixture was washed with 80 ml of 10% aqueous solution of sodium carbonate, and the washings were extracted again with 50 ml of chloroform. The chloroform layers were combined, and dried over anhydrous magnesium sulfate and concentrated under reduced pressure. The residue was subjected to chromatography (silica gel, 100 g; eluent: chloroform:n-hexane, 2:1, and then, chloroform) to obtain 3.3 g of the title compound as a pale brown oil.

$^1$HNMR (CDCl$_3$) δ; 1.43 (s, 9H), 4.11 (brs, 2H), 6.94 (t, J=10 Hz, 1H).

EXAMPLE 1

Synthesis of ethyl 1-[6-(t-butylamino)-3,5-difluoropyridin-2-yl]-8-chloro-6,7-difluoro-4-oxo-1,4-dihydroquinoline-3-carboxylate To 15 ml of chloroform solution of ethyl 3-ethoxy-2-(3-chloro-2,4,5-trifluorobenzoyl)acrylate prepared from 4.20 g of ethyl 3-chloro-2,4,5-trifluorobenzoylacetate by normal process was added 3.30 g of 2-amino-6-(t-butylamino)-3,5- difluoropyridine. The solution was concentrated under reduced pressure to obtain orange-colored solid residue. To this residue were added 4.0 g of annydrous potassium carbonate and 8 ml of N,N-dimethylformamide, and the mixture was stirred at 90° C. for 10 minutes and allowed to cool. The solution was separated by adding 50 ml of chloroform and 500 ml of distilled water, and the chloroform layer was washed twice with 500 ml of distilled water, dried over anhydrous magnesium sulfate, concentrated under reduced pressure, and allowed to stand. The precipitate was collected by filtration, washed with ethanol and diisopropylether successively to obtain 4.67 g of the title compound as a colorless powder.

Melting point: 203 to 205° C.; $^1$HNMR (CDCl$_3$) δ; 1.39 (s, 9H), 1.40 (t, J=7 Hz, 3H), 4.40 (q, J=7 Hz, 2H), 4.70 (brs, 1H), 7.21 (dd, J=8 Hz, 10 Hz, 1H), 8.31 (dd, J=8 Hz, 10H), 8.50 (s, 1H).

EXAMPLE 2

Synthesis of ethyl 8-bromo-1-[6-(t-butylamino)-3,5-difluoropyridin-2-yl]-6,7-difluoro-4-oxo-1,4-dihydroquinoline-3-carboxylate To 5 ml of chloroform solution of ethyl 3-ethoxy-2-(3-bromo-2,4,5-trifluorobenzoyl)acrylate prepared from 1.32 g of ethyl 3-bromo-2,4,5-trifluorobenzoylacetate by normal process was added 2-amino-6-(t-butylamino)-3,5-difluoropyridine until completion of the conversion into the aminoacrylate form was confirmed by monitoring the reaction by TLC. The solution was concentrated under reduced pressure to obtain yellow solid residue. To this residue were added 1.2 g of anhydrous potassium carbonate and 2 ml of N,N-dimethylformamide, and the mixture was stirred at 90° C. for 15 minutes and allowed to cool. The solution was separated by adding 30 ml of chloroform and 300 ml of distilled water, and the chloroform layer was washed twice with 300 ml of distilled water, dried over anhydrous magnesium sulfate, concentrated under reduced pressure, and allowed to stand. The precipitate was collected by filtration, washed with ethanol and diisopropylether successively to obtain 1.41 g of the title compound as a colorless powder.

Melting point: 198 to 203° C.; $^1$HNMR (CDCl$_3$) δ; 1.38 (s, 9H), 1.40 (t, J=7 Hz, 3H), 4.40 (q, J=7 Hz, 2H), 4.71 (brs, 1H), 7.20 (dd, J=8 Hz, 10 Hz, 1H), 8.36 (dd, J=9 Hz, 10H), 8.54 (s, 1H).

EXAMPLE 3

Synthesis of ethyl 1-[6-(t-butylamino)-3,5-difluoropyridin-2-yl]-6,7,8-trifluoro-4-oxo-1,4-dihydroquinoline-3-carboxylate To 1 ml chloroform solution of ethyl 3-ethoxy-2-(2,3,4,5-tetrafluorobenzoyl)acrylate prepared from 0.27 g of ethyl 2,3,4,5-tetrafluorobenzoylacetate by normal process was added 2-amino-6-(t-butylamino)-3,5-difluoropyridine until completion of the conversion into the aminoacrylate form was confirmed by monitoring the reaction by TLC. The solution was concentrated under reduced pressure. To the residue were added 0.6 g of anhydrous potassium carbonate and 1 ml of N,N-dimethylformamide, and the mixture was stirred at 90° C. for 15 minutes and allowed to cool. The solution was separated by adding 30 ml of chloroform and 300 ml of distilled water, and the chloroform layer was washed twice with 300 ml of distilled water, dried over anhydrous magnesium sulfate, concentrated under reduced pressure, and allowed to stand. The precipitate was collected by filtration, washed with ethanol and diisopropylether successively to obtain 0.15 g of the title compound as a colorless powder.

Melting point: 174 to 178° C.; $^1$HNMR (CDCl$_3$) δ; 1.40 (t, J=7 Hz, 3H), 1.42 (s, 9H), 4.40 (q, J=7 Hz, 2H), 4.71 (brs, 1H), 7.25 (dd, J=8 Hz, 10 Hz, 1H), 8.16 (ddd, J-2 Hz, .8 Hz, 10H), 8.48 (s, 1H).

EXAMPLE 4

Synthesis of ethyl 1-[6-(t-butylamino)-3,5-difluoropyridin-2-yl]-7-chloro-6-fluoro-4-oxo-1,4-dihydro-1,8-naphthylidine-3-carboxylate To 1 ml chloroform solution of ethyl 3-ethoxy-2-(2,6-dichloro-5-fluoronicotinoyl)acrylate prepared from 0.27 g of ethyl 2,6-dichloro-5-fluoronicotinoylacetate by normal process was added 2-amino-6-(t-butyl)amino-3,5-difluoropyridine until completion of the conversion into the aminoacrylate form was confirmed by monitoring the reaction by TLC. The solution was concentrated under reduced pressure. To the residue were added 0.5 g of anhydrous potassium carbonate and 1 ml of N,N-dimethylformamide, and the mixture was stirred at 90° C. for 15 minutes and allowed to cool. The solution was separated by adding 30 ml of chloroform and 300 ml of distilled water, and the chloroform layer was washed twice with 300 ml of distilled water, dried over anhydrous magnesium sulfate, concentrated under reduced pressure, and allowed to stand. The precipitate was collected by filtration, washed with ethanol and diisopropylether successively to obtain 0.19 g of the title compound as yellow crystals.

Melting point: 158 to 160° C.; $^1$HNMR (CDCl$_3$) δ; 1.39 (t, J=7 Hz, 3H), 1.45 (s, 9H), 4.40 (q, J=7 Hz, 2H), 4.68 (brs, 1H), 7.27 (t, J=9 Hz, 1H), 8.48 (d, J=7 Hz), 8.75 (s, 1H).

EXAMPLE 5

Synthesis of 1-(6-amino-3,5-difluoropyridin-2-yl)-8-chloro-6,7-difluoro-4-oxo-1,4-dihydroguionline-3-carboxylic acid To a mixed solution of 10 ml of 4N hydrochloric acid and 10 ml of acetic acid was added 4.10 g of ethyl 1-[6-(t-butylamino)-3,5-difluoropyridin-2-yl]-8-chloro-6,7-difluoro-4-oxo-1,4-dihydroquinoline-3-carboxylate, and the mixture was stirred under reflux condition for 5 hours. After adding 20 ml of distilled water, the solution was allowed to cool. The precipitate was collected by filtration, and washed with ethanol and diisopropylether successively to obtain 3.32 g of the title compound as a colorless powder.

Melting point: 280° C. or higher; $^1$HNMR (d$_6$-DMSO) δ; 6.80 (s, 2H), 7.99 (t, J=9 Hz, 1H), 8.38 (t, J=9 Hz, 1H), 8.93 (s, 1H).

REFERENCE EXAMPLE 4

Synthesis of 2-benzylamino-3,5,6-trifluoropyridine

To 50 ml of acetonitrile were added 12.0 g of 2,3,5,6-tetrafluoropyridine and 18.0 g of benzylamine, and the mixture was stirred under reflux condition for 2 hours, and the solvent and the like were distilled off. To the residue was added 150 ml of ethyl acetate, and the mixture was washed twice with 150 ml of distilled water and 150 ml of 10% aqueous solution of citric acid. The ethyl acetate layer was dried over anhydrous magnesium sulfate and concentrated under reduced pressure to obtain 16.0 g of the title compound as a pale yellow oil.

$^1$HNMR (CDCl$_3$) δ; 4.58 (d, J=6 Hz, 2H), 4.81 (brs, 1H), 7.23 (m, 1H), 7.35 (m, 5H).

REFERENCE EXAMPLE 5

Synthesis of 2-amino-3,5,6-trifluoropyridine

To 40 ml of methanol were added 7.60 g of the crude 2-benzylamino-3,5,6-trifluoropyridine as described above together with 0.55 g of 10% palladium on carbon and 2 ml acetic acid, and the mixture was hydrogenated at 50° C. for one day. The catalyst was separated by filtration, and the solvent and the like were distilled off under reduced pressure. The precipitate was dispersed in n-hexane, and collected by filtration to obtain 3.85 g of the title compound as a colorless solid.

$^1$HNMR (CDCl$_3$) δ; 4.53 (brs, 2H), 7.27 (m, 1H).

REFERENCE EXAMPLE 6

Synthesis of 2-amino-3,5-difluoro-6-(p-methoxybenzylamino)pyridine

To 10 ml of N-methylpyrrolidone were added 3.90 g of 2-amino-3,5,6-trifluoropyridine and 7.60 g of p-methoxybenzylamine, and the mixture was stirred under nitrogen atmosphere at 140° C. for one day and allowed to cool. To the solution was added 50 ml of chloroform, and the solution was washed three times with 500 ml of distilled water. The chloroform layer was dried over anhydrous magnesium sulfate and concentrated under reduced pressure, and the residue was subjected to chromatography (silica gel, 32 g; eluent: chloroform) to obtain 4.50 g of the title compound as a pale yellow crude oil.

$^1$HNMR (CDCl$_3$) δ; 3.80 (s, 3H), 4.18 (brs, 1H), 4.49 (brs, 3H), 6.87 (d, J=9 Hz, 2H), 6.99 (t, J=10 Hz, 1H), 7.28 (t, J=10 Hz, 2H).

EXAMPLE 6

Synthesis of ethyl 8-chloro-1-[3,5-difluoro-6-(p-methoxybenzylamino)pyridin-2-yl]-6,7-difluoro-4-oxo-1,4-dihydroquinoline-3-carboxylate To 18 ml of chloroform solution of ethyl 3-ethoxy-2-(3-chloro-2,4,5-trifluorobenzoyl)acrylate prepared from 2.52 g of ethyl 3-chloro-2,4,5-trifluorobenzoylacetate by normal process was added 2.65 g of 2-amino-3,5-difluoro-6-(p-methoxybenzylamino)pyridine. The solution was concentrated under reduced pressure, and to the residue were added 2.5 g of anhydrous potassium carbonate and 6 ml of N,N-dimethylformamide, and the mixture was stirred at 90° C. for 15 minutes and allowed to cool. The solution was separated by adding 50 ml of chloroform and 500 ml of distilled water, and the chloroform layer was washed twice with 500 ml of distilled water, dried over anhydrous magnesium sulfate, concentrated under reduced pressure, and allowed to stand. The precipitate was dispersed in ethanol, collected by filtration, and washed with ethanol to obtain 3.20 g of the title compound as a yellow powder.

Melting point: 197 to 200° C.; $^1$HNMR (CDCl$_3$) δ; 1.40 (t, J=7 Hz, 3H), 3.80 (s, 3H), 4.41 (q, J=7 Hz, 2H), 4.48 (m, 2H), 5.10 (brs, 1H), 6.83 (d, J=7 Hz, 2H), 7.20 (d, J=7 Hz, 2H), 7.25 (dd, J=8 Hz, 9 Hz, 1H), 8.31 (dd, J=8 Hz, 10 Hz, 1H), 8.47 (s, 1H).

EXAMPLE 7

Synthesis of 1-(6-amino-3,5-difluoropyridin-2-yl)-8-chloro-6,7-difluoro-4-oxo-1,4-dihydroquinoline-3-carboxylic acid To a mixed solution of 6 ml of 4N hydrochloric acid and 6 ml of acetic acid was added 3.00 g of ethyl 8-chloro-1-[3,5-difluoro-6-(p-methoxybenzylamino)pyridin-2-yl]-6,7-difluoro-4-oxo-1,4-dihydroquinoline-3-carboxylate, and the mixture was heated under reflux with stirring for 16 hours. The solution was allowed to cool and stand, and the precipitate was collected by decantation, and washed by adding a small amount of distilled water, shaking, allowing to stand, and decanting. To the precipitate was added 10 ml of ethanol, and the mixture was heated under reflux with stirring for 1 hour and allowed to cool and stand, and the precipitate was collected by decantation. To this precipitate was again added 10 ml of chloroform, and the mixture was stirred under reflux condition for 1 hour and allowed to cool, and the precipitate was collected by filtration and washed with ethanol and diisopropylether successively to obtain 1.25 g of the title compound as a pale brown powder.

EXAMPLE 8

Synthesis of 1-(6-amino-3,5-difluoropyridin-2-yl)-7-[(3S)-3-aminopyrrolidin-1-yl]-8-chloro-6-fluoro-4-oxo-1,4-dihydroquinoline-3-carboxylic acid To 250 mg of N,N-dimethylformamide were added 60 mg of 1-(6-amino-3,5-difluoropyridin-2-yl)-8-chloro-6,7-difluoro-4-oxo-1,4-dihydroquinoline-3-carboxylic acid and 60 mg of (3S)-3-aminopyrrolidine, and the mixture was heated under reflux with stirring at 90° C. for 1 hour. After adding 1 ml of ethanol, the mixture was allowed to cool, and the precipitate was collected by filtration and washed with ethanol and diisopropylether successively to obtain 41 mg of the title compound as a pale brown powder.

Melting point: 248 to 250° C. (decomposed); $^1$HNMR (d$_6$-DMSO) δ; 1.73 (m, 1H), 2.03 (m, 1H), 4.67 (m, 2H), 6.75 (brs, 2H), 7.95 (t, J=9 Hz, 1H), 7.98 (d, J=14 Hz, 1H), 8.73 (s, 1H); (Part of signals overlapped with the proton of water, and were undistinguishable.).

EXAMPLE 9

Synthesis of 7-(3-aminoazetidin-1-yl)-1-(6-amino-3,5-difluoropyridin-2-yl)-8-chloro-6-fluoro-4-oxo-1,4-dihydroquinoline-3-carboxylic acid To 350 mg of N,N-dimethylformamide were added 100 mg of 1-(6-amino-3,5-difluoropyridin-2-yl)-8-chloro-6,7-difluoro-4-oxo-1,4-dihydroquinoline-3-carboxylic acid, 80 mg of 3-aminoazetidine dihydrochloride and 150 mg of N-methylpyrrolidine, and the mixture was stirred at 90° C. for 1 hour. After adding 1 ml of ethanol, the mixture was allowed to cool, and the precipitate was collected by filtration and washed with ethanol and diisopropylether successively to obtain 86 mg of the title compound as a colorless powder.

Melting point: 260 to 263° C. (decomposed); $^1$HNMR (d$_6$-DMSO) δ; 3.73 (m, 1H), 4.09 (m, 2H), 4.67 (m, 2H), 6.74 (brs, 2H), 7.86 (d, J=14 Hz, 1H), 7.94 (t, J=9 Hz, 1H), 8.68 (s, 1H).

EXAMPLE 10

Synthesis of 1-(6-amino-3,5-difluoropyridin-2-yl)-8-chloro-6-fluoro-7-(3-methylaminoazetidin-1-yl)-4-oxo-1,4-dihydroguinoline-3-carboxylic acid To 400 mg of N,N-dimethylformamide were added 90 mg of 1-(6-amino-3,5-difluoropyridin-2-yl)-8-chloro-6,7-difluoro-4-oxo-1,4-dihydroquinoline-3-carboxylic acid, 80 mg of 3-methylaminoazetidine dihydrochloride, and 160 mg of N-methylpyrrolidine, and the mixture was stirred at 90°

C. for 1 hour. After adding 0.5 ml of ethanol, the mixture was allowed to cool, and the precipitate was collected by filtration and washed with ethanol and diisopropylether successively to obtain 92 mg of the title compound as a colorless powder.

Melting point: 259 to 265° C. (decomposed); $^1$HNMR ($d_6$-DMSO) δ; 2.20 (s, 3H), 3.48 (m, 1H), 4.14 (m, 2H), 4.64 (m, 2H), 6.75 (brs, 2H), 7.86 (d, J=14 Hz, 1H), 7.94 (t, J=9 Hz, 1H), 8.68 (s, 1H).

EXAMPLE 11

Synthesis of 1-(6-amino-3,5-difluoropyridin-2-yl)-7-(3-amino-3-methylazetidin-1-yl)-8-chloro-6-fluoro-4-oxo-1,4-dihydroquinoline-3-carboxylic acid To 350 mg of N,N-dimethylformamide were added 80 mg of 1-(6-amino-3,5-difluoropyridin-2-yl)-8-chloro-6,7-difluoro-4-oxo-1,4-dihydroquinoline-3-carboxylic acid, 60 mg of 3-amino-3-methylazetidine dihydrochloride, and 150 mg of N-methylpyrrolidine, and the mixture was stirred at 90° C. for 40 minutes. After adding 0.5 ml of ethanol, the mixture was allowed to cool, and the precipitate was collected by filtration and washed with ethanol to obtain 64 mg of the title compound as a pale yellow powder.

Melting point: 280° C. or higher; $^1$HNMR ($d_6$-DMSO) δ; 1.35(s, 3H), 4.19 (m, 2H), 4.30 (m, 2H), 6.75 (brs, 2H), 7.86 (d, J=14 Hz, 1H), 7.94 (t, J=9 Hz, 1H), 8.68 (s, 1H).

EXAMPLE 12

Synthesis of 3-hydroxyazetidine salt of 1-(6-amino-3,5-difluoropyridin-2-yl)-8-chloro-6-fluoro-7-(3-hydroxyazetidin-1-yl)-4-oxo-1,4-dihydroquinoline-3-carboxylic acid To 800 mg of acetonitrile were added 100 mg of 1-(6-amino-3,5-difluoropyridin-2-yl)-8-chloro-6,7-difluoro-4-oxo-1,4-dihydroquinoline-3-carboxylic acid, 60 mg of 3-hydroxyazetidine hydrochloride, and 150 mg of N-methylpyrrolidine, and the mixture was heated under reflux for 1 hour. The precipitate was collected by filtration and washed with ethanol and diisopropylether successively to obtain 56 mg of the title compound as a colorless powder.

Melting point: 185 to 190° C. (decomposed); $^1$HNMR (d6-DMSO) δ; 3.45 (m, 2H), 3.65 (m, 2H), 4.14 (m, 2H), 4.39 (m, 1H), 4.46 (m, 1H), 4.68 (m, 2H), 6.70 (brs, 2H), 7.80 (d, J=14 Hz, 1H), 7.91 (t, J=9 Hz, 1H), 8.52 (s, 1H).

EXAMPLE 13

Synthesis of N-methylpyrrolidine salt of 1-(6-amino-3,5-difluoropyridin-2-yl)-8-chloro-6-fluoro-7-(3-hydroxyazetidin-1-yl)-4-oxo-1,4-dihydroquinoline-3-carboxylic acid To 2000 mg of N,N-dimethylformamide were added 300 mg of 1-(6-amino-3,5-difluoropyridin-2-yl)-8-chloro-6,7-difluoro-4-oxo-1,4-dihydroquinoline-3-carboxylic acid, 110 mg of 3-hydroxyazetidine hydrochloride, and 300 mg of N-methylpyrrolidine, and the mixture was stirred at 80° C. for 10 hours. After adding 2 ml of ethanol, the mixture was allowed to cool, and the precipitate was collected by filtration and washed with ethanol and diisopropylether successively to obtain 222 mg of the title compound as a colorless powder.

Melting point: 234 to 238° C. (decomposed); $^1$HNMR ($d_6$-DMSO) δ; 1.67 (m, 4H), 2.24 (s, 1H), 2.38 (m, 4H), 4.18 (m, 2H), 4.47 (m, 1H), 4.71 (m, 2H), 5.73 (m, 1H), 6.75 (brs, 2H), 7.86 (d, J=14 Hz, 1H), 7.94 (t, J=9 Hz, 1H), 8.67 (s, 1H).

EXAMPLE 14

Synthesis of 1-(6-amino-3,5-difluoropyridin-2-yl)-8-chloro-6-fluoro-4-oxo-7-piperazino-1,4-dihydroquinoline-3-carboxylic acid To 170 mg of N,N-dimethylformamide were added 50 mg of 1-(6-amino-3,5-difluoropyridin-2-yl)-8-chloro- 6,7-difluoro-4-oxo-1,4-dihydroquinoline-3-carboxylic acid, 50 mg of piperazine, and the mixture was stirred at 90° C. for 1 hour. After adding about 0.3 ml of ethanol, the mixture was allowed to cool, and the precipitate was collected by filtration and washed with ethanol and diisopropylether successively-to obtain 33 mg of the title compound as a colorless powder.

Melting point: 273 to 277° C. (decomposed); $^1$HNMR ($d_6$-DMSO) δ; 2.82 (m, 4H), 3.16 (m, 4H), 6.76 (brs, 2H), 7.95 (t, J=9 Hz, 1H), 8.05 (d, J=12 Hz, 1H), 8.79 (s, 1H).

REFERENCE EXAMPLE 7

Synthesis of 3,5,6-trifluoro-2-(methylamino) pyridine

To 10 ml of acetonitrile were added 4.5 g of 2,3,5,6-tetrafluoropyridine and 10 ml of methylamine (10% aqueous solution), and the mixture was stirred at 50° C. for 2 hours. To the solution was added 50 ml of chloroform, and the mixture was washed four times with 250 ml of distilled water. The chloroform layer was dried over anhydrous magnesium sulfate and concentrated under reduced pressure to obtain the title compound as a pale brown crude oil.

$^1$HNMR (CDCl$_3$) δ; 2.99 (d, J=5 Hz, 3H), 4.53 (brs, 1H), 7.20 (ddd, J=7 Hz, 8 Hz, 9 Hz, 1H).

REFERENCE EXAMPLE 8

Synthesis of 2-benzylamino-3,5-difluoro-6-(methylamino)pyridine

To 20 ml of N-methylpyrrolidone were added all amount of the above-described 3,5,6-trifluoro-2-(methylamino)-pyridine together with 10 g of benzylamine, and the mixture was stirred at 140° C. for 19 hours and allowed to cool. To the solution was added 50 ml of chloroform and the mixture was washed six times with 200 ml of distilled water. The chloroform layer was dried over anhydrous magnesium sulfate and concentrated under reduced pressure to obtain the title compound as a crude oil.

REFERENCE EXAMPLE 9

Synthesis of 2-amino-3,5-difluoro-6-(methylamino) pyridine

To a mixed solution of 10 ml of methanol and 1 ml of concentrated hydrochloric acid were added all amount of the above described 2-benzylamino-3,5-difluoro-6-(methylamino)pyridine together with 0.55 g of 10% palladium on carbon, and the mixture was hydrogenated at 50° C. overnight. The catalyst was separated by filtration, and the solvent and the like were distilled off under reduced pressure. To the residue was added 50 ml of chloroform, and the mixture was washed with 50 ml of 5% aqueous solution of sodium carbonate. The chloroform layer was dried over anhydrous magnesium sulfate and concentrated under reduced pressure. The solid precipitate was collected by filtration to obtain 840 mg of the title compound as a pale gray solid.

$^1$HNMR (CDCl$_3$) δ; 2.95 (d, J=5 Hz, 3H), 4.19 (brs, 3H), 6.98 (t, J=10 Hz, 1H).

EXAMPLE 15

Synthesis of ethyl 8-chloro-6,7-difluoro-1-(3,5-difluoro-6-methylaminopyridin-2-yl)-4-oxo-1,4-dihydroquinoline-3-carboxylate To 5 ml of chloroform solution of ethyl 3-ethoxy-2-(3-chloro-2,4,5-trifluorobenzoyl)acrylate prepared from 0.70 g of ethyl 3-chloro-2,4,5-trifluorobenzoylacetate by normal process was added 430 mg of 2-amino-3,5-difluoro-6-(methylamino)pyridine. The solution was concentrated under reduced pressure. To the residue were added 0.3 g of anhydrous potassium carbonate and 2 ml of N,N-dimethylformamide, and the mixture was stirred at 90° C. for 10 minutes and allowed to cool. The solution was separated by adding 30 ml of chloroform and 300 ml of distilled water, and the chloroform layer was washed twice with 300 ml distilled water, dried over anhydrous magnesium sulfate, concentrated under reduced pressure, and allowed to stand. The precipitate was collected by filtration, washed with ethanol and diisopropylether successively to obtain 784 mg of the title compound as a colorless powder.

Melting point: 207 to 209° C.; $^1$HNMR (CDCl$_3$) δ; 1.41 (t, J=7 Hz, 3H), 2.98 (d, J=5 Hz, 3H), 4.41 (q, J=7 Hz, 2H), 4.85 (brs, 1H), 7.23 (dd, J=8 Hz, 9 Hz, 1H), 8.32 (dd, J=8 Hz, 10 Hz, 1H), 8.50 (s, 1H).

EXAMPLE 16

Synthesis of 8-chloro-6,7-difluoro-1-(3,5-difluoro-6-methylaminopyridin-2-yl)-4-oxo-1,4-dihydroquinoline-3-carboxylic acid To 3 ml of a mixed solution (1:1, v/v) of 4 ml of 4N hydrochloric acid and 1 ml of acetic acid was added 510 mg of ethyl 8-chloro-6,7-difluoro-1-(3,5-difluoro-6-methylamino-pyridin-2-yl)-4-oxo-1,4-dihydroquinoline-3-carboxylate, and the mixture was heated under reflux with stirring for 2.5 hours. After adding 2 ml of distilled water, the mixture was allowed to cool, and the precipitate was collected by filtration and washed with ethanol and diisopropylether successively to obtain 454 mg of the title compound as a gray powder.

Melting point: 236 to 242° C.; $^1$HNMR (d$_6$-DMSO) δ; 2.67 (d, J=5 Hz, 3H), 5.94 (brs, 1H), 7.06 (t, J=8 Hz, 1H), 7.45 (dd, J=10 Hz, 12 Hz, 1H), 8.41 (dd, J=9 Hz, 10 Hz, 1H), 8.72 (s, 1H).

EXAMPLE 17

Synthesis of 7-(3-aminoazetidine-1-yl)-8-chloro-6-fluoro-1-(3,5-difluoro-6-methylaminopyridine-2-yl)-4-oxo-1,4-dihydroquinoline-3-carboxylic acid To 400 mg of N,N-dimethylformamide were added 100 mg of 8-chloro-6,7-difluoro-1-(3,5-difluoro-6-methylaminopyridine-2-yl)-4-oxo-1,4-dihydroquinoline-3-carboxylic acid, 60 mg of 3-aminoazetidine dihydrochloride, and 120 mg of N-methylpyrrolidine, and the mixture was stirred at 100° C. for 1 hour. After adding 0.5 ml of ethanol, the mixture was allowed to cool, and the precipitate was collected by filtration and washed with ethanol and diisopropylether successively to obtain 102 mg of the title compound as a colorless powder.

Melting point: 222 to 227° C. (decomposed); $^1$HNMR (d$_6$-DMSO) δ; 2.77 (d, J=5 Hz, 3H), 3.75 (m, 1H), 4.07 (m, 2H), 4.67 (m, 2H), 7.19 (brs, 1H), 7.88 (d, J=14 Hz, 1H), 7.95 (t, J=7 Hz, 1H), 8.70 (s, 1H).

REFERENCE EXAMPLE 10

Synthesis of 2-benzylamino-3,5,6-trifluoro-4-methylpyridine

To 2 ml of N-methylpyrrolidone were added 1.65 g of 2,3,5,6-tetrafluoro-4-methylpyridine and 2.30 g of benzylamine, and the mixture was stirred at 80° C. for 2 hours and allowed to cool. After adding 25 ml of chloroform, the mixture was washed three times with 300 ml of distilled water. The chloroform layer was dried over anhydrous magnesium sulfate and concentrated under reduced pressure to obtain the title compound in crude form.

REFERENCE EXAMPLE 11

Synthesis of 2-amino-3,5,6-trifluoro-4-methylpyridine

To 4 ml of methanol were added all amount of the crude 2-benzylamino-3,5,6-trifluoro-4-methylpyridine as described above together with 0.18 g of 10% palladium on carbon and 2 ml of acetic acid, and the mixture was hydrogenated at 50° C. for one day. The catalyst was separated by filtration, and the solvent and the like were distilled off under reduced pressure to obtain 1.35 g of the title compound as a colorless solid.

$^1$HNMR (CDCl$_3$) δ; 2.26 (t, J=2 Hz, 3H), 4.40 (brs, 2H).

REFERENCE EXAMPLE 12

Synthesis of 2-amino-3,5-difluoro-6-(p-methoxybenzylamino)-4-methylpyridine

To 3 ml of N-methylpyrrolidone were added 1.35 g of 2-amino-3,5,6-trifluoro-4-methylpyridine together with 3.0 g of p-methoxybenzylamine, and the mixture was stirred under nitrogen atmosphere at 140° C. for 18 hours and allowed to cool. After adding 30 ml of chloroform, the mixture was washed three times with 300 ml of distilled water. The chloroform layer was dried over anhydrous magnesium sulfate and concentrated under reduced pressure. The residue was subjected to chromatography (silica gel, 20 g; eluent: chloroform:n-hexane, 1:1, and then, chloroform) to obtain 0.90 g of the title compound as a pale yellow crude oil.

$^1$HNMR (CDCl$_3$) δ; 2.15 (t, J=2 Hz, 3H), 3.80 (s, 3H), 4.11 (brs, 2H), 4.41 (brs, 1H), 4.48 (m, 2H), 6.87 (d, J=8 Hz, 2H), 7.27 (d, J=8 Hz, 2H).

EXAMPLE 18

Synthesis of ethyl 8-chloro-1-[3,5-difluoro-6-(p-methoxybenzylamino)-4-methylpyridine-2-yl]-6,7-difluoro-4-oxo-1,4-dihydroquinoline-3-carboxylate To 3 ml chloroform solution of ethyl 3-ethoxy-2-(3-chloro-2,4,5-trifluorobenzoyl)acrylate prepared from 0.78 g of ethyl 3-chloro-2,4,5-trifluorobenzoylacetate by normal process was added 0.90 g of 2-amino-3,5-difluoro-6-(p-methoxybenzylamino)-4-methylpyridine. The solution was concentrated under reduced pressure, and to the residue were added 1.3 g of anhydrous potassium carbonate and 3 ml of N,N-dimethylformamide, and the mixture was stirred at 90° C. for 15 minutes and allowed to cool. The solution was separated by adding 30 ml of chloroform and 300 ml of distilled water, and the chloroform layer was washed twice with 300 ml of distilled water, dried over anhydrous magnesium sulfate, and concentrated under reduced pressure to obtain the title compound as a brown crude oil.

EXAMPLE 19

Synthesis of 1-(6-amino-3,5-difluoro-4-methylpyridine-2-yl)-8-chloro-6,7-difluoro-4-oxo-1,4-dihydroquinoline-3-carboxylic acid To a mixed solution of 2.5 ml of 4N hydrochloric acid and 2.5 ml of acetic acid was added all amount of the above described ethyl 8-chloro-1-[3,5-difluoro-6-(p-methoxybenzylamino)-4-methylpyridine-2-yl]-6,7-difluoro-4-oxo-1,4-dihydroquinoline-3-carboxylate, and the mixture was heated under reflux with stirring for 3 hours and allowed to cool and stand. To the residue was added 10 ml of distilled water, and the solution was concentrated under reduced pressure. The procedure of adding 10 ml of ethanol and concentrating the solution under reduced pressure was repeated three times, and 6 ml of chloroform was added to the residue, and the mixture was heated under reflux with stirring for 1 hour and allowed to cool. The precipitate was collected by filtration, and washed with ethanol and diisopropylether successively to obtain 128 mg of the title compound as a colorless powder.

Melting point: 253 to 257° C. $^1$HNMR ($d_6$-DMSO) δ; 2.24 (s, 3H), 6.67 (brs, 2H), 8.38 (t, J=9 Hz, 1H), 8.89 (s, 1H).

EXAMPLE 20

Synthesis of 7-(3-aminoazetidine-1-yl)-1-(6-amino-3,5-difluoro-4-methylpyridine-2-yl)-8-chloro-6-fluoro-4-oxo-1,4-dihydrogtinoline-3-carboxylic acid To 280 mg of N,N-dimethylformamide were added 50 mg of 1-(6-amino-3,5-difluoro-4-methylpyridine-2-yl)-8-chloro-6,7-difluoro-4-oxo-1,4-dihydroquinoline-3-carboxylic acid, 40 mg of 3-aminoazetidine dihydrochloride, and 120 mg of N-methylpyrrolidine, and the mixture was stirred at 90° C. for 1 hour. After adding 0.4 ml of ethanol, the mixture was allowed to cool. The precipitate was collected by filtration, and washed with ethanol and diisopropylether successively to obtain 45 mg of the title compound as a colorless powder.

Melting point: 243 to 245° C. (decomposed); $^1$HNMR ($d_6$-DMSO) δ; 2.23 (s, 3H), 3.71 (m, 1H), 4.05 (m, 2H), 4.67 (m, 2H), 6.60 (brs, 2H), 7.85 (d, J=14 Hz, 1H), 8.64 (s, 1H).

REFERENCE EXAMPLE 13

Synthesis of 4-(t-butylamino)-2,3,5,6-tetrafluoropyridine

To 100 ml of acetonitrile was added 24.5 g of pentafluoropyridine, and the mixture was stirred in an ice bath simultaneously with the dropwise addition of 30 g of t-butylamine. When the mixture warmed to room temperature, 150 ml of chloroform was added, and the mixture was washed twice with 800 ml of distilled water. The chloroform layer was dried over anhydrous magnesium sulfate and concentrated under reduced pressure to obtain 23 g of the title compound as a pale yellow oil.

REFERENCE EXAMPLE 14

Synthesis of 2-benzylamino-4-(t-butylamino)-3,5,6-trifluoropyridine

To 10 ml of N-methylpyrrolidone were added 6.8 g of 4-(t-butylamino)-2,3,5,6-tetrafluoropyridine together with 7.2 g of benzylamine, and the mixture was stirred at 115° C. for one day and allowed to cool. After adding 40 ml of chloroform, the mixture was washed three times with 400 ml of distilled water. The chloroform layer was dried over anhydrous magnesium sulfate and concentrated under reduced pressure to obtain about 8.0 g of the title compound as a dark green crude oil.

$^1$HNMR (CDCl$_3$) δ; 1.39 (s, 9H), 4.16 (brs, 1H), 4.55 (brs, 2H), 4.48 (m, 2H), 7.35 (m, 5H).

REFERENCE EXAMPLE 15

Synthesis of 2-amino-4-(t-butylamino)-3,5,6-trifluoropyridine

To 13 ml of acetic acid were added 4.0 g of the crude 2-benzylamino-4-(t-butyl)amino-3,5,6-trifluoropyridine as described above together with 0.43 g of 10% palladium on carbon, and the mixture was hydrogenated at 60° C. for 6 hours. The catalyst was separated by filtration, and the solvent and the like were distilled off under reduced pressure to-obtain the title compound as a brown crude oil.

REFERENCE EXAMPLE 16

Synthesis of ethyl 3-r (4-t-butylamino-3,5,6-pyridine-2-yl)aminol-2-(3-chloro-2,4,5-trifluorophenyl)acrylate To 1.4 g of ethyl 3-chloro-2,4,5-trifluorobenzoyl-acetate were added 1.5 g of acetic anhydride and 1.5 g of triethyl orthoformate, and the mixture was heated under reflux for 2 hours. The solvent was distilled off, and toluene was added to the residue for azeotropic distillation. 3 ml of chloroform was added to the half of the residue, and 5 ml of chloroform solution of 1 g of 2-amino-3,5,6-trifluoro-4-(t-butylamino) pyridine was added dropwise to the mixture with an ice cooling, then the mixture was stirred at room temperature for 2 hours. The solvent was distilled off, and the solid precipitate was collected by filtration and washed with diethylether to obtain 1.14 g of the title compound.

EXAMPLE 21

Synthesis of ethyl 1-(4-t-butylamino-3,5,6-trifluoropyridine-2-yl)-8-chloro-6,7-difluoro-4-oxo-1,4-dihydroquinoline-3-carboxylate To 6 ml of N,N-dimethyl-formamide solution of 1.14 g of ethyl 3-[(4-t-butylamino-3,5,6-pyridine-2-yl)amino]-2-(3-chloro-2,4,5-trifluorophenyl)acrylate was added 700 mg of potassium carbonate, and the mixture was stirred at room temperature for 3.5 hours. The reaction solution was poured into ice water, and ethyl acetate was added for extraction. The organic layer was separated and dried over magnesium sulfate, and solvent was distilled off. The solid content was collected by filtration to obtain 1.25 g of the title compound as a colorless powder.

Melting point: 145 to 146° C.; $^1$HNMR (CDCl$_3$) δ; 1.40 (t, J=7 Hz, 3H), 1.48 (s, 9H), 4.41 (q, J=7 Hz, 2H), 4.78 (1H, brs), 8.31 (t, J=9 Hz, 1H), 8.44 (1H, s).

EXAMPLE 22

Synthesis of 1-(4-amino-3,5,6-trifluoropyridine-2-yl)-8-chloro-6,7-difluoro-4-oxo-1,4-dihydroquinoline-3-carboxylic acid To 300 mg of ethyl 1-(4-t-butylamino-3,5,6-trifluoropyridine-2-yl)-8-chloro-6,7-difluoro-4-oxo-1,4- dihydroquinoline-3-carboxylate were added 3 ml of 12N hydrochloric acid and 0.5 ml of acetic acid, and the mixture was heated under reflux for 1.5 hour. The reaction solution was allowed to cool, and the solid precipitated was collected by filtration and washed with ethanol and diethylether successively to obtain 168 mg of the title compound as a colorless powder.

Melting point: 280 to 283° C. $^1$HNMR (d$_6$-DMSO) δ; 7.54 (s, 1H), 8.38 (dd, J=9 Hz, 10 Hz, 1H), 8.98 (s, 1H).

EXAMPLE 23

Synthesis of 7-(3-aminoazetidine-1-yl)-1-(4-amino-3,5,6-trifluoropyridine-2-yl)-8-chloro-6-fluoro-4-oxo-1,4-dihydroquinoline-3-carboxylic acid To 1 ml dimethylsulfoxide solution of 70 mg of 3-aminoazetidine dihydrochloride and 250 mg of triethylamine at 80° C. was added 150 mg of 1-(4-amino-3,5,6-trifluoropyridine-2-yl)-8-chloro-6,7-difluoro-4-oxo-1,4-dihydroquinoline-3-carboxylic acid with stirring, and the mixture was stirred at 80° C. for 1 hour. The reaction solution was allowed to cool and decanted with diethylether. Ethanol was added to the residue to disperse the solid content, and the solid content was collected by filtration, washed with ethanol, and dried to obtain 85 mg of the title compound as a pale yellow powder.

Melting point: decomposed at 230° C. or higher; $^1$HNMR (d$_6$-DMSO+TFA) δ; 4.05 (m, 1H), 4.45 (m, 2H), 4.77 (m, 2H), 7.50 (2H, brs), 7.93 (d, J=14 Hz, 1H), 8.32 (brs, 2H), 8.80 (s, 1H).

REFERENCE EXAMPLE 17

Synthesis of 3,5-diamino-2-chloropyridine

The mixture of 2.19 g of iron powder, 5 ml of water, and 10 ml of ethanol was stirred at 80° C. for 2 minutes. After incremental addition of 1 ml concentrated hydrochloric acid, the mixture was stirred at the same temperature until the solution became neutral. To the reaction solution was incrementally added suspension of 1 g 2-chloro-3,5-dinitropyridine in 5 ml ethanol, and the mixture was stirred at 80° C. for 40 minutes. The reaction solution was allowed to cool, and the iron was removed by filtration with celite, and the solvent of the filtrate was distilled off. Ethanol was added to the residue to disperse the solid content, and the solid content was collected by filtration to obtain 360 mg of the title compound.

REFERENCE EXAMPLE 18

Synthesis of ethyl 3-[(5-amino-6-chloropyridine-3-yl)aminol-2-(3-chloro-2,4,5-trifluorophenyl)acrylate To 1.4 g of ethyl 3-chloro-2,4,5-trifluorobenzoylacetate were added 1.5 g of acetic anhydride and 1.5 g of triethyl orthoformate, and the mixture was heated under reflux for 2 hours. The solvent was distilled off, and toluene was added to the residue for azeotropic distillation. 3 ml of chloroform was added to the half of the residue, and a solution of 360 mg of 3,5-diamino-2-chloropyridine in 3 ml ethanol was added dropwise to the mixture at room temperature and the mixture was stirred at room temperature for 30 minutes. The solvent was distilled off, and the residue was purified by column chromatography to obtain 200 mg of the title compound.

EXAMPLE 24

Synthesis of ethyl 1-(5-amino-6-chloropyridine-3-yl)-8-chloro-6,7-difluoro-4-oxo-1,4-dihydroquinoline-3-carboxylate To a solution of 180 mg ethyl 3-[(5-amino-6-chloropyridine-3-yl)amino]-2-(3-chloro-2,4,5-trifluorophenyl)acrylate in 3 ml N,N-dimethylformamide was added 57 mg of potassium carbonate, and the mixture was stirred at room temperature for 2 hours. The reaction solution was poured into ice water, and extracted by adding ethyl acetate. The organic layer was separated and dried over magnesium sulfate, and the solvent was distilled off. The solid content was collected by filtration to obtain 125 mg of the title compound as a pale yellow powder.

Melting point: 233 to 236° C.; $^1$HNMR (CDCl$_3$) δ; 1.39 (t, J=7 Hz, 3H), 4.40 (q, J=7 Hz, 2H), 4.46 (brs, 2H), 7.04 (s, 1H), 7.26 (s, 1H), 7.86 (s, 1H), 8.32 (t, J=9 Hz, 1H), 8.37 (s, 1H).

EXAMPLE 25

Synthesis of 1-(5-amino-6-chloropyridine-3-yl)-8-chloro-6,7-difluoro-4-oxo-1,4-dihydroquinoline-3-carboxylic acid To 100 mg of ethyl 1-(5-amino-6-chloropyridine-3-yl)-8-chloro-6,7-difluoro-4-oxo-1,4-dihydroquinoline-3-carboxylate was added 3 ml of concentrated hydrochloric acid, and the mixture was heated under reflux for 2 hours. The reaction solution was allowed to cool, and the solid precipitated was collected by filtration. The solid was washed with ethanol to obtain 86 mg of the title compound as a pale yellow powder.

Melting point: 277 to 281° C.; $^1$HNMR (d$_6$-DMSO) δ; 7.37 (s, 1H), 7.86 (s, 1H), 8.41 (t, J=9 Hz, 1H), 8.69 (s, 1H).

EXAMPLE 26

Synthesis of 7-(3-aminoazetidine-1-yl)-1-(5-amino-6-chloropyridine-3-yl)-8-chloro-6-fluoro-4-oxo-1,4-dihydroquinoline-3-carboxylic acid To dimethylsulfoxide solution 1 ml of 53 mg of 3-aminoazetidine dihydrochloride and 146 mg of triethylamine at 80° C. was added 80 mg of 1-(5-amino-6-chloropyridine-3-yl)-8-chloro-6,7-difluoro-4-oxo-1,4-dihydroquinoline- 3-carboxylic acid with stirring, and the mixture was stirred at 80° C. for 1 hour. The reaction solution was allowed to cool and decanted with diethylether. Ethanol was added to the residue to disperse the solid content, and the solid content was collected by filtration, washed with ethanol, and dried to obtain 45 mg of the title compound as a pale yellow powder.

Melting point: 280° C. or higher; $^1$HNMR (d$_6$-DMSO) δ; 3.78 (m, 1H), 4.14 (m, 2H), 4.64 (m, 2H), 6.04 (br, 2H), 7.30 (s, 1H), 7.75 (s, 1H), 7.89 (d, J=14 Hz, 1H), 8.49 (s, 1H).

REFERENCE EXAMPLE 19

Synthesis of 2,4-dichloro-5-fluoropyrimidine 25.3 g of 5-fluorouracil was fully mixed with 72.9 of phosphor pentachloride, and the mixture was gradually heated to 130° C. and reacted for 4 hours. (The reaction mixture became liquid in about 1 hour, and the reaction proceeded at a high rate.) After adding 300 ml of ice water and 200 ml of chloroform, the mixture was stirred for 20 minutes. The insoluble content was separated by filtration with celite, and the filtrate was separated. The chloroform layer was washed with 5% aqueous solution of sodium carbonate, dried over anhydrous magnesium sulfate, and concentrated under reduced pressure to obtain 30.6 g of the title compound as a brown oil (which crystallized at a lower temperature).

$^1$HNMR (CDCl$_3$) δ; 8.49 (s, 1H).

REFERENCE EXAMPLE 20

Synthesis of 4-(t-butylamino)-2-chloro-5-fluoropyrimidine

To 20 ml of acetonitrile were added 6.4 g of 2,4-dichloro-5-fluoropyrimidine and 7.0 g of t-butylamine, then the mixture was stirred at 50° C. for 20 minutes. The solution was concentrated under reduced pressure, and separated by adding 40 ml of distilled water and 70 ml of chloroform. The chloroform layer was dried over anhydrous magnesium sulfate and concentrated under reduced pressure. The precipitated pale yellow crystals were dispersed in diisopropylether and collected by filtration to obtain 4.1 g of the title compound.

$^1$HNMR (CDCl$_3$) δ; 1.51 (s, 9H), 5.07 (brs, 1H), 7.83 (d, J=3 Hz, 1H).

REFERENCE EXAMPLE 21

Synthesis of 2-benzylamino-4-(t-butylamino)-5-fluoropyrimidine

To 5 ml of N-methylpyrrolidone were added 1.8 g of 4-(t-butylamino)-2-chloro-5-fluoropyrimidine and 4.0 g of benzylamine, and the mixture was stirred at 140° C. for 17 hours and separated by adding 300 ml of distilled water and 40 ml of chloroform. The chloroform layer was washed twice with 300 ml of distilled water, dried over anhydrous magnesium sulfate and concentrated under reduced pressure. The precipitated pale yellow crystals were dispersed in diisopropylether and collected by filtration to obtain 1.9 g of the title compound.

$^1$HNMR (CDCl$_3$) δ; 1.40 (s, 9H), 4.54 (d, J=6 Hz, 2H), 4.71 (brs, 1H), 5.06 (brs, 1H), 7.33 (m, 5H), 7.65 (d, J=3 Hz, 1H).

REFERENCE EXAMPLE 22

Synthesis of 2-amino-4-(t-butylamino)-5-fluoropyrimidine

To 8 ml of acetic acid were added 1.00 g of 2-benzylamino-4-(t-butylamino)-5-fluoropyrimidine together with 215 mg of 10% palladium on carbon, and the mixture was hydrogenated at 60° C. for ten days. The catalyst was separated by filtration, and the solvent and the like were distilled off under reduced pressure. The procedure of adding 10 ml of ethanol and concentrating under reduced pressure was repeated three times, and the residue was separated by column chromatography (silica gel, 25 g; eluent: chloroform, and then, chloroform:methanol, 200:1), and the corresponding fractions were collected and concentrated under reduced pressure to obtain 360 mg of the title compound as a pale gray solid.

$^1$HNMR (CDCl$_3$) δ; 1.47 (s, 9H), 4.92 (brs, 1H), 5.57 (brs, 2H), 7.51 (d, J=3 Hz, 1H).

EXAMPLE 27

Synthesis of ethyl 1-f4-(t-butylamino)-5-fluoropyrimidine-2-yll-8-chloro-6,7-difluoro-4-oxo-1,4-dihydroquinoline-3-carboxylate To 3 ml of chloroform solution of ethyl 3-ethoxy-2-(3-chloro-2,4,5-trifluorobenzoyl)acrylate prepared from 210 mg of ethyl 3-chloro-2,4,5-trifluorobenzoylacetate by normal process was added 340 mg of 2-amino-4-(t-butylamino)-5-fluoropyrimidine. The solution was concentrated under reduced pressure. To the residue were added 550 mg of anhydrous potassium carbonate and 2 ml of N,N-dimethylformamide, and the mixture was stirred at 90° C. for 1 hour and 10 minutes and allowed to cool. The solution was separated by adding 30 ml of chloroform and 300 ml of distilled water, and the chloroform layer was washed twice with 300 ml of distilled water, dried over anhydrous magnesium sulfate, and concentrated under reduced pressure. The residue was separated by column chromatography (silica gel, 16 g; eluent: chloroform:methanol, 200:1), and the corresponding fractions were collected and concentrated under reduced pressure. To the residue was added 0.5 ml of ethanol, and the precipitate was collected by filtration and washed with ethanol and diisopropylether successively to obtain 98 mg of the title compound as a colorless powder.

Melting point: 201 to 205° C.; $^1$HNMR (CDCl$_3$) δ; 1.38 (t, J=7 Hz, 3H), 1.43 (s, 9H), 4.39 (q, J=7 Hz, 2H), 5.30 (brs, 1H), 8.02 (d, J=3 Hz, 1H), 8.24 (t, J=9 Hz, 1H), 8.90 (s, 1H).

EXAMPLE 28

Synthesis of 1-(4-amino-5-fluoropyrimidine-2-yl)-8-chloro-6,7-difluoro-4-oxo-1,4-dihydroguinoline-3-carboxylic acid To a mixed solution (1:1, v/v) of 0.4 ml of 4N hydrochloric acid and 1 ml of acetic acid was added 90 mg of ethyl 1-[4-(t-butylamino)-5-fluoropyrimidine-2-yl]-8-chloro-6,7-difluoro-4-oxo-1,4-dihydroquinoline-3-carboxylate, and the mixture was heated under reflux with stirring for 3 and half hours and allowed to cool. The precipitate was collected by filtration, and washed with ethanol and diisopropylether successively to obtain 48 mg of the title compound as a colorless powder.

Melting point: 242 to 246° C.; $^1$HNMR (d$_6$-DMSO) δ; 8.04 (brs, 2H), 8.33 (d, J=3 Hz, 1H), 8.34 (t, J=9 Hz, 1H), 9.02 (s, 1H).

EXAMPLE 29

Synthesis of 7-(3-aminoazetidine-1-yl)-1-(4-amino-5-fluoropyrimidine-2-yl)-8-chloro-6-fluoro-4-oxo-1,4-dihydroquinoline-3-carboxylic acid To 100 mg of N,N-dimethylformamide were added 25 mg of 1-(4-amino-5-fluoropyrimidine-2-yl)-8-chloro-6,7-difluoro-4-oxo-1,4-dihydroquinoline-3-carboxylic acid, 20 mg of 3-aminoazetidine dihydrochloride, and 50 mg of N-methylpyrrolidine, and the mixture was stirred at 90° C. for 1 hour. After adding 0.2 ml of ethanol, the mixture was allowed to cool, and the precipitate was collected by filtration and washed with ethanol and diisopropylether successively to obtain 10 mg of the title compound as a colorless powder.

Melting point: 269 to 271° C. (decomposed); $^1$HNMR (d6-DMSO) δ; 3.73 (m, 1H), 4.07 (m, 2H), 4.67 (m, 2H), 7.81 (d, J=15 Hz, 1H), 7.95 (brs, 1H), 8.29 (d, J=3 Hz, 1H), 8.83 (s, 1H).

REFERENCE EXAMPLE 23

Synthesis of 2-amino-3,5-difluoro-6-methoxypyridine

To 1 ml of methanol were added 500 mg of 2-amino-3,5,6-trifluoropyridine together with 800 mg of 28% sodium methoxide/methanol solution, and the mixture was stirred at 70° C. for 3 and half hours, and allowed to cool. After adding 25 ml of chloroform, the mixture was washed with 5 ml of distilled water. The chloroform layer was dried over anhydrous magnesium sulfate, and concentrated under reduced pressure to obtain the title product.

EXAMPLE 30

Synthesis of ethyl 8-chloro-1-(3,5-difluoro-6-methoxypyridine-2-yl)-6,7-difluoro-4-oxo-1,4-dihydroquinoline-3-carboxylate To 3 ml chloroform solution of ethyl 3-ethoxy-2-(3-chloro-2,4,5-trifluorobenzoyl)acrylate prepared from 0.78 g of ethyl 3-chloro-2,4,5-trifluorobenzoylacetate by normal process was added 2-amino-3,5-difluoro-6-methoxypyridine until completion of the conversion into the aminoacrylate form was confirmed by monitoring the reaction by TLC. The solution was concentrated under reduced pressure, and to the residue were added 0.80 g of anhydrous potassium carbonate and 2 ml of N,N-dimethylformamide, and the mixture was stirred at 90° C. for 15 minutes and allowed to cool. The solution was separated by adding 30 ml of chloroform and 300 ml of distilled water, and the chloroform layer was washed twice with 300 ml of distilled water, dried over anhydrous magnesium sulfate, concentrated under reduced pressure, and allowed to stand. The precipitate was collected by filtration, washed with ethanol to obtain 615 mg of the title compound as a pale brown powder.

Melting point: 140 to 143° C.; $^1$HNMR (CDCl$_3$) δ; 1.41 (t, J=7 Hz, 3H), 3.99 (s, 3H), 4.41 (q, J=7 Hz, 2H), 7.44 (t, J=8 Hz, 1H), 8.33 (dd, J=8 Hz, 10 Hz), 8.45 (s, 1H).

EXAMPLE 31

Synthesis of 8-chloro-1-(3,5-difluoro-6-methoxypyridine-2-yl)-6,7-difluoro-4-oxo-1,4-dihydroquinoline-3-carboxylic acid To a mixed solution of 1 ml of 4N hydrochloric acid and 1 ml of acetic acid was added 385 mg of ethyl 8-chloro-1-(3,5-difluoro-6-methoxypyridine-2-yl)-6,7-difluoro-4-oxo-1,4-dihydroquinoline-3-carboxylate, and the mixture heated under reflux with stirring for 30 minutes. After adding 2 ml of distilled water, the solution was allowed to cool and stand. The precipitate was collected by filtration, and washed with ethanol and diisopropylether successively to obtain 297 mg of the title compound as a colorless powder.

Melting point: 205 to 210° C.; $^1$HNMR (d$_6$-DMSO) δ; 3.92 (s, 3H), 8.39 (t, J=9 Hz, 1H), 8.40 (t, J=9 Hz, 1H), 9.03 (s, 1H).

EXAMPLE 32

Synthesis of 7-(3-aminoazetidine-1-yl)-8-chloro-1-(3,5-difluoro-6-methoxypyridine-2-yl)-6-fluoro-4-oxo-1,4-dihydroquinoline-3-carboxylic acid To 500 mg of acetonitrile were added 75 mg of 8-chloro-1-(3,5-difluoro-6-methoxypyridine-2-yl)-6,7-difluoro-4-oxo-1,4-dihydroquinoline-3-carboxylic acid, 65 mg of 3-aminoazetidine dihydrochloride, and 150 mg of N-methylpyrrolidine, and the mixture was heated under reflux for 1 hour. The precipitate was collected by filtration and washed with ethanol and diisopropylether successively to obtain 28 mg of the title compound as a colorless powder.

Melting point: 171 to 175° C.; $^1$HNMR (d$_6$-DMSO) δ; 3.70 (m, 1H), 3.91 (s, 3H), 4.05 (m, 2H), 4.66 (m, 2H), 7.88 (d, J=14 Hz, 1H), 8.34 (t, J=9 Hz, 1H), 8.79 (s, 1H).

EXAMPLE 33

Synthesis of ethyl 7-chloro-1-(3,5-difluoro-6-methoxypyridine-2-yl)-6-fluoro-4-oxo-1,4-dihydro-1,8-naphthylidine-3-carboxylate To 10 ml chloroform solution of ethyl 3-ethoxy-2-(2,6-dichloro-5-fluoronicotinoyl)acrylate prepared from 1.25 g of ethyl 2,6-dichloro-5-fluoronicotinoylacetate by normal process was added the crude 2-amino-3,5-difluoro-6-methoxypyridine until completion of the conversion into the aminoacrylate form was confirmed by monitoring the reaction by TLC. The solution was concentrated under reduced pressure, and to the residue were added 2.0 g of anhydrous potassium carbonate and 4 ml of N,N-dimethylformamide, and the mixture was stirred at 90° C. for 20 minutes and allowed to cool. The solution was separated by adding 50 ml of chloroform and 300 ml of distilled water, and the chloroform layer was washed twice with 300 ml of distilled water, dried over anhydrous magnesium sulfate, and concentrated under reduced pressure. The precipitate was dispersed in ethanol, collected by filtration, and washed with ethanol and diisopropylether successively to obtain 1010 mg of the title compound as a pale brown powder.

Melting point: 208 to 212° C.; $^1$HNMR (CDCl$_3$) δ; 1.42 (t, J=7 Hz, 3H), 4.04 (s, 3H), 4.40 (q, J=7 Hz, 2H), 7.50 (t, J=8 Hz, 1H), 8.48 (d, J=7 Hz), 8.69 (s, 1H).

EXAMPLE 34

Synthesis of 7-chloro-1-(3,5-difluoro-6-methoxypyridine-2-yl)-6-fluoro-4-oxo-1,4-dihydro-1,8-naphthylidine-3-carboxylic acid To 1.5 ml of a mixed solution (1:1, v/v) of 3N hydrochloric acid and acetic acid was added 300 mg of ethyl 7-chloro-1-(3,5-difluoro-6-methoxypyridine-2-yl)-6-fluoro-4-oxo-1,4-dihydro-1,8-naphthylidine-3-carboxylate, and the mixture was heated under reflux with stirring for 1 hour. After adding 2 ml of distilled water, the mixture was heated under reflux for 10 minutes and allowed to cool, and the precipitate was collected by filtration and washed with ethanol and diisopropylether successively to obtain 248 mg of the title compound as a pale brown powder.

Melting point: 220 to 225° C.; $^1$HNMR (d$_6$-DMSO) δ; 3.97 (s, 3H), 8.42 (t, J=9 Hz, 1H), 8.76 (d, J=7 Hz, 1H), 9.21 (s, 1H).

EXAMPLE 35

Synthesis of 7-[(3S)-3-aminopyrrolidine-1-yl]-1-(3,5-difluoro-6-methoxypyridine-2-yl)-6-fluoro-4-oxo-1,4-dihydro-1,8-naphthylidine-3-carboxylic acid To 400 mg of N,N-dimethylformamide were added 82 mg of 7-chloro-1-(3,5-difluoro-6-methoxypyridine-2-yl)-6-fluoro-4-oxo-1,4-dihydro-1,8-naphthylidine-3-carboxylic acid, 70 mg of (3S)-3-aminopyrrolidine, and 60 mg of triethylamine, and the mixture was heated under reflux at 80° C. for 30 minutes. After adding 2.5 ml of ethanol, the mixture was heated under reflux for 5 minutes and allowed to cool, and the precipitate was collected by filtration, and washed with ethanol and diisopropylether successively to obtain 102 mg of the title compound as a pale brown powder.

Melting point: 231 to 233° C.; $^1$HNMR (d$_6$-DMSO) δ; 1.65 (m, 1H), 1.93 (m, 1H), 3.95 (s, 3H), 8.02 (d, J=13 Hz, 1H), 8.35 (t, J=9 Hz, 1H), 8.94 (s, 1H); (Part of signals overlapped with the proton of water, and were undistinguishable.).

EXAMPLE 36

Synthesis of 7-r(3S,4S)-3-amino-4-methylpyrrolidine-1-yl]-1-(3,5-difluoro-6-methoxypyridine-2-yl)-6-fluoro-4-oxo-1,4-dihydro-1,8-naphthylidine-3-carboxylic acid To 500 mg of N,N-dimethylformamide were added 85 mg of 7-chloro-1-(3,5-difluoro-6-methoxypyridine-2-yl)-6- fluoro-4-oxo-1,4-dihydro-1,8-naphthylidine-3-carboxylic acid, 70 mg of (3S,4S)-3-amino-4-methylpyrrolidine dihydrochloride, and 150 mg of triethylamine, and the mixture was heated under reflux at 80° C. for 30 minutes. After adding 2.5 ml of ethanol, the mixture was heated under reflux for 5 minutes and allowed to cool, and the precipitate was collected by filtration, and washed with ethanol and diisopropylether successively to obtain 105 mg of the title compound as a colorless powder.

Melting point: 226 to 229° C.; $^1$HNMR ($d_6$-DMSO) δ; 0.94 (brd, J=8 Hz, 3H), 2.16 (m, 1H), 3.95 (s, 3H), 8.02 (d, J=13 Hz, 1H), 8.35 (m, 1H), 8.95 (s, 1H); (Part of signals overlapped with the proton of water, and were undistinguishable.).

EXAMPLE 37

Synthesis of 1-(6-amino-3,5-difluoropyridine-2-yl)-8-bromo-6,7-difluoro-4-oxo-1,4-dihydroquinoline-3-carboxylic acid To a mixed solution of 3.5 ml of 4N hydrochloric acid and 3.5 ml of acetic acid was added 1.38 g of ethyl 8-bromo-1-[6-(t-butylamino)-3,5-difluoropyridine-2-yl]-6,7-difluoro-4-oxo-1,4-dihydroquinoline-3-carboxylate, and the mixture was heated under reflux with stirring for 5 hours. After adding 5 ml of distilled water, the mixture was allowed to cool, and the precipitate was collected by filtration and washed with ethanol and diisopropylether successively to obtain 1.10 g of the title compound as a colorless powder.

Melting point: 272 to 278° C. $^1$HNMR ($d_6$-DMSO) δ; 6.80 (s, 2H), 7.99 (t, J=9 Hz, 1H), 8.38 (t, J=9 Hz, 1H), 8.93 (s, 1H).

EXAMPLE 38

Synthesis of 1-(6-amino-3,5-difluoropyridine-2-yl)-6,7,8-trifluoro-4-oxo-1,4-dihydroquinoline-3-carboxylic acid To a mixed solution of 0.5 ml of 4N hydrochloric acid and 0.5 ml of acetic acid was added 235 mg of ethyl 1-[6-(t-butylamino)-3,5-difluoropyridine-2-yl]-6,7,8-trifluoro-4-oxo-1,4-dihydroquinoline-3-carboxylate, and the mixture was heated under reflux with stirring for 7 hours. After adding 1 ml of distilled water, the mixture was allowed to cool, and the precipitate was collected by filtration and washed with ethanol and diisopropylether successively to obtain 182 mg of the title compound as a colorless powder.

Melting point: 280° C. or higher $^1$HNMR ($d_6$-DMSO) δ; 6.81 (brs, 2H), 8.04 (t, J=9 Hz, 1H), 8.23 (m, 1H), 8.98 (s, 1H).

EXAMPLE 39

Synthesis of 7-(3-aminoazetidine-1-yl)-1-(6-amino-3,5-difluoropyridine-2-yl)-8-bromo-6-fluoro-4-oxo-1,4-dihydroquinoline-3-carboxylic acid To 300 mg of N,N-dimethylformamide were added 105 mg of 1-(6-amino-3,5-difluoropyridine-2-yl)-8-bromo-6,7-difluoro-4-oxo-1,4-dihydroquinoline-3-carboxylic acid, 70 mg of 3-aminoazetidine dihydrochloride, and 150 mg of N-methylpyrrolidine, and the mixture was stirred at 90° C. for 1 hour. After adding 0.3 ml of ethanol, the mixture was allowed to cool, and the precipitate was collected by filtration and washed with ethanol and diisopropylether successively to obtain 79 mg of the title compound as a colorless powder.

Melting point: 258 to 264° C. (decomposed); $^1$HNMR ($d_6$-DMSO) δ; 3.73 (m, 1H), 4.06 (m, 2H), 4.69 (m, 2H), 6.75 (brs, 2H), 7.89 (d, J=14 Hz, 1H), 7.94 (t, J=9 Hz, 1H), 8.70 (s, 1H).

EXAMPLE 40

Synthesis of 7-(3-aminoazetidine-1-yl)-1-(6-amino-3,5-difluoropyridine-2-yl)-6,8-difluoro-4-oxo-1,4-dihydroquinoline-3-carboxylic acid To 270 mg of N,N-dimethylformamide were added 90 mg of 1-(6-amino-3,5-difluoropyridine-2-yl)-6,7,8-trifluoro-4-oxo-1,4-dihydroquinoline-3-carboxylic acid, 50 mg of 3-aminoazetidine dihydrochloride, and 110 mg of N-methylpyrrolidine, and the mixture was stirred at 90° C. for 1 hour. After adding 0.3 ml of ethanol, the mixture was allowed to cool, and the precipitate was collected by-filtration and washed with ethanol and diisopropylether successively to obtain 70 mg of the title compound as a colorless powder.

Melting point: 256 to 260° C. (decomposed); $^1$HNMR ($d_6$-DMSO) δ; 3.76 (m, 1H), 3.94 (m, 2H), 4.44 (m, 2H), 6.74 (brs, 2H), 7.78 (d, J=13 Hz, 1H), 7.99 (t, J=9 Hz, 1H), 8.73 (s, 1H).

EXAMPLE 41

Synthesis of 1-(6-amino-3,5-difluoropyridine-2-yl)-8-bromo-6-fluoro-7-(3-methylaminoazetidine-1 -yl)-4-oxo-1,4-dihydroquinoline-3-carboxylic acid To 800 mg of N,N-dimethylformamide were added 260 mg of 1-(6-amino-3,5-difluoropyridine-2-yl)-8-bromo-6,7-difluoro-4-oxo-1,4-dihydroquinoline-3-carboxylic acid, 130 mg of 3-methylaminoazetidine dihydrochloride, and 300 mg of N-methylpyrrolidine, and the mixture was stirred at 90° C. for 1 hour. After adding 0.5 ml of ethanol, the mixture was allowed to cool, and the precipitate was collected by filtration and washed with ethanol and diisopropylether successively to obtain 247 mg of the title compound as a pale yellow powder.

Melting point: 238 to 245° C. (decomposed); $^1$HNMR ($d_6$-DMSO) δ; 2.21 (s, 3H), 3.46 (m, 1H), 4.12 (m, 2H), 4.63 (m, 2H), 6.75 (brs, 2H), 7.88 (d, J=14 Hz, 1H), 7.94 (t, J=9 Hz, 1H), 8.70 (s, 1H).

EXAMPLE 42

Synthesis of 7-[3-(ethylamino)azetidine-1-yl]-1-(6-amino-3,5-difluoropyridine-2-yl)-8-chloro-6-fluoro-4-oxo-1,4-dihydroquinoline-3-carboxylic acid To 310 mg of N,N-dimethylformamide were added 100 mg of 1-(6-amino-3,5-difluoropyridine-2-yl)-8-chloro-6,7-difluoro-4-oxo-1,4-dihydroquinoline-3-carboxylic acid, 70 mg of 3-(ethylamino)azetidine dihydrochloride, and 150 mg of N-methylpyrrolidine, and the mixture was stirred at 90° C. for 15 minutes. After adding 1 ml of ethanol, the mixture was allowed to cool, and the precipitate was collected by filtration and washed with ethanol and diisopropylether successively to obtain 107 mg of the title compound as a colorless powder.

Melting point: 241 to 245° C. (decomposed); $^1$HNMR ($d_6$-DMSO) δ; 0.98 (t, J=7 Hz, 3H), 2.49 (q, J=7 Hz, 2H), 3.55 (m, 1H), 4.14 (m, 2H), 4.66 (m, 2H), 6.76 (brs, 2H), 7.86 (d, J=14 Hz, 1H), 7.95 (t, J=9 Hz, 1H), 8.69 (s, 1H).

EXAMPLE 43

Synthesis of 7-[3-(dimethylamino)azetidine-1-yl]-1-(6-amino-3,5-difluoropyridine-2-yl)-8-chloro-6-fluoro-4-oxo-1,4-dihydroquinoline-3-carboxylic acid To 310 mg of N,N-dimethylformamide were added 100 mg of 1-(6-amino-3,5-difluoropyridine-2-yl)-8-chloro-6,7- difluoro-4-oxo-1,4-dihydroquinoline-3-carboxylic acid, 100 mg of 3-(dimethylamino)azetidine dihydrochloride, and 150 mg of N-methylpyrrolidine, and the mixture was stirred at 90° C. for 15 minutes. After adding 1 ml of ethanol, the mixture was allowed to cool, and the precipitate was collected by filtration and washed with ethanol and diisopropylether successively to obtain 87 mg of the title compound as a colorless powder.

Melting point: 283 to 287° C. (decomposed); $^1$HNMR ($d_6$-DMSO) δ; 2.07 (s, 6H), 3.03 (m, 1H), 4.24 (m, 2H), 4.55 (m, 2H), 6.77 (brs, 2H), 7.86 (d, J=14 Hz, 1H), 7.95 (t, J=9 Hz, 1H), 8.70 (s, 1H).

EXAMPLE 44

Synthesis of 7-[3-(aminomethyl)azetidine-1-yl]-1-(6-amino-3,5-difluoropyridine-2-yl)-8-chloro-6-fluoro-4-oxo-1,4-dihydroquinoline-3-carboxylic acid To 280 mg of N,N-dimethylformamide were added 80 mg of 1-(6-amino-3,5-difluoropyridine-2-yl)-8-chloro-6,7-difluoro-4-oxo-1,4-dihydroquinoline-3-carboxylic acid, 100 mg of 3-(aminomethyl)azetidine dihydrochloride, and 200 mg of N-methylpyrrolidine, and the mixture was stirred at 90° C. for 25 minutes. After adding 0.5 ml of ethanol, the mixture was allowed to cool, and the precipitate was collected by filtration and washed with ethanol and diisopropylether successively to obtain 42 mg of the title compound as a colorless powder.

Melting point: 249 to 254° C. $^1$HNMR ($d_6$-DMSO) δ; 2.67 (m, 1H), 2.80 (m, 2H), 4.21 (m, 2H), 4.49 (m, 2H), 6.73 (brs, 2H), 7.80 (d, J=14 Hz, 1H), 7.93 (t, J=10 Hz, 1H), 8.56 (s, 1H).

REFERENCE EXAMPLE 24

Synthesis of 4-amino-3-chloro-2,5,6-trifluoropyridine

To 100 ml of acetonitrile was dissolved 20.5 g of 3-chloro-2,4,5,6-tetrafluoropyridine, and 30 ml of 25% aqueous solution of ammonia was added in three portions while the mixture was stirred and cooled with water, and the stirring was continued for another 30 minutes. The solution was concentrated under reduced pressure. After adding 200 ml of chloroform to the solid residue, the solution was washed with 50 ml of distilled water. The chloroform layer was dried over anhydrous magnesium sulfate and concentrated under reduced pressure, and the precipitate was collected by filtration to obtain 16.6 g of the title compound as colorless flake crystals.

REFERENCE EXAMPLE 25

Synthesis of 4-bromo-3-chloro-2,5,6-trifluoropyridine

To 45 ml of acetonitrile was dissolved 9.4 g of 4-amino-3-chloro-2,5,6-trifluoropyridine, and 7.5 g of t-butylnitrite was added dropwise in 25 minites stirring at 45° C., and the mixture was heated under reflux for 40 minutes and concentrated under reduced pressure. The residue was separated by adding 150 ml of chloroform and 100 ml of 2N hydrochloric acid, and the chloroform layer was washed with 20 ml of distilled water. The chloroform layer was dried over anhydrous magnesium sulfate and concentrated under reduced pressure to obtain 10.2 g of the title compound as pale yellow oil.

REFERENCE EXAMPLE 26

Synthesis of 4-bromo-2-(t-butylamino)-5-chloro-3,6-difluoropyridine

To 40 ml of acetonitrile was dissolved 10.2 g of 4-bromo-3-chloro-2,5,6-trifluoropyridine and 10.5 g of t-butylamine, and the mixture was heated under reflux for 1 hour and the solvent and the like were distilled off under reduced pressure. To the residue was added 80 ml of chloroform and the mixture was washed with 50 ml of distilled water. The chloroform layer was dried over anhydrous magnesium sulfate and concentrated under reduced pressure to obtain 12.8 g of the title compound as reddish orange oil.

REFERENCE EXAMPLE 27

Synthesis of 2-(t-butylamino)-5-chloro-3,6-difluoropyridine

To 30 ml of methanol were added 12.8 g of 4-bromo-2-(t-butylamino)-5-chloro-3,6-difluoropyridine and 2.5 g of triethylamine together with 0.57 g of 10% palladium on carbon, and the mixture was hydrogenated at 50° C. for 5 days. The catalyst was separated by filtration, and the solvent and the like were distilled off under reduced pressure. To the residue was added 80 ml of chloroform, and the mixture was washed with 70 ml of distilled water, and the chloroform layer was dried over anhydrous magnesium sulfate and concentrated under reduced pressure to obtain 9.3 g of the title compound as a brown oil.

REFERENCE EXAMPLE 28

Synthesis of 2-benzylamino-6-(t-butylamino)-3-chloro-5-fluoropyridine

To 10 ml of N-methylpyrrolidone was added 6.8 g of 2-(t-butylamino)-5-chloro-3,6-difluoropyridine together with 8.0 g of benzylamine, and the mixture was stirred at 150° C. for one day, and allowed to cool. After 80 ml of chloroform, the mixture was washed three times with 300 ml of distilled water. The chloroform layer was dried over anhydrous magnesium sulfate and concentrated under reduced pressure. The residue was subjected to column chromatography (silica gel, 100 g; eluent: chloroform:n-hexane, 1:1) to obtain about 7.0 g of the title compound as a pale brown crude oil.

REFERENCE EXAMPLE 29

Synthesis of 2-amino-6-(t-butylamino)-3-chloro-5-fluoropyridine and 2-amino-6-(t-butylamino)-5-fluoropyridine To a mixed solution of 18 ml methanol and 1.4 g concentrated hydrochloric acid were added 3.1 g of 20 2-benzylamino-6-(t-butylamino)-3-chloro-5-fluoropyridine together with 0.33 g of 10% palladium on carbon, and the mixture was hydrogenated at 30° C. for 1 hour. The catalyst was separated by filtration, and the solvent and the like were distilled off under reduced pressure. To the residue was added 50 ml of chloroform, and the mixture was washed with 10 ml of 6% aqueous solution of sodium hydroxide, and the chloroform layer was dried over anhydrous magnesium sulfate and concentrated under reduced pressure. The residue was subjected to column chromatography (silica gel, 40 g; eluent: chloroform:n-hexane, 3:1 and then 1:1) to obtain 1.35 g of 2-amino-6-(t-butylamino)-3-chloro-5-fluoropyridine as a pale brown oil, and 0.32 g of 2-amino-6-(t-butylamino)-5-fluoropyridine as a brown oil.

2-amino-6-(t-butylamino)-3-chloro-5-fluoropyridine $^1$HNMR (CDCl$_3$) δ; 1.44 (s, 9H), 4.32 (brs, 1H), 4.37 (brs, 1H), 7.02 (d, J=10 Hz, 1H).

2-amino-6-(t-butylamino)-5-fluoropyridine $^1$HNMR (CDCl$_3$) δ; 1.46 (s, 9H), 3.99 (brs, 1H), 4.30 (brs, 1H), 5.61 (dd, J=2 Hz, 8 Hz, 1H), 6.91 (dd, J=8 Hz, 11 Hz, 1H).

EXAMPLE 45

Synthesis of ethyl 1-[6-(t-butylamino)-3-chloro-5-fluoropyridine-2-yl]-8-chloro-6,7-difluoro-4-oxo-1,4-dihydroquinoline-3-carboxylate To 3 ml chloroform solution of ethyl 3-ethoxy-2-(3-chloro-2,4,5-trifluorobenzoyl)acrylate prepared from 0.84 g of ethyl 3-chloro-2,4,5-trifluorobenzoylacetate by normal process was added 0.65 g of 2-amino-6-(t-butylamino)-3-chloro-5-fluoropyridine. The solution was concentrated under reduced pressure to obtain yellow solid residue. To this residue were added 0.7 g of anhydrous potassium carbonate and 3 ml of N,N-dimethylformamide, and the mixture was stirred at 90° C. for 25 minutes and allowed to cool. The solution was separated by adding 40 ml of chloroform and 300 ml of distilled water, and the chloroform layer was washed twice with 300 ml of distilled water, dried over anhydrous magnesium sulfate, concentrated under reduced pressure, and allowed to stand. The precipitate was collected by filtration, washed with ethanol and diisopropylether successively to obtain 1.06 g of the title compound as a pale yellow powder.

Melting point: 210 to 213° C.; $^1$HNMR (CDCl$_3$) δ; 1.38 (s, 9H), 1.41 (t, J=7 Hz, 3H), 4.41 (q, J=7 Hz, 2H), 4.84 (brs, 1H), 7.32 (d, J=10 Hz, 1H), 8.32 (dd, J=8 Hz, 10 Hz, 1H), 8.45 (s, 1H).

EXAMPLE 46

Synthesis of 1-(6-amino-3-chloro-5-fluoropyridine-2-yl)-8-chloro-6,7-difluoro-4-oxo-1,4-dihydroquinoline-3-carboxylic acid To a mixed solution (1:1) of 2.5 ml of 4N hydrochloric acid and acetic acid was added 600 mg of ethyl 1-[6-(t-butylamino)-3-chloro-5-fluoropyridine-2-yl]-8-chloro-6,7-difluoro-4-oxo-1,4-dihydroquinoline-3-carboxylate, and the mixture was heated under reflux with stirring for 4.5 hours. After adding 2 ml of distilled water, the solution was allowed to cool and the precipitate was collected by filtration and washed with ethanol and diisopropylether successively to obtain 458 mg of the title compound as a pale yellow powder.

Melting point: 280° C. or higher; $^1$HNMR (d$_6$-DMSO) δ; 7.10 (brs, 2H), 7.99 (d, J=10 Hz, 1H), 8.40 (t, J=10 Hz, 1H), 8.89 (s, 1H).

EXAMPLE 47

Synthesis of 7-(3-aminoazetidine-1-yl)-1-(6-amino-3-chloro-5-fluoropyridine-2-yl)-8-chloro-6-fluoro-4-oxo-1,4-dihydroquinoline-3-carboxylic acid To 300 mg of N,N-dimethylformamide were added 100 mg of 1-(6-amino-3-chloro-5-fluoropyridine-2-yl)-8-chloro-6,7-difluoro-4-oxo-1,4-dihydroquinoline-3-carboxylic acid, 70 mg of 3-aminoazetidine dihydrochloride, and 150 mg of N-methylpyrrolidone, and the mixture was stirred at 90° C. for 30 minutes. After adding 0.3 ml of ethanol, the mixture was allowed to cool, and the precipitate was collected by filtration and washed with ethanol and diisopropylether successively to obtain 95 mg of the title compound as a colorless powder.

Melting point: 268 to 270° C. (decomposed); $^1$HNMR (d$_6$-DMSO) δ; 3.71 (m, 1H), 4.08 (m, 2H), 4.67 (m, 2H), 7.04 (brs, 2H), 7.87 (d, J=14 Hz, 1H), 7.94 (d, J=10 Hz, 1H), 8.62 (s, 1H).

EXAMPLE 48

Synthesis of 1-(6-amino-3-chloro-5-fluoropyridine-2-yl)-8-chloro-6-fluoro-7-(3-methylaminoazetidine-1-yl)-4-oxo-1,4-dihydroquinoline-3-carboxylic acid To 300 mg of N,N-dimethylformamide were added 103 mg of 1-(6-amino-3-chloro-5-fluoropyridine-2-yl)-8-chloro-6,7-difluoro-4-oxo-1,4-dihydroquinoline-3-carboxylic acid, 85 mg of 3-methylaminoazetidine dihydrochloride, and 150 mg of N-methylpyrrolidone, and the mixture was stirred at 85° C. for 30 minutes. After adding 0.3 ml of ethanol, the mixture was allowed to cool, and the precipitate was collected by filtration and washed with ethanol and diisopropylether successively to obtain 98 mg of the title compound as a colorless powder.

Melting point: 277 to 280° C. (decomposed); $^1$HNMR (d$_6$-DMSO) δ; 2.20 (s, 3H), 3.45 (m, 1H), 4.13 (m, 2H), 4.64 (m, 2H), 7.04 (brs, 2H), 7.87 (d, J=14 Hz, 1H), 7.94 (d, J=10 Hz, 1H), 8.62 (s, 1H).

EXAMPLE 49

Synthesis of ethyl 1-[6-(t-butylamino)-5-fluoropyridine-2-yl]-8-chloro-6,7-difluoro-4-oxo-1,4-dihydroquinoline-3-carboxylate To 2 ml chloroform solution of ethyl 3-ethoxy-2-(3-chloro-2,4,5-trifluorobenzoyl)acrylate prepared from 0.56 g of ethyl 3-chloro-2,4,5-trifluorobenzoylacetate by normal process was added 0.42 g of 2-amino-6-(t-butylamino)-5-fluoropyridine. The solution was concentrated under reduced pressure to obtain yellow solid residue. To this residue were added 0.6 g of anhydrous potassium carbonate and 1.5 ml of N,N-dimethylformamide, and the mixture was stirred at 90° C. for 20 minutes and allowed to cool. The solution was separated by adding 40 ml of chloroform and 300 ml of distilled water, and the chloroform layer was washed twice with 300 ml of distilled water, dried over anhydrous magnesium sulfate, concentrated under reduced pressure, supplemented with 2 ml of ethanol, and allowed to stand. The precipitate was collected by filtration, washed with ethanol and diisopropylether successively to obtain 0.48 g of the title compound as a pale yellow powder.

Melting point: 207 to 210° C. $^1$HNMR (CDCl$_3$) δ; 1.37 (s, 9H), 1.40 (t, J=7 Hz, 3H), 4.40 (q, J=7 Hz, 2H), 4.82 (brs, 1H), 6.52 (dd, J=3 Hz, 8 Hz, 1H), 7.25 (dd, J=8 Hz, 10 Hz, 1H), 8.31 (dd, J=8 Hz, 10 Hz, 1H), 8.61 (s, 1H).

EXAMPLE 50

Synthesis of 1-(6-amino-5-fluoropyridine-2-yl)-8-chloro-6,7-difluoro-4-oxo-1,4-dihydroquinoline-3-carboxylic acid To 2 ml of mixed solution (1:1) of 4N hydrochloric acid and acetic acid was added 450 mg of ethyl 1-[6-(t-butylamino)-5-fluoropyridine-2-yl]-8-chloro-6,7-difluoro-4-oxo-1,4-dihydroquinoline-3-carboxylate, and the mixture was heated under reflux with stirring for 3 hours. After adding 1 ml of distilled water, the mixture was allowed to cool, and the precipitate was collected by filtration and washed with ethanol and diisopropylether successively to obtain 342 mg of the title compound as a colorless powder.

Melting point: 232 to 235° C. $^1$HNMR (d$_6$-DMSO) δ; 6.87 (brs, 2H), 6.91 (dd, J=3 Hz, 8 Hz, 1H), 7.64 (dd, J=8 Hz, 11 Hz, 1H), 8.36 (t, J=9 Hz, 1H), 8.77 (s, 1H).

EXAMPLE 51

Synthesis of 7-(3-aminoazetidine-1-yl)-1-(6-amino-5-fluoropyridine-2-yl)-8-chloro-6-fluoro-4-oxo-1,4-dihydroquinoline-3-carboxylic acid To 270 mg of N,N-dimethylformamide were added 55 mg of 1-(6-amino-5-fluoropyridine-2-yl)-8-chloro-6,7-difluoro-4-oxo-1,4-dihydroquinoline-3-carboxylic acid, 70 mg of 3-aminoazetidine dihydrochloride, and 80 mg of N-methylpyrrolidine, and the mixture was stirred at 90° C. for 15 minutes. After adding 0.3 ml of ethanol, the mixture was allowed to cool, and the precipitate was collected by filtration and washed with ethanol and diisopropylether successively to obtain 62 mg of the title compound as a colorless powder.

Melting point: 250 to 254° C. (decomposed); $^1$HNMR ($d_6$-DMSO) δ; 3.71 (m, 1H), 4.05 (m, 2H), 4.67 (m, 2H), 6.78 (dd, J=3 Hz, 8 Hz, 1H), 6.80 (brs, 2H), 7.60 (dd, J=8 Hz, 10 Hz, 1H), 7.85 (d, J=14 Hz, 1H), 8.60 (s, 1H).

EXAMPLE 52

Synthesis of 1-(6-amino-5-fluoropyridine-2-yl)-8-chloro-6-fluoro-7-(3-methylaminoazetidine-1-yl)-4-oxo-1,4-dihydroquinoline-3-carboxylic acid To 300 mg of N,N-dimethylformamide were added 101 mg of 1-(6-amino-5-fluoropyridine-2-yl)-8-chloro-6,7-difluoro-4-oxo-1,4-dihydroquinoline-3-carboxylic acid, 85 mg of 3-methylaminoazetidine dihydrochloride, and 150 mg of N-methylpyrrolidine, and the mixture was stirred at 85° C. for 30 minutes. After adding 0.3 ml of ethanol, the mixture was allowed to cool, and the precipitate was collected by filtration and washed with ethanol and diisopropylether successively to obtain 82 mg of the title compound as a colorless powder.

Melting point: 252 to 255° C. (decomposed); $^1$HNMR (d6-DMSO) δ; 2.21 (s, 3H), 3.46 (m, 1H), 4.13 (m, 2H), 4.62 (m, 2H), 6.78 (m, 1H), 6.81 (brs, 2H), 7.60 (dd, J=8 Hz, 10 Hz, 1H), 7.84 (d, J=14 Hz, 1H), 8.60 (s, 1H).

REFERENCE EXAMPLE 30

Synthesis of N-(3-chloro-2,5,6-trifluoropyridine-4-yl)phthalimide

To a mixed solution of 40 ml dichloromethane and 20 ml N,N-methylformamide were added 18.5 g of 3-chloro-2,4,5,6-tetrafluoropyridine and 20.5 g potassium phthalimide, and the mixture was stirred at 40° C. for one day. After adding 40 ml of chloroform, the mixture was washed twice with 500 ml of distilled water and once with 500 ml of 0.5% aqueous solution of sodium hydroxide. The organic layer was dried over anhydrous magnesium sulfate and concentrated under reduced pressure. The precipitate was dispersed in diisopropylether, and collected by filtration to obtain 32.0 g of the title compound as a colorless powder.

REFERENCE EXAMPLE 31

Synthesis of N-[2-(t-butylamino)-5-chloro-3,6-difluoropyridine-4-yl]phthalimide

To 150 ml of acetonitrile was added 30.0 g of N-(3-chloro-2,5,6-trifluoropyridine-4-yl)phthalimide together with 42.2 g of t-butylamine, and the mixture was heated under reflux with stirring for 30 minutes. The solution was concentrated under reduced pressure, then 200 ml of chloroform was added, and washed with 100 ml of distilled water. The organic layer was dried over anhydrous magnesium sulfate and concentrated under reduced pressure to obtain about the title compound as colorless solid residue.

REFERENCE EXAMPLE 32

Synthesis of N-(2-amino-5-chloro-3,6-difluoropyridine-4-yl)phthalimide

To 80 ml of trifluoroacetic acid was added all amount of the N-[2-(t-butylamino)-5-chloro-3,6-difluoropyridine-4-yl] phthalimide, and the mixture was stirred at 70° C. for 5 and half hours. The solution was concentrated under reduced pressure. The precipitate was dispersed in chloroform, and collected by filtration to obtain 19.5 g of the title compound as a colorless powder.

REFERENCE EXAMPLE 33

Synthesis of N-(2,5-dichloro-3,6-difluoropyridine-4-yl)phthalimide

To 80 ml of acetonitrile was added 21.3 g of N-(2-amino-5-chloro-3,6-difluoropyridine-4-yl)phthalimide together with 14.0 g of cupric chloride, and the mixture was stirred at room temperature simultaneously with the dropwise addition of 15.8 g of t-butylnitrite dissolved in 30 ml acetonitrile in 10 minites. The mixture was stirred at 60° C. for 1 hour, and concentrated under reduced pressure. The residue was separated by adding 500 ml of chloroform and 250 ml of 2N hydrochloric acid, and the chloroform layer was washed with 50 ml of distilled water. The chloroform-layer was dried over anhydrous magnesium sulfate and concentrated under reduced pressure. The precipitate was dissolved and collected by filtration to obtain 16.2 g of the title compound as a colorless powder.

REFERENCE EXAMPLE 34

Synthesis of 4-amino-2,5-dichloro-3,6-difluoropyridine

To a mixed solution of 100 ml chloroform and 40 ml methanol was added 16.2 g of N-(2,5-dichloro-3,6-difluoropyridine-4-yl)phthalimide together with 20 ml of 25% aqueous solution of ammonia, and the mixture was stirred at room temperature for 30 minutes. The solution was concentrated under reduced pressure, and after adding 150 ml of chloroform to the residue, the mixture was washed with 20 ml of 15% aqueous solution of ammonia, and then, with 10 ml of distilled water. The chloroform layer was dried over anhydrous magnesium sulfate and concentrated under reduced pressure to obtain 4.55 g of the title compound as a colorless powder.

REFERENCE EXAMPLE 35

Synthesis of 4-amino-2,5-difluoropyridine

To 40 ml of methanol were added 4.5 g of 4-amino-2,5-dichloro-3,6-difluoropyridine and 4.5 g of triethylamine together with 0.40 g of 10% palladium carbon, and the mixture was hydrogenated at 50° C. for 12 days. The catalyst was separated by filtration, and the solvent and the like were distilled off under reduced pressure. To the residue was added 100 ml of chloroform, and the mixture was washed with 10 ml of distilled water. The chloroform layer was dried over anhydrous magnesium sulfate and concentrated under reduced pressure. To the residue were added 1.5 g of triethylamine, 0.35 g of 10% palladium on carbon, and 30 ml of methanol, and the mixture was hydrogenated at 50° C. for 41 hours. The catalyst was separated by filtration, and the solvent-and the like were distilled off under reduced pressure. To the residue was added 100 ml of chloroform, and the mixture was washed with 10 ml of distilled water. The chloroform layer was dried over anhydrous magnesium sulfate and concentrated under reduced pressure to obtain 2.67 g of the title compound as precipitate as a colorless solid.

REFERENCE EXAMPLE 36

Synthesis of 2-benzylamino-4-amino-5-fluoropyridine

To 1 ml of N-methylpyrrolidone was added 410 mg of 4-amino-2,5-difluoropyridine together with 930 mg of benzylamine, and the mixture was allowed to react in nitrogen atmosphere at 150° C. for 3 days and allowed to cool. After adding 30 ml of chloroform, the mixture was washed twice with 300 ml of distilled water. The chloroform layer was dried over anhydrous magnesium sulfate and concentrated under reduced pressure. The residue was subjected to column chromatography (silica gel, 15 g; eluent: chloroform:methanol, 1:0 and then, 50:1) to obtain 400 mg of the title compound as a colorless solid.

$^1$HNMR (CDCl$_3$) δ; 4.06 (brs, 2H), 4.40 (d, J=6 Hz, 2H), 4.60 (brs, 1H), 5.69 (d, J=6 Hz, 1H), 7.33 (m, 5H), 7.75 (d, J=3 Hz, 1H).

REFERENCE EXAMPLE 37

Synthesis of 2,4-diamino-5-fluoropyridine hydrochloride

To 4 ml of methanol having added 400 mg of concentrated hydrochloric acid added thereto was added 350 mg of 2-benzylamino-4-amino-5-fluoropyridine together with 50 mg of 10% palladium on carbon, and the mixture was hydrogenated at 40° C. for 2 days. The catalyst was separated by filtration, and the solvent and the like were distilled off under reduced pressure. Procedure of adding 10 ml of distilled water to the residue and concentrating under reduced pressure was repeated 4 times, and the procedure of adding 10 ml of ethanol and concentrating under reduced pressure was repeated twice. 260 mg of the title compound was obtained as a residue in the form of a yellowish orange paste.

REFERENCE EXAMPLE 38

Synthesis of ethyl 3-(4-amino-5-fluoropyridine-2-yl)amino-2-(3-chloro-2,4,5-trifluorobenzoyl)acrylate and ethyl 3-(2-amino-5-fluoropyridine-4-yl)amino-2-(3-chloro-2,4,5-trifluorobenzoyl)acrylate To 1.2 ml chloroform solution of ethyl 3-ethoxy-2-(3-chloro-2,4,5-trifluorobenzoyl)acrylate prepared from 0.34 g of ethyl 3-chloro-2,4,5-trifluorobenzoylacetate by normal process was added 0.25 g of 2,4-diamino-5-fluoropyridine hydrochloride together with 0.28 g of N-methylpyrrolidine. The solution was concentrated under reduced pressure, and to the residue were added 0.52 g of anhydrous potassium carbonate and 0.8 ml of N,N-dimethylformamide, and the mixture was stirred at 90° C. for 15 minutes and allowed to cool. The solution was separated by adding 20 ml of chloroform and 100 ml of distilled water, and the chloroform layer was washed with 100 ml of distilled water, dried over anhydrous magnesium sulfate, and concentrated under reduced pressure. The residue was subjected to column chromatography (silica gel, 14 g; eluent: chloroform:methanol, 1:0, and then, 100:1), and the fraction containing the main product was concentrated under reduced pressure. The precipitate was dispersed in ethanol, collected by filtration, and washed with ethanol and diisopropylether successively to obtain 1.06 g of the title mixture (1:1 in NMR) as a pale brown powder.

EXAMPLE 53

Synthesis of ethyl 1-(4-amino-5-fluoropyridine-2-yl)-8-chloro-6,7-difluoro-4-oxo-1,4-dihydroquinoline-3-carboxylate To 150 mg of the mixture of ethyl 3-(4-amino-5-fluoropyridine-2-yl)amino-2-(3-chloro-2,4,5-trifluorobenzoyl)acrylate and ethyl 3-(2-amino-5-fluoropyridine-4-yl)amino-2-(3-chloro-2,4,5-trifluorobenzoyl)acrylate were added 230 mg of anhydrous potassium carbonate and 450 mg of N,N-dimethylformamide, and the mixture was stirred at 100° C. for 20 minutes and allowed to cool. The solution was separated by adding 20 ml of chloroform and 100 ml of distilled water, and the chloroform layer was washed with 100 ml of distilled water, dried over anhydrous magnesium sulfate, and concentrated under reduced pressure. The residue was subjected to column chromatography (silica gel, 3.2 g; eluent: chloroform:methanol, 100:1), and the fraction containing the main product was concentrated under reduced pressure to obtain 35 mg of the title compound as a yellow solid residue.

Melting point: 140 to 148° C. $^1$HNMR (CDCl$_3$) δ; 1.38 (.t, J=7 Hz, 3H), 4.37 (q, J=7 Hz, 2H), 4.78 (brs, 2H), 6.78 (d, J=6 Hz, 1H), 8.11 (d, J=3 Hz, 1H), 8.27 (dd, J=8 Hz, 10 Hz, 1H), 8.55 (s, 1H).

EXAMPLE 54

Synthesis of 1-(4-amino-5-fluoropyridine-2-yl)-8-chloro-6,7-difluoro-4-oxo-1,4-dihydroquinoline-3-carboxylic acid To 400 mg of the mixed solution (1:1) of 4N hydrochloric acid and acetic acid was added 35 mg of ethyl 1-(4-amino-5-fluoropyridine-2-yl)-8-chloro-6,7-difluoro-4-oxo-1,4-dihydroquinoline-3-carboxylate, and the mixture was heated under reflux with stirring for 3 hours and allowed to cool. The precipitate was collected by filtration, and washed with distilled water, ethanol and diisopropylether successively to obtain 31 mg of the title compound as a pale yellow powder.

Melting point: 280° C. or higher; $^1$HNMR (d$_6$-DMSO) δ; 6.86 (brs, 2H), 7.00 (d, J=7 Hz, 1H), 8.12 (d, J=3 Hz, 1H), 8.39 (t, J=9 Hz, 1H), 8.74 (s, 1H).

EXAMPLE 55

Synthesis of 7-(3-aminoazetidine-1-yl)-1-(4-amino-5-fluoropyridine-2-yl)-8-chloro-6-fluoro-4-oxo-1,4-dihydroquinoline-3-carboxylic acid To 110 mg of N,N-dimethylformamide were added 23 mg of 1-(4-amino-5-fluoropyridine-2-yl)-8-chloro-6,7-difluoro-4-oxo-1,4-dihydroquinoline-3-carboxylic acid, 20 mg of 3-aminoazetidine dihydrochloride, and 50 mg of N-methylpyrrolidine, and the mixture was stirred at 90° C. for 20 minutes. After adding 500 mg of ethanol, the mixture was allowed to cool, and the precipitate was collected by filtration and washed with ethanol and diisopropylether successively to obtain 23 mg of the title compound as a colorless powder.

Melting point: 280° C. or higher; $^1$HNMR (d$_6$-DMSO) δ; 3.75 (m, 1H), 4.10 (m, 2H), 4.66 (m, 2H), 6.77 (brs, 2H), 6.92 (d, J=7 Hz, 1H), 7.86 (d, J=14 Hz, 1H), 8.08 (d, J=3 Hz, 1H), 8.57 (s, 1H).

REFERENCE EXAMPLE 39

Synthesis of methyl 2,6-dichloro-5-fluoronicotinate

To 60 ml of dichloromethane were added 21.0 g of 2,6-dichloro-5-fluoronicotinic acid, 10 ml of oxalylchloride, and 10 drops of N,N-dimethylformamide, and the mixture was stirred at room temperature for one day. The solvent and the excess reagents were distilled off under reduced pressure, and the residue was dissolved in 50 ml of chloroform. 10 ml of methanol was added dropwise to the solution, and the solution was stirred at room temperature for 60 minutes, and 15 g of anhydrous potassium carbonate was added to the solution and the solution was stirred for another 30 minutes. The solution was separated by adding 150 ml of chloroform and 150 ml of distilled water, and the chloroform layer was dried over anhydrous magnesium sulfate, and concentrated under reduced pressure to obtain 26.6 g of the title compound as a colorless crude oily residue.

REFERENCE EXAMPLE 40

Synthesis of methyl 6-t-butylamino-2,5-difluoronicotinate

To 30 ml of dimethylsulfoxide were added three quarter (19.95 g) of the methyl 2,6-dichloro-5-fluoronicotinate synthesized as described above, 14.5 g of potassium fluoride (spray dried), and 1.6 g of tetramethylammonium chloride, and the mixture was stirred at 1100C for 2 and half hours and allowed to cool. After adding 100 ml of chloroform, the mixture was washed twice with 1 liter of distilled water, and once with 1 liter of 1% aqueous solution of sodium carbonate. The chloroform layer was dried over anhydrous magnesium sulfate, and concentrated under reduced pressure. Crude methyl 2,5,6-trifluoronicotinate was obtained in the form of brown oily residue, and this residue was dissolved in 60 ml of acetonitrile, and 12.0 g of t-butylamine was added to this solution. The solution was concentrated under reduced pressure, and the residue was separated by adding 100 ml of chloroform and 60 ml of distilled water. The chloroform layer was dried over anhydrous magnesium sulfate and concentrated under reduced pressure. The precipitate was dispersed in n-hexane, and collected by filtration to obtain 6.85 g of the title compound as a colorless crystals.

$^1$HNMR (CDCl$_3$) δ; 1.50 (s, 9H), 3.86 (s, 3H), 5.04 (brs, 1H), 7.71 (dd, J=7 Hz, llHz, 1H).

REFERENCE EXAMPLE 41

Synthesis of methyl 6-t-butylamino-5-fluoro-2-(1,1,3,3-tetramethylbutylamino)nicotinate To 7 ml N-methylpyrrolidone were added 2.44 g of methyl 6-t-butylamino-2,5-difluoronicotinate and 4.0 g of 1,1,3,3-tetramethylbutylamine, and the mixture was stirred at 140° C. for 16 hours and allowed to cool. After adding 50 ml of chloroform, the mixture was washed three times with 300 ml of distilled water. The chloroform layer was dried over anhydrous magnesium sulfate and concentrated under reduced pressure. The brown oily residue was subjected to column chromatography (silica gel, 40 g; eluent: chloroform:n-hexane, 1:1) to obtain 2.90 g of the title compound as a colorless oily residue.

$^1$HNMR (CDCl$_3$) δ; 0.96 (s, 9H), 1.51 (s, 9H), 1.53 (s, 6H), 3.76 (s, 3H), 4.87 (brs, 1H), 7.52 (d, J=12 Hz, 1H), 8.38 (brs, 1H).

REFERENCE EXAMPLE 42

Synthesis of 2-t-butylamino-3-fluoro-5-methyl-6-(1,1,3,3-tetramethylbutylamino)pyridine To 20 ml of tetrahydrofran was dispersed 850 mg of lithium aluminum hydride. The dispersion was water cooled and stirred simultaneously with the dropwise addition of 2.80 g of methyl 6-t-butylamino-5-fluoro-2-(1,1,3,3-tetramethylbutylamino)nicotinate dissolved in 30 ml of tetrahydrofuran. The reactor was placed in an oil bath of 50° C., and the mixture was stirred for two and half hours. The reactor was then water cooled and 8 ml of ethyl acetate was added dropwise, and the mixture was stirred for 1 hour. 8 ml of ethanol was added dropwise, and the mixture was stirred for 1 hour, then 8 ml of distilled water was added dropwise, and the mixture was stirred overnight. The precipitate was separated by filtration, and the filtrate was concentrated under reduced pressure. The residue was subjected to column chromatography (silica gel, 40 g; eluent: chloroform:n-hexane, 1:1) to obtain 1.67 g of the title compound as a colorless oily residue.

$^1$HNMR (CDCl$_3$) δ; 0.99 (s, 9H), 1.47 (s, 9H), 1.52 (s, 6H), 1.91 (s, 3H), 3.73 (brs, 1H), 4.11 (brs, 1H), 6.81 (d, J=12 Hz, 1H).

REFERENCE EXAMPLE 43

Synthesis of 2,6-diamino-3-fluoro-5-methylpyridine

To 800 mg of trifluoroacetic acid was added 340 mg of 2-t-butylamino-3-fluoro-5-methyl-6-(1,1,3,3-tetramethylbutylamino)pyridine, and the mixture was allowed to stand at room temperature for 30 minutes. The solution was concentrated under reduced pressure to obtain crude 2,6-diamino-3-fluoro-5-methylpyridine as a pale brown solid residue.

EXAMPLE 56

Synthesis of ethyl 1-(6-amino-5-fluoro-3-methylpyridine-2-yl)-8-chloro-6,7-difluoro-4-oxo-1,4-dihydroquinoline-3-carboxylate To 1 ml chloroform solution of ethyl 3-ethoxy-2-(3-chloro-2,4,5-trifluorobenzoyl)acrylate prepared from 280 mg of ethyl 3-chloro-2,4,5-trifluorobenzoylacetate by normal process was added all of 2,6-diamino-3-fluoro-5-methylpyridine as described above together with 2 ml of methanol and 4 ml of chloroform. After allowing to stand at room temperature for 40 minutes, the solution was concentrated under reduced pressure. To the residue were added 600 mg of anhydrous potassium carbonate and 1 ml of N,N-dimethylformamide, and the mixture was stirred at 85° C. for 15 minutes and allowed to cool. The solution was separated by adding 30 ml of chloroform and 300 ml of distilled water, and the chloroform layer was washed twice with 300 ml of distilled water. The chloroform layer was dried over anhydrous magnesium sulfate, and concentrated under reduced pressure. To the residue was added 0.5 ml of ethanol, and the mixture was allowed to stand overnight. The precipitate was dispersed in ethanol, collected by filtration, and washed with ethanol and diisopropylether successively to obtain 171 mg of the title compound as a colorless powder.

Melting point: 198 to 202° C.; $^1$HNMR (CDCl$_3$) δ; 1.40 (t, J=7 Hz, 3H), 2.02 (s, 3H), 4.39 (q, J=7 Hz, 2H), 4.71 (brs, 2H), 7.25 (d, J=10 Hz, 1H), 8.34 (t, J=10 Hz, 1H), 8.34 (s, 1H).

EXAMPLE 57

Synthesis of 1-(6-amino-5-fluoro-3-methylpyridine-2-yl)-8-chloro-6,7-difluoro-4-oxo-1,4-dihydroquinoline-3-carboxylic acid To 800 mg of the mixed solution (1:1) of 4N hydrochloric acid and acetic acid was added 160 mg of ethyl 1-(6-amino-5-fluoro-3-methylpyridine-2-yl)-8-chloro-6,7-difluoro-4- oxo-1,4-dihydroquinoline-3-carboxylate, and the mixture was heated under reflux with stirring for 30 minutes. After adding 0.5 ml of distilled water, the solution was allowed to cool, and the precipitate was collected by filtration and washed with ethanol and diisopropylether successively to obtain 145 mg of the title compound as a pale brown powder.

Melting point: 279 to 284° C. (decomposed); $^1$HNMR ($d_6$-DMSO) δ; 1.94 (s, 3H), 6.62 (brs, 2H), 7.57 (d, J=11 Hz, 1H), 8.40 (t, J=9 Hz, 1H), 8.72 (s, 1H).

EXAMPLE 58

Synthesis of 7-(3-aminoazetidine-1-yl)-1-(6-amino-5-fluoro-3-methylpyridine-2-yl)-8-chloro-6-fluoro-4-oxo-1,4-dihydroquinoline-3-carboxylic acid To 250 mg of N,N-dimethylformamide were added 80 mg of 1-(6-amino-5-fluoro-3-methylpyridine-2-yl)-8-chloro-6,7-difluoro-4-oxo-1,4-dihydroquinoline-3-carboxylic acid, 60 mg of 3-aminoazetidine dihydrochloride, and 120 mg of N-methylpyrrolidine, and the mixture was stirred at 85° C. for 45 minutes. After adding 0.5 ml of ethanol, the mixture was allowed to cool, and the precipitate was collected by filtration and washed with ethanol and diisopropylether successively to obtain 72 mg of the title compound as a colorless powder.

Melting point: 256 to 258° C. (decomposed); $^1$HNMR ($d_6$-DMSO) δ; 1.90 (s, 3H), 3.69 (m, 1H), 4.03 (m, 2H), 4.66 (m, 2H), 6.57 (brs, 2H), 7.52 (d, J=11 Hz, 1H), 7.87 (d, J=14 Hz, 1H), 8.47 (s, 1H).

EXAMPLE 59

Synthesis of 7-[3-(methylamino)azetidine-1-yl]-1-(6-amino-5-fluoro-3-methylpyridine-2-yl)-8-chloro-6-fluoro-4-oxo-1,4-dihydroquinoline-3-carboxylic acid To 90 mg of N,N-dimethylformamide were added 25 mg of 1-(6-amino-5-fluoro-3-methylpyridine-2-yl)-8-chloro-6,7-difluoro-4-oxo-1,4-dihydroquinoline-3-carboxylic acid, 25 mg of 3-(methylamino)azetidine dihydrochloride, and 70 mg of N-methylpyrrolidine, and the mixture was stirred at 85° C. for 45 minutes. After adding 0.2 ml of ethanol, the mixture was allowed to cool, and the precipitate was collected by filtration and washed with ethanol and diisopropylether successively to obtain 20 mg of the title compound as a colorless powder.

Melting point: 251 to 253° C. (decomposed); $^1$HNMR ($d_6$-DMSO) δ; 1.90 (s, 3H), 2.20 (s, 1H), 3.44 (m, 1H), 4.12 (m, 2H), 4.63 (m, 2H), 6.57 (brs, 2H), 7.52 (d, J=11 Hz, 1H), 7.86 (d, J=14 Hz, 1H), 8.47 (s, 1H).

REFERENCE EXAMPLE 44

Synthesis of 6-t-butylamino-2-chloro-3-cyano-5-fluoropyridine

To a solution of 7.6 g of 2,6-dichloro-3-cyano-5-fluoropyridine in 40 ml acetonitrile was added 8.8 g of t-butylamine, and the mixture was stirred overnight at room temperature. The solvent was distilled off the reaction solution. The residue was separated by adding methylene chloride and water. The organic layer was dried over magnesium sulfate, and the solvent was distilled off to obtain 6 g of the title compound as a pale yellow powder.

Melting point: 84 to 85° C.; $^1$HNMR (CDCl$_3$) δ; 1.50 (s, 9H), 5.15 (brs, 1H), 7.25 (d, J=11 Hz, 1H).

REFERENCE EXAMPLE 45

Synthesis of 2-benzylamino-6-t-butylamino-3-cyano-5-fluoropyridine

To 40 ml of N-methylpyrrolidone solution of 6 g 6-t-butylamino-2-chloro-3-cyano-5-fluoropyridine was added 6.3 g of benzylamine, and the mixture was stirred under nitrogen atmosphere at 160° C. for 3 hours and allowed to cool. The reaction solution was separated by adding chloroform and water, and the organic layer was dried over magnesium sulfate, and the solvent was distilled off. The precipitated crystals were collected from the residue by filtration to obtain 2 g of the title compound as a pale yellow powder.

Melting point: 138 to 140° C.; $^1$HNMR (CDCl$_3$) δ; 1.38 (s, 9H), 4.63 (d, J=6 Hz, 2H), 4.87 (brs, 1H), 5.25 (brs, 1H), 7.31 (s, 5H).

REFERENCE EXAMPLE 46

Synthesis of 2-amino-6-t-butylamino-3-cyano-5-fluoropyridine

To 500 mg of 2-benzylamino-6-t-butylamino-3-cyano-5-fluoropyridine were added 3 ml acetic acid and 0.5 ml ethanol, and then, 10 microspatulas of palladium black, and the mixture was stirred under hydrogen atmosphere at 60° C. for 2 days. The catalyst was removed with a membrane filter, and the solvent of the filtrate was distilled off. To the residue was added chloroform, and the mixture was washed with aqueous solution of sodium hydrogencarbonate. The organic layer was collected, dried over magnesium sulfate. The solvent was distilled off to obtain 300 mg of the title compound.

EXAMPLE 60

Synthesis of ethyl 1-(6-t-butylamino-3-cyano-5-fluoropyridine-2-yl)-8-chloro-6,7-difluoro-1,4-dihydro-4-oxoguinolone-3-carboxylate A solution of 300 mg of unpurified 2-amino-6-t-butylamino-3-cyano-5-fluoropyridine in 2 ml ethanol was added dropwise to a solution of 420 mg of ethyl 3-ethoxy-2-(3-chloro-2,4,5-trifluorobenzoyl)acrylate in 2 ml ethanol at room temperature, and the mixture was stirred overnight. The solvent was distilled off the reaction solution, and to the residue were added 3 ml of N,N-dimethylformamide and 210 mg of potassium carbonate, and the mixture was stirred at room temperature for 90 minutes and 80° C. for 2 hours. The reaction solution was extracted by adding water and ethyl acetate, and the organic layer was collected and dried over magnesium sulfate. The solvent was distilled off, and the residue was collected by filtration using ethanol and washed with diethylether to obtain 280 mg of the title compound as a pale yellow powder.

Melting point: 245° C. or higher (decomposed); $^1$HNMR (CDCl$_3$) δ; 1.39 (s, 9H), 1.41 (t, J=7 Hz, 3H), 4.41 (q, J=7 Hz, 2H), 5.39 (brs, 1H), 7.43 (d, J=10 Hz, 1H), 8.32 (t, J=9 Hz, 1H), 8.53 (s, 1H).

EXAMPLE 61

Synthesis of 1-(6-amino-3-cyano-5-fluoropyridine-2-yl)-8-chloro-6,7-difluoro-1,4-dihydro-4-oxoguinolone-3-carboxylic acid To 280 mg of ethyl 1-(6-t-butylamino-3-cyano-5-fluoropyridine-2-yl)-8-chloro-6,7-difluoro-1,4-dihydro-4- oxoquinolone-3-carboxylate was added 3 ml of 12N hydrochloric acid, and the mixture was heated under reflux for 6 hours and allowed to cool. The solid precipitate was collected by filtration and washed with ethanol and diethylether successively to obtain 120 mg of the title compound as a pale yellow powder.

Melting point: 277° C. or higher (decomposed); $^1$HNMR (d6-DMSO) δ; 8.00 (brs, 2H), 8.21 (d, J=11 Hz, 1H), 8.40 (t, J=9 Hz, 1H), 9.05 (s, 1H).

EXAMPLE 62

Synthesis of 7-(3-aminoazetidine-1-yl)-1-(6-amino-3-cyano-5-fluoropyridine-2-yl)-8-chloro-6-fluoro-1,4-dihydro-4-oxoquinolone-3-carboxylic acid A solution in 300 mg of N,N-dimethylformamide of 40 mg of 3-aminoazetidine dihydrochloride and 80 mg of triethylamine was stirred at 90 ° C., and 50 mg of 1-(6-amino-3-cyano-5-fluoropyridine-2-yl)-8-chloro-6,7-difluoro-1,4-dihydro-4-oxoquinolone-3-carboxylic acid was added to the solution, and stirred at 90° C. for 10 minutes. To the reaction solution was added 1 ml of ethanol, and the solid precipitate was collected and dried to obtain 36 mg of the title compound as a pale yellow powder.

Melting point: 290° C. or higher; $^1$HNMR (d$_6$-DMSO) δ; 4.09 (m, 1H), 4.48 (m, 2H), 4.79 (m, 2H), 7.90–8.06 (m, 3H), 8.16 (d, J=11 Hz, 1H), 8.33 (brs, 2H), 8.85, (s, 1H).

EXAMPLE 63

Synthesis of ethyl 1-[6-(t-butylamino)-3,5-difluoropyridine-2-yl]-6,7-difluoro-8-methyl-1,4-dihydro-4-oxoguinoline-3-carboxylate To 3.4 g of ethyl 2,4,5-trifluoro-3-methylbenzoyl-acetate was added 3.2 g of acetic anhydride and 2.3 g of triethyl orthoformate, and the mixture was heated under reflux for 4 hours, and the solvent was distilled off. Toluene was added to the residue, and the solution was azeotropically distilled. After adding 5 ml of ethanol to the residue, a solution of 2.7 g of 2-amino-6-(t-butylamino)-3,5-difluoropyridine in 20 ml ethanol was added dropwise at 0° C., and the mixture was stirred at room temperature for 20 minutes. The solvent was distilled off the reaction solution, and the residue was subjected to silica gel column chromatography, and from the eluent of ethyl acetate:hexane, 1:8 was obtained 4.6 g of ethyl 2-(2,4,5-trifluoro-3-methylbenzoyl)-3-[6-(t-butylamino)-3,5-difluoropyridine-2-yl]aminoacrylate as an oil.

To the solution of 4.6 g of the thus obtained ethyl 2-(2,4,5-trifluoro-3-methylbenzoyl)-3-[6-(t-butylamino)-3,5-difluoropyridine-2-yl]aminoacrylate in 10 ml dimethylformamide was added 1.35 g of potassium carbonate, and the mixture was stirred at 100° C. for 50 minutes. The reaction solution was extracted by adding water and acetic acid, and the organic layer was collected and dried over magnesium sulfate. The solvent was distilled off, and the residue was collected by filtration with ethanol and washed with diethylether to obtain 2.6 g of the title compound as a pale yellow powder.

Melting point: 207 to 211° C.; $^1$HNMR (CDCl$_3$) δ; 1.34–1.48 (m, 12H), 1.82 (d, J=3 Hz, 3H), 4.40 (q, J=7 Hz, 2H), 4.75 (brs, 1H), 7.23 (t, J=9 Hz, 1H), 8.22 (t, J=10 Hz, 1H), 8.50 (s, 1H).

EXAMPLE 64

Synthesis of 1-(6-amino-3,5-difluoropyridine-2-yl)-6,7-difluoro-8-methyl-1,4-dihydro-4-oxoquinoline-3-carboxylic acid To 2.5 g of ethyl 1-[6-(t-butylamino)-3,5-difluoropyridine-2-yl]-6,7-difluoro-8-methyl-1,4-dihydro-4-oxoquinoline-3-carboxylate was added 10 ml of 12N hydrochloric acid, and the mixture was heated overnight under reflux. The reaction solution was allowed to stand, and the solid precipitate was collected by filtration and washed with ethanol and then, with diethylether to obtain 1.7 g of the title compound as a pale yellow powder.

Melting point: 274 to 277° C.; $^1$HNMR (d$_6$-DMSO) δ; 1.84 (s, 3H), 6.91 (brs, 2H), 8.03 (t, J=9 Hz, 1H), 8.25 (t, J=9 Hz, 1H), 8.93 (s, 1H).

EXAMPLE 65

Synthesis of 7-(3-aminoazetidine-1-yl)-1-(6-amino-3,5-difluoropyridine-2-yl)-6-fluoro-8-methyl-1,4-dihydro-4-oxoguinoline-3-carboxylic acid A solution of 70 mg of 3-aminoazetidine dihydrochloride, 200 mg of 1,8-diazabicyclo[5,4,0]undecene, and 300 mg of pyridine was stirred at 100° C., and 110 mg of 1-(6-amino-3,5-difluoropyridine-2-yl)-6,7-difluoro-8-methyl-1,4-dihydro-4-oxoquinoline-3-carboxylic acid was added to the solution and the solution was stirred at 100° C. for 6 minutes. The solvent was distilled off the reaction solution, and to the residue was added one drop of acetic acid and 3 ml of ethanol with heating, and the solution was allowed to stand. The solid precipitate was collected and dried to obtain 13 mg of the title compound as a pale yellow powder.

Melting point: 280° C. or higher; $^1$HNMR (d$_6$-DMSO) δ; 1.60 (s, 3H), 3.77 (m, 2H), 3.93 (m, 1H), 4.46 (m, 2H), 6.86 (brs, 2H), 7.75 (d, J=13 Hz, 1H), 7.95 (t, J=9 Hz, 1H), 8.70 (s, 1H).

EXAMPLE 66

Synthesis of 1-(6-amino-3,5-difluoropyridine-2-yl)-6-fluoro-8-methyl-7-(3-methylaminoazetidine-1-yl)-1,4-dihydro-4-oxoguinolone-3-carboxylic acid The title compound (20 mg) was obtained as a pale yellow powder in a similar manner to Example 65 except that 180 mg of 1-(6-amino-3,5-difluoropyridine-2-yl)-.6,7-difluoro-8-methyl-1,4-dihydro-4-oxoquinoline-3-carboxylic acid and 110 mg of 3-aminoazetidine dihydrochloride were used.

Melting point: 229° C. or higher; $^{11}$HNMR (d$_6$-DMSO) δ; 1.63 (s, 3H), 2.21 (s, 3H), 3.87 (m, 1H), 4.02 (m, 1H), 4.43 (m, 2H), 6.86 (brs, 2H), 7.75 (d, J=14 Hz, 1H), 7.97 (t, J=10 Hz, 1H), 8.71 (s, 1H).

EXAMPLE 67

Synthesis of 7-(3-amino-3-methylazetidine-1-yl)-1-(6-amino-3,5-difluoropyridine-2-yl)-6-fluoro-8-methyl-1,4-dihydro-4-oxoquinolone-3-carboxylic acid The title compound (60 mg) was obtained as a pale yellow powder in a similar manner to Example 65 except that 180 mg of 1-(6-amino-3,5-difluoropyridine-2-yl)-6,7-difluoro-8-methyl-1,4-dihydro-4-oxoquinoline-3-carboxylic acid and 110 mg of 3-amino-3-methylazetidine dihydrochloride were used.

Melting point: 235° C. or higher; $^1$HNMR (d$_6$-DMSO) δ; 1.37 (s, 3H), 1.62 (s, 3H), 3.87 (m, 1H), 4.08 (m, 3H), 6.85 (brs, 2H), 7.74 (d, J=14 Hz, 1H), 7.96 (t, J=10 Hz, 1H), 8.70 (s, 1H).

EXAMPLE 68

Synthesis of 1-(6-amino-3,5-difluoropyridine-2-yl)-6,8-difluoro-7-(3-methylaminoazetidine-1-yl)-4-oxo-1,4-dihydroquinoline-3-carboxylic acid To 200 mg of N,N-dimethylformamide were added 65 mg 1-(6-amino-3,5-difluoropyridine-2-yl)-6,7,8-trifluoro-4- oxo-1,4-dihydroquinoline-3-carboxylic acid, 45 mg of 3-methylaminoazetidine dihydrochloride, and 100 mg of N-methylpyrrolidine together with 3 drops of ethanol, and the mixture was stirred at 85° C. for 30 minutes. After adding 0.2 ml of ethanol, the solution was allowed to cool, and the precipitate was collected by filtration and washed with ethanol and diisopropylether successively to obtain 52 mg of the title-compound as a colorless powder.

Melting point: 262 to 268° C. (decomposed); $^1$HNMR ($d_6$-DMSO) δ; 2.19 (s, 3H), 3.52 (m, 1H), 4.01 (m, 2H), 4.44 (m, 2H), 6.75 (brs, 2H), 7.77 (d, J=13 Hz, 1H), 7.99 (t, J=9 Hz, 1H), 8.74 (s, 1H).

EXAMPLE 69

Synthesis of 1-(6-amino-3,5-difluoropyridine-2-yl)-8-bromo-6-fluoro-7-(3-hydroxyazetidine-1-yl)-4-oxo-1,4-dihydroquinoline-3-carboxylic acid To 270 mg of N,N-dimethylformamide were added 110 mg of 1-(6-amino-3,5-difluoropyridine-2-yl)-8-bromo-6,7-difluoro-4-oxo-1,4-dihydroquinoline-3-carboxylic acid, 50 mg of 3-hydroxyazetidine hydrochloride, and 100 mg of N-methy-lpyrrolidine together with 3 drops of ethanol, and the mixture was stirred at 85° C. for 25 minutes. After adding 0.5 ml of ethanol, the solution was allowed to cool, and the precipitate was collected by filtration and washed with ethanol and diisopropylether successively to obtain 101 mg of the title compound as a pale yellow powder.

Melting point: 215 to 220° C.; $^1$HNMR ($d_6$-DMSO) δ; 4.06 (m, 2H), 4.51 (m, 3H), 5.75 (brs, 1H), 6.76 (brs, 2H), 7.79 (d, J=13 Hz, 1H), 7.99 (t, J=9 Hz, 1H), 8.75 (s, 1H).

EXAMPLE 70

Synthesis of 1-(6-amino-3,5-difluoropyridine-2-yl)-8-chloro-6-fluoro-7-(3-hydroxyazetidine-1-yl)-4-oxo-1,4-dihydroquinoline-3-carboxylic acid To 3.5 g of N,N-dimethylformamide were added 2.00 g of 1-(6-amino-3,5-difluoropyridine-2-yl)-8-chloro- 6,7-difluoro-4-oxo-1,4-dihydroquinoline-3-carboxylic acid, 1.00 g of 3-hydroxyazetidine hydrochloride, and 2.00 g of N-methylpyrrolidine together with 0.2 ml of ethanol, and the mixture was stirred at 85° C. for 10 minutes. The solvent and the like were distilled off under reduced pressure. After adding 10 ml. of ethanol to the residue, the mixture was heated under reflux for 10 minutes and allowed to cool, and the precipitate was collected by filtration and washed with ethanol and diisopropylether successively to obtain 2.10 g of the title compound as a pale yellow powder.

Melting point: 235 to 238° C.; $^1$HNMR ($d_6$-DMSO) δ; 4.18 (m, 2H), 4.48 (m, 1H), 4.72 (m, 2H), 5.74 (d, J=6 Hz, 1H), 6.76 (brs, 2H), 7.86 (d, J=14 Hz, 1H), 7.95 (t, J=9 Hz, 1H), 8.70 (s, 1H).

EXAMPLE 71

Synthesis of 1-(6-amino-3,5-difluoropyridine-2-yl)-6,8-difluoro-7-(3-hydroxyazetidine-1-yl)-4-oxo-1,4-dihydroquinoline-3-carboxylic acid To 280 mg of N,N-dimethylformamide were added 125 mg 1-(6-amino-3,5-difluoropyridine-2-yl)-6,7,8-trifluoro-4-oxo-1,4-dihydroquinoline-3-carboxylic acid, 60 mg of 3-hydroxyazetidine hydrochloride, and 120 mg of N-methylpyrrolidine together with 3 drops of ethanol, and the mixture was stirred at 85 C for 10 minutes. After adding 0.8 ml of ethanol, the solution was allowed to cool, and the precipitate was collected by filtration and washed with ethanol and diisopropylether successively to obtain 90 mg of the title compound as a pale yellow powder.

Melting point: 269 to 272° C.; $^1$HNMR ($d_6$-DMSO) δ; 4.06 (m, 2H), 4.51 (m, 3H), 5.75 (brs, 1H), 6.76 (brs, 2H), 7.79 (d, J=13 Hz, 1H), 7.99 (t, J=9 Hz, 1H), 8.75 (s, 1H).

EXAMPLE 72

Synthesis of ethyl 8-bromo-1-[6-(t-butylamino)-5-fluoropyridine-2-yl]-6,7-difluoro-4-oxo-1,4-dihydroquinoline-3-carboxylate To 1 ml of chloroform solution of ethyl 3-ethoxy-2-(3-bromo-2,4,5-trifluorobenzoyl)acrylate prepared from 0.65 g of ethyl 3-bromo-2,4,5-trifluorobenzoylacetate by normal process was added 0.3 g of 2-amino-6-(t-butylamino)-5-fluoropyridine. The solution was concentrated under reduced pressure to obtain yellowish orange solid residue. To this residue were added 0.4 g of anhydrous potassium carbonate and 2 ml of N,N-dimethylformamide, and the mixture was stirred at 90° C. for 25 minutes and allowed to cool. The solution was separated by adding 25 ml of chloroform and 400 ml of distilled water, and the chloroform layer was washed with 400 ml of distilled water, dried over anhydrous magnesium sulfate, and concentrated under reduced pressure. After adding 2 ml of ethanol, the solution was and allowed to stand. The precipitate was dispersed in ethanol and collected by filtration, and washed with ethanol and diisopropylether successively to obtain 0.53 g of the title compound as a pale yellow powder.

Melting point: 192 to 195° C.; $^1$HNMR (CDCl$_3$) δ; 1.37 (s, 9H), 1.40 (t, J=7 Hz, 3H), 4.40 (q, J=7 Hz, 2H), 4.83 (brs, 1H), 6.50 (dd, J=3 Hz, 8 Hz, 1H), 7.24 (dd, J=8 Hz, 10 Hz, 1H), 8.35 (t, J=9 Hz, 1H), 8.65 (s, 1H).

EXAMPLE 73

Synthesis of 1-(6-amino-5-fluoropyridine-2-yl)-8-bromo-6,7-difluoro-4-oxo-1,4-dihydroquinoline-3-carboxylic acid To 4 ml of the mixed solution (1:1) of 4N hydrochloric acid and acetic acid was added 480 mg of ethyl 8-bromo-1-[6-(t-butylamino)-5-fluoropyridine-2-yl]-6,7-difluoro-4-oxo-1,4-dihydroquinoline-3-carboxylate, and the mixture was heated under reflux with stirring for 2 hours. After adding 4 ml of distilled water, the solution was allowed to cool, and the precipitate was collected by filtration and washed with ethanol and diisopropylether successively to obtain 345 mg of the title compound as a colorless powder.

Melting point: 245 to 251° C. (decomposed); $^1$HNMR ($d_6$-DMSO) δ; 6.84–6.92 (m, 3H), 7.64 (dd, J=8 Hz, 11 Hz, 1H), 8.40 (t, J=9 Hz, 1H), 8.79 (s, 1H).

EXAMPLE 74

Synthesis of 7-(3-aminoazetidine-1-yl)-1-(6-amino-5-fluoropyridine-2-yl)-8-bromo-6-fluoro-4-oxo-1,4-dihydroquinoline-3-carboxylic acid To 250 mg of N,N-dimethylformamide were added 80 mg of 1-(6-amino-5-fluoropyridine-2-yl)-8-bromo-6,7-difluoro-4-oxo-1,4-dihydroquinoline-3-carboxylic acid, 55 mg of 3-aminoazetidine dihydrochloride, and 150 mg of N-methylpyrrolidine, and the mixture was stirred at 90° C. for 10 minutes. After adding 0.3 ml of ethanol, the solution was allowed to cool, and the precipitate was collected by filtration and washed with ethanol and diisopropylether successively to obtain 68 mg of the title compound as a colorless powder.

Melting point: 245 to 250° C. (decomposed); $^1$HNMR ($d_6$-DMSO) δ; 3.72 (m, 1H), 4.02 (m, 2H), 4.67 (m, 2H), 6.73 (dd, J=2 Hz, 8 Hz, 1H), 6.82 (brs, 2H), 7.59 (dd, J=8 Hz, 10 Hz, 1H), 7.87 (d, J=14 Hz, 1H), 8.69 (s, 1H).

EXAMPLE 75

Synthesis of 1-(6-amino-5-fluoropyridine-2-yl)-8-bromo-6-fluoro-7-(3-methylaminoazetidine-1-yl)-4-oxo-1,4-dihydroquinoline-3-carboxylic acid To 250 mg of N,N-dimethylformamide were added 80 mg of 1-(6-amino-5-fluoropyridine-2-yl)-8-bromo-6,7-difluoro-4-oxo-1,4-dihydroquinoline-3-carboxylic acid, 80 mg of 3-methylaminoazetidine dihydrochloride, and 200 mg of N-methylpyrrolidine, and the mixture was stirred at 85° C. for 10 minutes. After adding 0.5 ml of ethanol, the solution was allowed to cool, and the precipitate was collected by filtration and washed with ethanol and diisopropylether successively to obtain 66 mg of the title compound as a colorless powder.

Melting point: 210 to 218° C. (decomposed); $^1$HNMR ($d_6$-DMSO) δ; 2.22 (s, 3H), 3.48 (m, 1H), 4.12 (m, 2H), 4.61 (m, 2H), 6.74 (d, J=10 Hz, 2H), 6.81 (brs, 2H), 7.59 (t, J=10 Hz, 1H), 7.87 (d, J=14 Hz, 1H), 8.68 (s, 1H).

REFERENCE EXAMPLE 47

Synthesis of 2-amino-5-chloro-3,6-difluoropyridine

To 25 ml of methanol were added 2.7 g of 2-amino-4-bromo-5-chloro-3,6-difluoropyridine and 1.15 g of triethylamine together with 0.145 g of 10% palladium on carbon, and the mixture was hydrogenated at room temperature for 1.5 hours. The catalyst was separated by filtration, and the solvent and the like were distilled off under reduced pressure. To the residue was added 50 ml of chloroform, and the mixture was washed with 30 ml of distilled water. The chloroform layer was dried over anhydrous magnesium sulfate and concentrated under reduced pressure. The resulting colorless flake crystals were dispersed in a mixed solution of diisopropylether and n-hexane (1:2), and collected by filtration to obtain 1.62 g of the title compound.

REFERENCE EXAMPLE 48

Synthesis of 2-amino-5-chloro-3-fluoro-6-(p-methoxybenzylamino)pyridine

To 2 ml of N-methylpyrrolidone was added 510 mg of 2-amino-5-chloro-3,6-difluoropyridine and 910 mg of p-methoxybenzylamine, and the mixture was stirred at 150° C. for one day, and allowed to cool. After adding a mixed solution of 60 ml benzene and n-hexane (1:1, v/v), the solution was washed twice with 400 ml of distilled water. The organic layer was dried over anhydrous magnesium sulfate, and concentrated under reduced pressure to obtain 960 mg of the title compound as a brown crude oil.

$^1$HNMR (CDCl$_3$) δ; 3.80 (s, 3H), 4.35 (brs, 2H), 4.50 (m, 2H), 4.86 (brs, 1H), 6.87 (d, J=8 Hz, 2H), 7.15 (d, J=10 Hz, 1H), 7.27 (d, J=8 Hz, 2H).

EXAMPLE 76

Synthesis of ethyl 8-chloro-1-[5-chloro-3-fluoro-6-(p-methoxybenzylamino)pyridine-2-yl]-6,7-difluoro-4-oxo-1,4-dihydroquinoline-3-carboxylate To 2 ml chloroform solution of ethyl 3-ethoxy-2-(3-chloro-2,4,5-trifluorobenzoyl)acrylate prepared from 0.56 g of ethyl 3-chloro-2,4,5-trifluorobenzoylacetate by normal process was added 0.66 g of 2-amino-5-chloro-3-fluoro-6-(p-methoxybenzylamino)pyridine. The solution was concentrated under reduced pressure. To the residue were added 0.5 g of anhydrous potassium carbonate and 1.5 ml of N,N-dimethylformamide, and the mixture was stirred at 90° C. for 20 minutes and allowed to cool. The solution was separated by adding 30 ml of chloroform and 300 ml of distilled water, and the chloroform layer was washed with 300 ml of distilled water, dried over anhydrous magnesium sulfate, and concentrated under reduced pressure. The solution was allowed to stand after adding 4 ml of ethanol. The precipitate was collected by filtration, washed with ethanol and diisopropylether successively to obtain 0.56 g of the title compound as a pale yellow powder.

Melting point: 168 to 171° C.; $^1$HNMR (CDCl$_3$) δ; 1.40 (t, J=7 Hz, 3H), 3.80 (s, 3H), 4.40 (d, J=7 Hz, 2H), 4.42 (q, J=7 Hz, 2H), 5.46 (brs, 1H), 6.83 (d, J=9 Hz, 2H), 7.18 (d, J=9 Hz, 2H), 7.53 (d, J=8 Hz, 1H), 8.29 (t, J=9 Hz, 1H), 8.48 (s, 1H).

EXAMPLE 77

Synthesis of ethyl 1-(6-amino-5-chloro-3-fluoropyridine-2-yl)-8-chloro-6,7-difluoro-4-oxo-1,4-dihydroquinoline-3-carboxylate To 530 mg of ethyl 8-chloro-1-[5-chloro-3-fluoro-6-(p-methoxybenzylamino)pyridine-2-yl]-6,7-difluoro-4-oxo-1,4-dihydroquinoline-3-carboxylate was added 2 ml of trifluoro acetate, and the solution was allowed to stand for 30 minutes at room temperature. The solution was concentrated under reduced pressure, and 4 ml of ethanol was added to the residue, and the solution was concentrated under reduced pressure. The precipitate was dispersed in ethanol, collected by filtration, washed with ethanol and diisopropylether successively to obtain 462 mg of the title compound as a pale yellow powder.

Melting point: 186 to 189° C.; $^1$HNMR (CDCl$_3$) δ; 1.40 (t, J=7 Hz, 3H), 4.40 (q, J=7 Hz, 2H), 5.02 (brs, 2H), 7.57 (d, J=8 Hz, 2H), 8.30 (t, J=9 Hz, 1H), 8.48 (s, 1H).

EXAMPLE 78

Synthesis of 1-(6-amino-5-chloro-3-fluoropyridine-2-yl)-8-chloro-6,7-difluoro-4-oxo-1,4-dihydroquinoline-3-carboxylic acid To 2 ml of the mixed solution of 4N hydrochloric acid and acetic acid (1:1) was added 430 mg of ethyl 1-(6-amino-5-chloro-3-fluoropyridine-2-yl)-8-chloro-6,7-difluoro-4-oxo-1,4-dihydroquinoline-3-carboxylate, and the mixture was heated under reflux for 6 hours with stirring and allowed to cool. The precipitate was collected by filtration, and washed with ethanol and diisopropylether successively to obtain 375 mg of the title compound as a colorless powder.

Melting point: 280° C. or higher; $^1$HNMR ($d_6$-DMSO) δ; 6.86 (brs, 2H), 8.15 (d, J=9 Hz, 1H), 8.38 (t, J=9 Hz, 1H), 8.95 (s, 1H).

EXAMPLE 79

Synthesis of 7-(3-aminoazetidine-1-yl)-1-(6-amino-5-chloro-3-fluoropyridine-2-yl)-8-chloro-6-fluoro-4-oxo-1,4-dihydroquinoline-3-carboxylic acid To 280 mg of N,N-dimethylformamide were added 90 mg of 1-(6-amino-5-chloro-3-fluoropyridine-2-yl)-8-chloro-6,7-difluoro-4-oxo-1,4-dihydroquinoline-3-carboxylic acid, 70 mg of 3-aminoazetidine dihydrochloride, and 160 mg of N-methylpyrrolidine, and the mixture was stirred at 85° C. for 20 minutes. After adding 0.3 ml of ethanol, the mixture was allowed to cool, and the precipitate was collected by filtration and washed with ethanol and diisopropylether successively to obtain 50 mg of the title compound as a colorless powder.

Melting point: 240 to 245° C. (decomposed); $^1$HNMR ($d_6$-DMSO) δ; 3.71 (m, 1H), 4.06 (m, 2H), 4.66 (m, 2H), 6.79 (brs, 2H), 7.85 (d, J=14 Hz, 1H), 8.08 (d, J=9 Hz, 1H), 8.70 (s, 1H).

REFERENCE EXAMPLE 49

Synthesis of 2,3,5-trifluoro-6-isopropylaminopyridine

To 20 ml of acetonitrile were added 6.0 g of 2,3,5,6-tetrafluoropyridine and 6.0 g of isopropylamine, and the mixture was stirred at room temperature for 2 hours and concentrated under reduced pressure. After adding 40 ml of chloroform, the solution was washed with 50 ml of 3% aqueous solution of potassium carbonate. The chloroform layer was dried over anhydrous magnesium sulfate and concentrated under reduced pressure to obtain 1.9 g of the title compound as a colorless oil.

REFERENCE EXAMPLE 50

Synthesis of 3,5-difluoro-2-isopropylamino-6-(p-methoxybenzylamino)pyridine

To 4.1 g of N-methylpyrrolidone were added all amount of the 2,3,5-trifluoro-6-isopropylaminopyridine as described above together with 3.1 g of p-methoxybenzylamine, and the mixture was stirred at 150° C. for 15 hours and allowed to cool. After adding 50 ml of the mixed solution of benzene and n-hexane (1:1, v/v), the solution was washed twice with 400 ml of distilled water. The organic layer was dried over anhydrous magnesium sulfate and concentrated under reduced pressure to obtain 3.9 g of the title compound as a brown crude oil.

REFERENCE EXAMPLE 51

Synthesis of 2-amino-3,5-difluoro-6-isopropylaminopyridine

To 1.9 g of 3,5-difluoro-2-isopropylamino-6-(p-methoxybenzylamino)pyridine was added 4 ml of trifluoroacetate, and the mixture was allowed to stand at room temperature for 15 minutes. The solution was concentrated under reduced pressure, and 25 ml of chloroform was added to the residue, and the solution was washed with 25 ml of 5% aqueous solution of sodium carbonate. The chloroform layer was dried over anhydrous magnesium sulfate and concentrated under reduced pressure, and the residue was subjected to column chromatography (silica gel, 40 g; eluent: chloroform) to obtain 0.6 g of the title compound as a brown oil.

EXAMPLE 80

Synthesis of ethyl 8-chloro-6,7-difluoro-1-(3,5-difluoro-6-isopropylaminopyridine-2-yl)-4-oxo-1,4-dihydroquinoline-3-carboxylate To 2.5 ml of chloroform solution of ethyl 3-ethoxy-2-(3-chloro-2,4,5-trifluorobenzoyl)acrylate prepared from 0.70 g of ethyl 3-chloro-2,4,5-trifluorobenzoylacetate by normal process was added 600 mg of 2-amino-3,5-difluoro-6-isopropylaminopyridine. The solution was concentrated under reduced pressure. To the residue were added 600 mg of anhydrous potassium carbonate and 2 ml of N,N-dimethylformamide, and the mixture was stirred at 90° C. for 20 minutes and allowed to cool. The solution was separated by adding 30 ml of chloroform and 400 ml of distilled water, and the chloroform layer was washed twice with 400 ml of distilled water, dried over anhydrous magnesium sulfate, concentrated under reduced pressure, and allowed to stand. The precipitate was collected by filtration, washed with ethanol and diisopropylether successively to obtain 620 mg of the title compound as a pale yellow powder.

Melting point: 206 to 209° C.; $^1$HNMR (CDCl$_3$) δ; 1.20 (d, J=7 Hz, 3H), 1.24 (d, J=7 Hz, 3H), 1.40 (t, J=7 Hz, 3H), 4.11 (m, 1H), 4.40 (q, J=7 Hz, 2H), 4.60 (brs, 1H), 7.22 (dd, J=8 Hz, 9 Hz, 1H), 8.32 (dd, J=8 Hz, 10 Hz, 1H), 8.49 (s, 1H).

EXAMPLE 81

Synthesis of 8-chloro-6,7-difluoro-1-(3,5-difluoro-6-isopropylaminopyridine-2-yl)-4-oxo-1,4-dihydroquinoline-3-carboxylic acid To 3 ml of the mixed solution of 4N hydrochloric acid and acetic acid (1:1, v/v) was added 300 mg of ethyl 8-chloro-6,7-difluoro-1-(3,5-difluoro-6-isopropylaminopyridine-2-yl)-4-oxo-1,4-dihydroquinoline-3-carboxylate, and the mixture was heated under reflux for 19 hours with stirring. The precipitate was collected by filtration, washed with ethanol and diisopropylether successively to obtain 265 mg of the title compound as a yellow powder.

Melting point: 226 to 230° C.; $^1$HNMR (d6-DMSO) δ; 1.10 (d, J=7 Hz, 3H), 1.16 (d, J=7 Hz, 3H), 3.94 (m, 1H), 7.02 (brd, J=8 Hz, 2H), 7.97 (t, J=9 Hz, 1H), 8.39 (t, J=9 Hz, 1H), 8.92 (s, 1H).

EXAMPLE 82

Synthesis of 7-(3-aminoazetidine-1-yl)-8-chloro-6-fluoro-1-(3,5-difluoro-6-isopropylaminopyridine-2-yl)-4-oxo-1,4-dihydroquinoline-3-carboxylic acid To 160 mg of N,N-dimethylformamide were added 55 mg of 8-chloro-6,7-difluoro-1-(3,5-difluoro-6-isopropylaminopyridine-2-yl)-4-oxo-1,4-dihydroquinoline-3-carboxylic acid, 35 mg of 3-aminoazetidine dihydrochloride, and 120 mg of N-methylpyrrolidine, and the mixture was stirred at 80° C. for 30 minutes. After adding 0.5 ml of ethanol, the mixture was allowed to cool, and the precipitate was collected by filtration and washed with ethanol and diisopropylether successively to obtain 51 mg of the title compound as a colorless powder.

Melting point: 220 to 223° C.; $^1$HNMR ($d_6$-DMSO) δ; 1.13 (d, J=7 Hz, 3H), 1.16 (d, J=7 Hz, 3H), 3.70 (m, 1H), 3.96 (m, 2H), 4.06 (m, 1H), 4.65 (m, 2H), 6.92 (brd, J=7 Hz, 2H), 7.87 (d, J=14 Hz, 1H), 7.92 (t, J=9 Hz, 1H), 8.66 (s, 1H).

EXAMPLE 83

Synthesis of ethyl 1-[3,5-difluoro-6-(p-methoxybenzylamino)pyridine-2-yl]-5,6,7,8-tetrafluoro-4-oxo-1,4-dihydroquinoline-3-carboxylate To 20 ml of chloroform solution of ethyl 3-ethoxy-2-pentafluorobenzoylacrylate prepared from 5.6 g of ethyl 2,3,4,5,6-pentafluorobenzoylacetate by normal process was added 2-amino-3,5-difluoro-6-(p-methoxybenzylamino) pyridine until the disappearance of the ethyl acrylate spot in TLC analysis. The solution was concentrated under reduced pressure. To the residue were added 4.3 g of anhydrous potassium carbonate and 15 ml of N,N-dimethylformamide, and the mixture was stirred at 90° C. for 15 minutes and allowed to cool. The solution was separated by adding 100 ml of chloroform and 1 liter of distilled water, and the chloroform layer was washed twice with 1 liter of distilled water, dried over anhydrous magnesium sulfate, and concentrated under reduced pressure. The precipitate was dispersed in ethanol, collected by filtration, and washed with ethanol and diisopropylether successively to obtain 6.15 g of the title compound as a colorless powder.

Melting point: 203 to 208° C.; $^1$HNMR (CDCl$_3$) δ; 1.40 (t, J=7 Hz, 3H), 3.80 (s, 3H), 4.40 (d, J=7 Hz, 2H), 4.42 (q, J=7 Hz, 2H), 5.46 (brs, 1H), 6.83 (d, J=9 Hz, 2H), 7.18 (d, J=9 Hz, 2H), 7.53 (d, J=8 Hz, 1H), 8.29 (t, J=9 Hz, 1H), 8.48 (s, 1H).

EXAMPLE 84

Synthesis of ethyl 1-(6-amino-3,5-difluoropyridine-2-yl)-5,6,7,8-tetrafluoro-4-oxo-1,4-dihydroquinoline-3-carboxylate To 1080 mg of ethyl 1-[3,5-difluoro-6-(p-methoxybenzylamino)pyridine-2-yl]-5,6,7,8-tetrafluoro-4-oxo-1,4-dihydroquinoline-3-carboxylate was added 4 ml of trifluoroacetic acid, and the mixture was allowed to stand at room temperature for 30 minutes. The solution was concentrated under reduced pressure, and 4 ml of ethanol was added to the residue, and the solution was again concentrated under reduced pressure. The precipitate was dispersed in ethanol, collected by filtration, and washed with ethanol to obtain 960 mg of the title compound as a gray powder.

Melting point: 223 to 230° C. $^1$HNMR (CDCl$_3$) δ; 1.39 (t, J=7 Hz, 3H), 4.38 (d, J=7 Hz, 2H), 4.83 (brs, 2H), 6.83 (d, J=9 Hz, 2H), 7.35 (t, J=9 Hz, 1H), 8.32 (s, 1H).

EXAMPLE 85

Synthesis of 1-(6-amino-3,5-difluoropyridine-2-yl)-5,6,7,8-tetrafluoro-4-oxo-1,4-dihydroquinoline-3-carboxylic acid To 2 ml of the mixed solution (1:1) of 4N hydrochloric acid and acetic acid was added 320 mg of ethyl 1-(6-amino-3,5-difluoropyridine-2-yl)-5,6,7,8-tetrafluoro-4-oxo-1,4-dihydroquinoline-3-carboxylate, and the mixture was heated under reflux for 3 hours with stirring, and allowed to cool. The precipitate was collected by filtration, and washed with ethanol to obtain 280 mg of the title compound as a colorless powder.

Melting point: 236 to 242° C. $^1$HNMR (d$_6$-DMSO) δ; 6.82 (brs, 2H), 8.03 (t, J=9 Hz, 1H), 8.92 (s, 1H).

EXAMPLE 86

Synthesis of 7-(3-aminoazetidine-1-yl)-1-(6-amino-3,5-difluoropyridine-2-yl)-5,6,8-trifluoro-4-oxo-1,4-dihydroquinoline-3-carboxylic acid To 300 mg of N,N-dimethylformamide were added 100 mg of 1-(6-amino-3,5-difluoropyridine-2-yl)-5,6,7,8-tetrafluoro-4-oxo-1,4-dihydroquinoline-3-carboxylic acid, 70 mg of 3-aminoazetidine dihydrochloride, and 150 mg of N-methylpyrrolidine, and the mixture was stirred at 90° C. for 30 minutes. After adding 0.3 ml of ethanol, the mixture was allowed to cool, and the precipitate was collected by filtration and washed with ethanol and diisopropylether successively to obtain 50 mg of the title compound as a pale yellow powder.

Melting point: 264 to 271° C. (decomposed); $^1$HNMR (d$_6$-DMSO) δ; 3.77 (m, 1H), 3.96 (m, 2H), 4.46 (m, 2H), 6.75 (brs, 2H), 7.97 (t, J=9 Hz, 1H), 8.66 (S, 1H).

EXAMPLE 87

Synthesis of ethyl 5-benzylamino-1-[3,5-difluoro-6-(p-methoxybenzylamino)pyridine-2-yl]-6,7,8-trifluoro-4-oxo-1,4-dihydroquinoline-3-carboxylate To 8 ml of toluene were added 1.58 g of ethyl 1-[3,5-difluoro-6-(p-methoxybenzylamino)pyridine-2-yl]-5,6,7,8-tetrafluoro-4-oxo-1,4-dihydroquinoline-3-carboxylate together with 0.68 g of benzylamine, and the mixture was stirred at 110° C. for 20 minutes and allowed to cool. After adding 15 ml of toluene and 15 ml of n-hexane, the mixture was washed twice with 300 ml of distilled water. The organic layer was dried over anhydrous magnesium sulfate, and concentrated under reduced pressure. To the residue was added 4 ml of ethanol, and the solution was allowed to stand, and the precipitate was collected by filtration and washed with ethanol to obtain 1.20 g of the title compound as a yellow powder.

Melting point: 146 to 148° C.; $^1$HNMR (CDCl$_3$) δ; 1.37 (t, J=7 Hz, 3H), 3.79 (s, 3H), 4.37 (q, J=7 Hz, 2H), 4.47 (brs, 1H), 4.68 (m, 2H), 5.01 (brs, 1H), 6.84 (d, J=9 Hz, 2H), 7.16–7.40 (m, 10H), 8.22 (s, 1H).

EXAMPLE 88

Synthesis of ethyl 1-(6-amino-3,5-difluoropyridine-2-yl)-5-benzylamino-6,7,8-trifluoro-4-oxo-1,4-dihydroquinoline-3-carboxylate To 600 mg of ethyl 5-benzylamino-1-[3,5-difluoro-6-(p-methoxybenzylamino)pyridine-2-yl]-6,7,8-trifluoro-4-oxo-1,4-dihydroquinoline-3-carboxylate was added 2 ml of trifluoroacetic acid, and the mixture was allowed to stand at room temperature for 20 minutes. The solution was concentrated under reduced pressure, and 3 ml of ethanol was added to the residue, and the solution was again concentrated under reduced pressure. The precipitate was dispersed in ethanol, collected by filtration and washed with ethanol to obtain 530 mg of the title compound as a yellow powder.

Melting point: 176 to 180° C.; $^1$HNMR (CDCl$_3$) δ; 1.36 (t, J=7 Hz, 3H), 4.36 (q, J=7 Hz, 2H), 4.47 (brs, 1H), 4.68 (d, J=4 Hz, 2H), 4.74 (brs, 1H), 6.84 (d, J=9 Hz, 2H), 7.24–7.40 (m, 6H), 8.21 (s, 1H).

EXAMPLE 89

Synthesis of ethyl 5-amino-1-(6-amino-3,5-difluoropyridine-2-yl)-6,7,8-trifluoro-4-oxo-1,4-dihydroquinoline-3-carboxylate To 5 ml of acetic acid was added 260 mg of ethyl 1-(6-amino-3,5-difluoropyridine-2-yl)-5-benzylamino-6,7,8-trifluoro-4-oxo-1,4-dihydroquinoline-3-carboxylate together with 50 mg of 10% palladium on carbon, and the mixture was hydrogenated at room temperature for 4 hours. The catalyst was separated by filtration, and the solvent and the like were distilled off under reduced pressure. The procedure of adding 10 ml of ethanol to the residue and concentrating under reduced pressure was repeated twice.

The precipitate was dispersed in ethanol, collected by filtration, and washed with ethanol and diisopropylether successively to obtain 160 mg of the title compound as a pale yellow powder.

Melting point: 225 to 230° C.; $^1$HNMR (CDCl$_3$) δ; 1.38 (t, J=7 Hz, 3H), 4.38 (q, J=7 Hz, 2H), 4.73 (brs, 2H), 4.68 (d, J=4 Hz, 2H), 6.8 (brs, 2H), 6.84 (d, J=9 Hz, 2H), 7.32 (t, J=9 Hz, 1H), 8.25 (s, 1H).

EXAMPLE 90

Synthesis of 5-amino-1-(6-amino-3,5-difluoropyridine-2-yl)-6,7,8-trifluoro-4-oxo-1,4-dihydroquinoline-3-carboxylic acid To 1.5 ml of the mixed solution (1:1) of 4N hydrochloric acid and acetic acid was added 145 mg of ethyl 5-amino-1-(6-amino-3,5-difluoropyridine-2-yl)-6,7,8-trifluoro-4-oxo-1,4-dihydroquinoline-3-carboxylate, and the mixture was heated under reflux for 17 hours with stirring and allowed to cool. The precipitate was collected by filtration, and washed with ethanol and to obtain 129 mg of the title compound as a yellow powder.

$^1$HNMR (d$_6$-DMSO) δ; 6.78 (brs, 2H), 7.75 (brs, 1H), 7.99 (t, J=9 Hz, 1H), 8.77 (s, 1H).

EXAMPLE 91

Synthesis of 5-amino-7-(3-aminoazetidine-1-yl)-1-(6-amino-3,5-difluoropyridine-2-yl)-6,8-difluoro-4-oxo-1,4-dihydroquinoline-3-carboxylic acid To 210 mg of N,N-dimethylformamide were added 50 mg of 5-amino-1-(6-amino-3,5-difluoropyridine-2-yl)- 6,7,8-trifluoro-4-oxo-1,4-dihydroquinoline-3-carboxylic acid, 40 mg of 3-aminoazetidine dihydrochloride, and 150 mg of N-methylpyrrolidine, and the mixture was stirred at 90° C. for 1 hour, and concentrated under reduced pressure. The procedure of adding 2 ml of diisopropylether to the residue, stirring and decanting was repeated twice. 2 ml of ethanol and 40 mg of N-methylpyrrolidine were added to the residue, and the mixture was allowed to stand overnight, and the precipitate was collected by filtration and washed with ethanol and diisopropylether successively to obtain 26 mg of the title compound as a pale yellow powder.

Melting point: 205 to 210° C. (decomposed); $^1$HNMR (d$_6$-DMSO) δ; 3.72 (m, 1H), 3.88 (m, 2H), 4.37 (m, 2H), 6.71 (brs, 2H), 7.23 (brs, 2H), 7.94 (t, J=9 Hz, 1H), 8.50 (s, 1H).

EXAMPLE 92

Synthesis of ethyl 1-(6-t-butylamino-3,5-difluoropyridine-2-yl)-8-chloro-6,7-difluoro-5-nitro-4-oxo-1,4-dihydroquinoline-3-carboxylate To 10 ml of chloroform solution of ethyl 3-ethoxy-2-(3-chloro-2,4,5-trifluoro-6-nitrobenzoyl)acrylate prepared from 3.25 g of ethyl 3-chloro-2,4,5-trifluoro-6-nitrobenzoylacetate by normal process was added 2.14 g of 2-amino-3,5-difluoro-6-t-butylaminopyridine. The solution was concentrated under reduced pressure, and to the residue were added 2.7 g of anhydrous potassium carbonate and 10 ml of N,N-dimethylformamide, and the mixture was stirred at 90° C. for 5 minutes and allowed to cool. The solution was separated by adding 100 ml of chloroform and 500 ml of 2% aqueous solution of citric acid, and the chloroform layer was washed twice with 500 ml of 2% aqueous solution of citric acid, dried over anhydrous magnesium sulfate, and concentrated under reduced pressure. The precipitate was dispersed in ethanol, collected by filtration, washed with ethanol and diisopropylether successively to obtain 3.13 g of the title compound as a pale yellow powder.

Melting point: 215 to 217° C.; $^1$HNMR (CDCl$_3$) δ; 1.37 (t, J=7 Hz, 3H), 1.39 (s, 9H), 4.39 (q, J=7 Hz, 2H), 4.77 (brs, 1H), 7.24 (t, J=8 Hz, 1H), 8.35 (t, J=9 Hz, 1H), 8.52 (s, 1H).

EXAMPLE 93

Synthesis of 5-amino-1-(6-amino-3,5-difluoropyridine-2-yl)-8-chloro-6,7-difluoro-4-oxo-1,4-dihydroquinoline-3-carboxylic acid To 10 ml of formic acid was added 960 mg of ethyl 1-(6-t-butylamino-3,5-difluoropyridine-2-yl)-8-chloro-6,7-difluoro-5-nitro-4-oxo-1,4-dihydroquinoline-3-carboxylate together with 1.0 g of iron powder, and the mixture was stirred at 80 to 90° C. for 5 hours and 40 minutes. The insoluble content was separated by filtration through celite, and the content separated by the celite and the celite were washed with formic acid and chloroform. The filtrate and the washings were concentrated under reduced pressure. To the residue was added the 6 ml of the mixed solution of 4N hydrochloric acid and acetic acid (1:1), and the mixture was heated under reflux for 2 hours with stirring and allowed to cool. The precipitate was collected by filtration and washed with ethanol and diisopropylether successively to obtain 625 mg of the title compound as a yellow powder.

Melting point: 280° C. or higher; $^1$HNMR (d$_6$-DMSO) δ; 6.77 (brs, 2H), 7.94 (t, J=9 Hz, 1H), 8.20 (brs, 2H), 8.70 (s, 1H).

EXAMPLE 94

Synthesis of 5-amino-7-(3-aminoazetidine-1-yl)-1-(6-amino-3,5-difluoropyridine-2-yl)-8-chloro-6-fluoro-4-oxo-1,4-dihydroquinoline-3-carboxylic acid To 550 mg of pyridine were added 185 mg of 5-amino-1-(6-amino-3 , 5-difluoropyridine-2-yl)-8-chloro-6,7-difluoro-4-oxo-1,4-dihydroquinoline-3-carboxylic acid, 110 mg of 3-aminoazetidine dihydrochloride, and 200 mg of N-methylpyrrolidine, and the mixture was stirred at 100° C. for 30 minutes, and concentrated under reduced pressure. After adding 2 ml of ethanol, the mixture was stirred, and the precipitate was collected by filtration and washed with ethanol and diisopropylether successively to obtain 48 mg of the title compound as a yellow powder.

$^1$HNMR (d$_6$-DMSO) δ; 3.83 (m, 1H), 4.14 (m, 2H), 4.61 (m, 2H), 6.71 (brs, 2H), 7.52 (brs, 2H), 7.89 (t, J=9 Hz, 1H), 8.51 (s, 1H).

EXAMPLE 95

Synthesis of ethyl 6,7-difluoro-1-(3,5-difluoro-6-p-methoxybenzylaminopyridine-2-yl)-8-methyl-5-nitro-1,4-dihydro-4-oxoquinoline-3-carboxylate To 5.0 g of ethyl 3,4,6-trifluoro-5-methyl-2-nitrobenzoylacetate were added 11.5 g of acetic anhydride and 4.7 g of triethyl orthoformate, and the mixture was heated under reflux for 1.5 hours. The reaction solution was allowed to cool, and the reagent and the like were distilled off, and toluene was added to the residue for azeotropic distillation. The residue was added to 10 ml of ethanol, and a solution of 5.0 g of 2-amino-3,5-difluoro-6-(p-methoxybenzylamino)pyridine in 15 ml of ethanol was added dropwise to the mixture in an ice bath and the mixture was stirred at room temperature for 10 minutes. The solvent was distilled off the reaction solution, and the residue was subjected to silica gel column chromatography to obtain 7.1 g of oil from the fractions eluted by ethyl acetate: hexane, 1:10. To 7.0 g of this oil were added 10 ml of N,N-dimethylformamide and 2.0 g of potassium carbonate, and the mixture was stirred at 70° C. for 30 minutes. To the reaction solution was added ethyl acetate and water, and the organic layer was separated and dried over magnesium sulfate. The solvent was distilled off and ethanol was added to the residue to disperse the solid content for collection by filtration to thereby obtain 1.5 g of the title compound as a pale yellow powder.

Melting point: 225 to 227° C.; $^1$HNMR (CDCl$_3$) δ; 1.37 (t, J=7 Hz, 3H), 1.68 (d, J=3 Hz, 3H), 3.81 (s, 3H), 4.39 (q, J=7 Hz, 2H), 4.45 (s, 2H), 5.29 (brs, 1H), 6.83 (d, J=8 Hz, 2H), 7.17 (d, J=8 Hz, 2H), 7.31 (t, J=9 Hz, 1H), 8.45 (s, 1H).

EXAMPLE 96

Synthesis of ethyl 5-amino-6,7-difluoro-1-(3,5-difluoro-6-p-methoxybenzylaminopyridine-2-yl)-8-methyl-1,4-dihydro-4-oxoquinoline-3-carboxylate To 10 ml of acetic acid solution of 1.7 g of ethyl 6,7-difluoro-1-(4,6-difluoro-3-p-methoxybenzylaminopyridine-2-yl)-8-methyl-5-nitro-1,4-dihydro-4-oxoquinoline-3-carboxylate was added 1.4 g of iron powder, and the mixture was heated and stirred at 90° C. for 4 hours and 40 minutes. The catalyst in the reaction solution was removed by filtration, and the solvent in the filtrate was distilled off. The residue was subjected to silica gel column chromatography. The fraction eluted by chloroform: methanol, 10:1 was concentrated, and ethanol was added to the residue. The powder precipitate was collected by filtration to obtain 1.3 g of the title compound as a pale brown powder.

Melting point: 150 to 153° C.; $^1$HNMR (d$_6$-DMSO) ≡; 1.24 (t, J=7 Hz, 3H), 1.30 (s, 3H), 3.71 (s, 3H), 4.20 (q, J=7 Hz, 2H), 4.33 (dd, J=5 Hz, 12 Hz, 2H), 6.76 (d, J=8 Hz, 2H), 7.14 (d, J=8 Hz, 2H), 7.85 (brs, 1H), 7.93 (t, J=10 Hz, 1H), 8.27 (s, 1H).

EXAMPLE 97

Synthesis of 5-amino-1-(6-amino-3,5-difluoropyridine-2-yl)-6,7-difluoro-8-methyl-1,4-dihydro-4-oxoquinoline-3-carboxylic acid To 0.99 g of ethyl 5-amino-6,7-difluoro-1-(3,5-difluoro-6-p-methoxybenzylaminopyridine-2-yl)-8-methyl-1,4-dihydro-4-oxoquinoline-3-carboxylate was added 10 ml of 12N hydrochloric acid, and the mixture was heated under reflux for 10 hours. The reaction solution was allowed to cool, and the solid content was collected by filtration. The solid content was washed with ethanol, and then, with diethylether to obtain 880 mg of the title compound as a yellow powder.

Melting point: 250° C. or higher (decomposed); $^1$HNMR (d$_6$-DMSO) δ; 1.60 (s, 3H), 6.80 (brs, 2H), 7.96 (t, J=9 Hz, 1H), 8.69 (s, 1H).

REFERENCE EXAMPLE 52

Synthesis of 2-amino-4-bromo-5-chloro-3,6-difluoropyridine

To 20 ml of acetonitrile were added 4.9 g of 4-bromo-3-chloro-2,5,6-trifluoropyridine and 4 ml of 25% aqueous solution of ammonia, and the mixture was stirred at 55° C. for 2 hours. The solvent and the like were distilled off under reduced pressure. 50 ml of chloroform was added to the residue, and the solution was washed with 50 ml of distilled water. The chloroform layer was dried over anhydrous magnesium sulfate and concentrated under reduced pressure. The residue was dispersed in the mixed solution of diisopropylether and n-hexane and collected by filtration to obtain 3.8 g of the title compound as pale yellow needle crystals. 5

REFERENCE EXAMPLE 53

Synthesis of. 2-amino-4-bromo-5-chloro-3-fluoro-6-(1,1,3,3-tetramethylbutylamino)pyridine To 6 ml of N-methylpyrrolidone were added 2.4 g of 2-amino-4-bromo-5-chloro-3,6-difluoropyridine and 3.5 g of 1,1,3,3-tetramethylbutylamine, and the mixture was stirred at 140° C. for 82 hours and allowed to cool. 50 ml of the mixed solution of benzene and n-hexane (1:1, v/v) was added, and the solution was washed twice with 400 ml of distilled water. The organic layer was dried over anhydrous magnesium sulfate and concentrated under reduced pressure. The brown oily residue was subjected to column chromatography (silica gel, 30 g; eluent: chloroform:n-hexane, 1:1) to obtain 1.6 g of the title compound as a colorless oily residue.

REFERENCE EXAMPLE 54

Synthesis of 2-amino-3-fluoro-6-(1,1,3,3-tetramethyl-butylamino)pyridine

To 10 ml of methanol were added 1.6 g of 2-amino-4-bromo-5-chloro-3-fluoro-6-(1,1,3,3-tetramethylbutylamino)pyridine together with 0.47 g of triethylamine and 0.09 g of 10% palladium on carbon, and the mixture was hydrogenated at room temperature for 39 hours. The catalyst was separated by filtration, and the solvent and the like were distilled off under reduced pressure. To the residue was added 50 ml of chloroform, and the mixture was washed with 50 ml of distilled water. The chloroform layer was dried over anhydrous magnesium sulfate and concentrated under reduced pressure. The residue was subjected to chromatography (silica gel, 25 g; eluent: chloroform) to obtain 0.75 g of 2-amino-3-fluoro-6-(1,1,3,3-tetramethylbutylamino)pyridine as a pale brown oil, and 0.2 g of 2-amino-4-bromo-3-fluoro-6-(1,1,3,3-tetramethylbutylamino)pyridine as a brown oil.

EXAMPLE 98

Synthesis of ethyl 1-[3-fluoro-6-(1,1,3,3-tetramethylbutylamino)pyridine-2-yl]-8-chloro-6,7-difluoro-4-oxo-1,4-dihydroquinoline-3-carboxylate To 3 ml chloroform solution of ethyl 3-ethoxy-2-(3-chloro-2,4,5-trifluorobenzoyl)acrylate prepared from 0.84 g of ethyl 3-chloro-2,4,5-trifluorobenzoylacetate by normal process was added 0.75 g of 2-amino-3-fluoro-6-(1,1,3,3-tetramethylbutylamino)pyridine. The solution was concentrated under reduced pressure, and to the residue were added 0.65 g of anhydrous potassium carbonate and 1.5 ml of N,N-dimethylformamide, and the mixture was stirred at 90° C. for 1 hour and allowed to cool. The solution was separated by adding 30 ml of chloroform and 300 ml of distilled water, and the chloroform layer was washed twice with 300 ml of distilled water, dried over anhydrous magnesium sulfate, and concentrated under reduced pressure. The precipitate was collected by filtration and washed with ethanol and diisopropylether successively to obtain 0.45 g of the title compound as a pale yellow powder.

Melting point: 178 to 180° C.; $^1$HNMR (CDCl$_3$) δ; 0.96 (s, 9H), 1.41 (m, 9H), 1.77 (dd, J=15 Hz, 22 Hz, 2H), 4.42 (q, J=7 Hz, 2H), 4.53 (brs, 1H), 6.44 (dd, J=3 Hz, 9 Hz, 1H), 7.30 (t, J=9 Hz, 1H), 8.30 (t, J=9 Hz, 1H), 8.56 (s, 1H).

EXAMPLE 99

Synthesis of 1-(6-amino-3-fluoropyridine-2-yl)-8-chloro-6,7-difluoro-4-oxo-1,4-dihydroquinoline-3-carboxylic acid To 1.2 ml of the mixed solution of 4N hydrochloric acid and acetate (1:1) was added 235 mg of ethyl 1-[3-fluoro-6-(1,1,3,3-tetramethylbutylamino)pyridine-2-yl]-8-chloro-6,7-difluoro-4-oxo-1,4-dihydroquinoline-3-carboxylate and the mixture was heated under reflux for 6 hours with stirring and allowed to cool. The precipitate was collected by filtration and washed with ethanol to obtain 145 mg of the title compound as a gray powder.

Melting point: 228 to 230° C.; $^1$HNMR (d$_6$-DMSO) δ; 6.70 (dd, J=3 Hz, 9 Hz, 1H), 7.66 (t, J=9 Hz, 1H), 8.38 (t, J=9 Hz, 1H), 8.87 (s, 1H).

EXAMPLE 100

Synthesis of 7-(3-aminoazetidine-1-yl)-1-(6-amino-3-fluoropyridine-2-yl)-8-chloro-6-fluoro-4-oxo-1,4-dihydroquinoline-3-carboxylic acid To 190 mg of N,N-dimethylformamide were added 57 mg of 1-(6-amino-3-fluoropyridine-2-yl)-8-chloro-6,7-difluoro-4-oxo-1,4-dihydroquinoline-3-carboxylic acid, 37 mg of 3-aminoazetidine dihydrochloride, and 100 mg of N-methylpyrrolidine, and the mixture was stirred at 90° C. for 30 minutes. After adding 0.2 ml of ethanol, the mixture was allowed to cool, and the precipitate was collected by filtration and washed with ethanol and diisopropylether successively to obtain 40 mg of the title compound as a colorless powder.

Melting point: 250 to 255° C. (decomposed); $^1$HNMR (d6-DMSO) δ; 3.71 (m, 1H), 4.04 (m, 2H), 4.67 (m, 2H), 6.44 (brs, 2H), 6.62 (dd, J=3 Hz, 9 Hz, 1H), 7.61 (d, J=9 Hz, 1H), 7.85 (t, J=14 Hz, 1H), 8.63 (s, 1H).

EXAMPLE 101

Synthesis of 5-amino-1-(6-amino-3,5-difluoropyridine-2-yl)-8-chloro-6-fluoro-7-(3-methylaminoazetidine-1-yl)-4-oxo-1,4-dihydroquinoline-3-carboxylic acid To 300 mg of pyridine were added 120 mg of 5-amino-1-(6-amino-3,5-difluoropyridine-2-yl)-8-chloro-6,7-difluoro-4-oxo-1,4-dihydroquinoline-3-carboxylic acid, 80 mg of 3-methylaminoazetidine diacetate, and 250 mg of N-methylpyrrolidine, and the mixture was stirred at 100° C. for 10 minutes. After adding 5 ml of diethylether, the mixture was stirred and allowed to cool for 1 hour, and decanted. 2 ml of ethanol was added and the mixture was stirred. The precipitate was collected by filtration and washed with ethanol and diethylether successively to obtain 72 mg of the title compound as a yellow powder.

Melting point: 204 to 213° C. $^1$HNMR (d$_6$-DMSO) δ; 2.02 (s, 3H), 4.05 (m, 2H), 4.57 (m, 2H), 6.70 (brs, 2H), 7.48 (brs, 1H), 7.89 (t, J=10 Hz, 1H), 8.49 (s, 1H).

EXAMPLE 102

Synthesis of 5-amino-1-(6-amino-3,5-difluoropyridine-2-yl)-8-chloro-6-fluoro-7-(3-hydroxyaminoazetidine-1-yl)-4-oxo-1,4-dihydroquinoline-3-carboxylic acid To 300 mg of pyridine were added 120 mg of 5-amino-1-(6-amino-3,5-difluoropyridine-2-yl)-8-chloro-6,7-difluoro-4-oxo-1,4-dihydroquinoline-3-carboxylic acid, 80 mg of 3-hydroxyaminoazetidine hydrochloride, and 250 mg of N-methylpyrrolidine, and the mixture was stirred at 100° C. for 3 minutes. After adding 5 ml of diethylether, the mixture was allowed to stand for 1 hour and decanted. 2 ml of ethanol was added and the mixture was stirred. The precipitate was collected by filtration and washed with ethanol and diethylether successively to obtain 64 mg of the title compound as a yellow powder.

Melting point: 267 to 290° C. (decomposed); $^1$HNMR (d$_6$-DMSO) δ; 4.09 (m, 2H), 4.45 (m, 1H), 4.63 (m, 2H), 5.69 (d, J=6 Hz, 1H), 6.71 (brs, 2H), 7.48 (brs, 1H), 7.89 (t, J=10 Hz, 1H), 8.51 (s, 1H).

(1) Antibacterial Action

The compounds of the Examples 9, 10, 12 and 39 as described above were evaluated for their minimum growth inhibitory concentration (MIC, μg/ml) in accordance with the standard method of Japan Chemotherapy Society (Chemotherapy 29(1), 76, 1981) using the standard strains (*S. aureus* 209P, *S. epidermidis* IF012293, *P. aeruginosa* IFO 3445). The results are shown in Table 1. It should be noted that ciprofloxacin, levofloxacin, sparfloxacin and tosufloxacin which are conventional antibacterials were also evaluated for their minimum growth inhibitory concentration (MIC, μg/ml) for the purpose of comparison. The results are also shown in Table 1.

TABLE 1

| Compound | S. aureus | S. epidermidis | P. aeruginosa |
| --- | --- | --- | --- |
| Compound of Ex. 9 | <0.013 | 0.025 | 0.05 |
| Compound of Ex. 10 | <0.013 | 0.025 | 0.10 |
| Compound of Ex. 12 | <0.013 | <0.013 | 0.39 |
| Compound of Ex. 39 | <0.013 | 0.025 | 0.05 |
| Ciprofloxacin | 0.10 | 0.39 | 0.20 |
| Levofloxacin | 0.10 | 0.39 | 0.39 |
| Sparfloxacin | 0.10 | 0.20 | 0.78 |
| Tosufloxacin | 0.05 | 0.20 | 0.39 |

The results shown in Table 1 reveal that the compounds of the present invention has excellent antibacterial activities superior to those of the conventional antibacterials.

(2) Phototoxicity Test

The compounds of the Examples 9, 10, 12 and 39 as described above were subjected to phototoxicity test by the procedure as described below.

Female ICR mice (5 to 6 week old) were intravenously administered with the test compound (40 mg/kg/10 ml), and irradiated with UV (320 to 400 nm, 1.8 mW/cm$^2$/sec) for 4 hours. Abnormality in the ears was monitored at 0 hour (immediately after the irradiation) and after 24 and 48 hours. The ear abnormality was evaluated by the following criteria: no abnormality (0 point), very slight erythema (1 point), well defined erythema (2 points), moderate to severe erythema and edema formation (3 points). The results are shown in Table 2. Tosufloxacin which is a conventional known antibacterial agent was also tested in a similar way for the purpose of comparison. The results are also shown in Table 2.

TABLE 2

| Compound | 0 hour (point, occurrence) | 24 hours | 48 hours |
|---|---|---|---|
| Compound of Ex. 9 | 0, 0/3 | 0, 0/3 | 0, 0/3 |
| Compound of Ex. 10 | 0, 0/3 | 0, 0/3 | 0, 0/3 |
| Compound of Ex. 12 | 0, 0/3 | 0, 0/3 | 0, 0/3 |
| Compound of Ex. 39 | 0, 0/3 | 0, 0/3 | 0, 0/3 |
| Tosufloxacin | 1.8, 4/5 | 0.8, 4/5 | 0.2, 1/5 |

The results shown in Table 2 demonstrate that the compounds of the present invention have very low toxicity.

We claim:

1. A pyridonecarboxylic acid derivative represented by the following formula or a pharmacologically acceptable salt thereof:

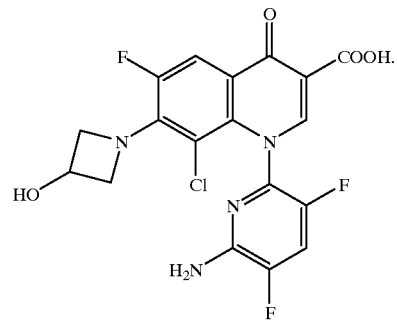

2. A method of treating a person infected with bacteria which comprises administering an pharmaceutically effective amount of the compound of claim 1 to a person in need thereof.

3. A method of treating an animal infected with bacteria which comprises administering an pharmaceutically effective amount of the compound of claim 1 to an animal in need thereof.

* * * * *